(12) United States Patent
Sundermann et al.

(10) Patent No.: US 6,410,790 B1
(45) Date of Patent: Jun. 25, 2002

(54) 3-AMIN3-ARYLPROPAN-1-OL COMPOUNDS, THEIR PREPARATION AND USE

(75) Inventors: Bernd Sundermann, Aachen; Hagen-Heinrich Hennies, Simmerath; Babette-Yvonne Koegel, Langerwehe-Hamich; Helmut Buschmann, Aachen, all of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/545,371

(22) Filed: Apr. 7, 2000

(30) Foreign Application Priority Data

Apr. 7, 1999 (DE) .......................... 199 15 601

(51) Int. Cl.$^7$ ..................... C07C 211/00; A61K 31/445
(52) U.S. Cl. ..................... 564/336; 564/342; 546/192; 546/236; 549/74; 549/365; 549/491; 560/42; 514/317; 514/538; 514/471; 514/465; 514/649; 514/438
(58) Field of Search .................. 560/42; 564/342, 564/336; 546/192, 236; 549/491, 365, 74; 514/317, 538, 471, 465, 649, 438

(56) References Cited

U.S. PATENT DOCUMENTS 4,017,637 A 4/1977 Yardley et al. ............. 424/311

FOREIGN PATENT DOCUMENTS

EP 1043306 A2 10/2000

OTHER PUBLICATIONS

Carlson et al., "Improved Titanium Tetrachloride Procedure for Enamine Sunthesis. II. Scope of the Reaction", *Acta Chemica Scandinavica B 38*, 1984, pp. 49–53.
Risch et al., "Additions of Enamines to Iminium Ions", *Houben–Weyl* E21b, 1995, pp. 1925–1929.
Risch et al., "Diastereomerenreine Mannich–Based durch Addition von Enaminen an ternäre Iminiumsalze", *Agnew. Chem*, 106, 1994, pp. 2531–2533.
Arend et al., "A Simple and Highly Diastereoselective One–Pot Synthesis of Mannich–Bases", *Synlett*, Jun. 17, 1997, pp. 974–976.
Winterfeldt, "Applications of Diisobutylaluminium Hydride (DIBAH) and Triisobutylaluminium (TIBA) as Reducing Agents in Organic Synthesis", *Synthesis*, Oct. 1975, pp. 617–630.
Hendershot et al., "Antagonism of the Frequency of Phenylquinone–Induced Writhing in the Mouse by Weak Analgesics and Nonanalgesics", *J. Pharmacol. Exp. Ther.*, 1959, pp. 237–240.
Schoemaker et al.,"[$^3$H]Diltiazem Binding to Calcium Channel Antagonists Recognition Sites in Rat Cerebral Cortex", *European Journal of Pharmacology* 111, 1985, pp. 273–277.

Gray et al., "The Isolation of Nerve Endings from Brain: an Electron–Microscopic Study of Cell Fragments Derived by Homogenization and Centrifugation", *J. Anat.* 96, 1962, pp. 79–88.
Pauwels et al., "[$^3$H]Batrachotoxinin A 20–α–Benzoate Binding to Sodium Channels in Rat Brain: Characterization and Pharmacological Significance", *European Journal of Pharmacology* 124, 1986, pp. 291–298.
Cheng et al., "Relationship Between the Inhibition Constant ($K_I$) and the Concentration of Inhibitor Which Causes 50 per cent Inhibition ($I_{50}$) of an Enzymatic Reaction", *Biochem. Pharmacology*, vol. 22, 1973, pp. 3099–3108.
Lineweaver et al., "The Determination of Enzyme Dissociation Constants", *J. Am. Chem. Soc.*, vol. 56, 1934, pp. 658–666.

*Primary Examiner*—Samuel Barts
(74) *Attorney, Agent, or Firm*—Crowell & Moring LLP

(57) ABSTRACT

3-amino-3-arylpropan-1-ol compounds of formula I:

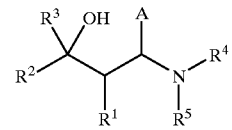

I $R^1$ and $R^2$ independently denoting $C_{1-6}$ alkyl, or together denoting a $(CH_2)_{2-6}$ ring optionally substituted by phenyl,
$R^3$ denoting $C_{3-6}$ alkyl, $C_{3-6}$ cycloalkyl, aryl optionally containing heteroatoms and optionally substituted by $R^6$ to $R^8$, or a substituted $C_{1-3}$ alkylphenyl of formula XII:

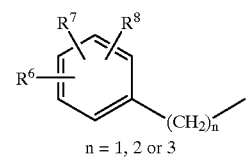

XII n = 1, 2 or 3

$R^4$ and $R^5$ independently denoting $C_{1-6}$ alkyl, $C_{3-6}$ cycloalkyl, phenyl, benzyl, or phenethyl, or together forming a $(CH_2)_{3-6}$ or $CH_2CH_2OCH_2CH_2$ ring,
$R^6$ to $R^8$ independently denoting H, F, Cl, Br, $CHF_2$, $CF_3$, OH, $OCF_3$, $OR^{14}$, $NR^{15}R^{16}$, $SR^{14}$, phenyl, $SO_2CH_3$, $SO_2CF_3$, $C_{1-6}$ alkyl, CN, $COOR^{14}$, or $CONR^{15}R^{16}$, or together forming a $OCH_2O$, $OCH_2CH_2O$, CH=CHO, CH=C($CH_3$)O or $(CH_2)_4$ ring,
$R^{14}$ denoting $C_{1-6}$ alkyl, phenyl, benzyl, or phenethyl,
$R^{15}$ and $R^{16}$ independently denoting H, $C_{1-6}$ alkyl, phenyl, benzyl or phenethyl, and
A denoting optionally substituted aryl optionally containing heteroatoms,
or a diastereomer or enantiomer or pharmaceutically acceptable salt thereof, and their preparation and use in pharmaceutical compositions.

39 Claims, No Drawings

OTHER PUBLICATIONS

Lieberman, "The Use of the Disproportion of Esters of 2–Propanenitronic Acid to Convert Halides to Carbonyl Compounds and Benzaldehyde to Benzamides", *J. Am. Chem. Soc.* 77, 1955, pp. 1114–1116.

Moelm et al. "Fragmentation Reactions of Quaternized γ–Amino Alcohols–Diastereoselective Synthesis of Highly Functionalized Oxetanes and Unsaturated Aldehydes and Ketones with a (Z)–C–C Double Bond" *Eur. J. Org. Chem* 10:2185–2191 (1998) XP000993116.

3-AMIN3-ARYLPROPAN-1-OL COMPOUNDS, THEIR PREPARATION AND USE

BACKGROUND OF THE INVENTION

The present invention relates to substituted 3-amino-3-arylpropan-1-ols of the general formula I,

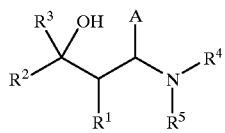

wherein
- $R^1$, $R^2$ denote, in each case independently of one another, $C_{1-6}$ alkyl or $R^1$ and $R^2$ together denote a $(CH_2)_{2-6}$ ring that may also be substituted by phenyl,
- $R^3$ denotes $C_{3-6}$ alkyl, $C_{3-6}$ cycloalkyl, aryl with optionally heteroatoms in the ring system and the substituents $R^6$ to $R^8$ on the aryl ring, or a substituted $C_{1-3}$ alkylphenyl of the formula XII,

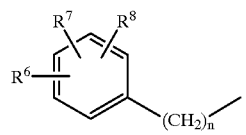

wherein
- n=1, 2 or 3
- $R^4$, $R^5$ denote, in each case independently of one another, $C_{1-6}$ alkyl, $C_{3-6}$ cycloalkyl, phenyl, benzyl, phenethyl or $R^4$ and $R^5$ together form a $(CH_2)_{3-6}$ ring or $CH_2CH_2OCH_2CH_2$ ring,
- $R^6$ to $R^8$ denote, in each case independently of one another, H, F, Cl, Br, $CHF_2$, $CF_3$, OH, $OCF_3$, $OR^{14}$, $NR^{15}R^{16}$, $SR^{14}$, phenyl, $SO_2CH_3$, $SO_2CF_3$, $C_{1-6}$ alkyl, CN, $COOR^{14}$, $CONR^{15}R^{16}$ or $R^6$ and $R^7$ together form a $OCH_2O$, $OCH_2CH_2O$, $CH=CHO$, $CH=C(CH_3)O$ or $(CH_2)$ ring, wherein
- $R^{14}$ denotes $C_{1-6}$ alkyl, phenyl, benzyl, phenethyl and
- $R^{15}$, $R^{16}$ denote, in each case independently of one another, H, C1–6 alkyl, phenyl, benzyl, phenethyl, and
- A denotes an aryl radical that may optionally contain heteroatoms in the ring system and/or that may optionally be substituted,
- and their diastereomers or enantiomers in the form of their bases or salts of physiologically compatible acids, whereas 1-benzyl-2-(dimethylaminophenylmethyl)cyclohexanol, its diastereomers and its enantiomers in the form of their bases and its reaction product with methyliodide are disclaimed, as well as their preparation and use as medicinal drugs.

The treatment of chronic and non-chronic painful states is extremely important in medicine since pain is one of the basic symptoms encountered in clinical practice. At the present time there is a worldwide demand for additional, not exclusively opioid, but highly effective pain treatments.

The urgent need for a patient-friendly and targeted treatment of chronic and non-chronic painful states, by which is meant the successful and satisfactory management of pain for the patient, is documented in the large number of scientific articles that have recently appeared in the field of applied analgesics and fundamental research in nociception.

Conventional opioids such as for example morphine are extremely effective in treating severe to extremely severe pain. Their use is limited however by the known side effects, for example respiratory depression, vomiting, sedation, constipation, addiction, dependence and development of tolerance. Accordingly they can be administered over a prolonged period or in relatively high doses only if particular safety precautions, for example special regulatory provisions, are observed (Goodman, Gilman, The Pharmacological Basis of Therapeutics, Pergamon Press, New York, 1990). Furthermore, they are less effective in some painful states, in particular in the case of neuropathic pain.

SUMMARY OF THE INVENTION

The object forming the basis of the present invention is to provide a new structural class of analgesically effective substances that are suitable for treating pain. Further objects of the invention are to provide active agents that are also suitable for use as a local anaesthetic and/or anti-arrythmic and/or anti-emetic and/or nootropic (neurotropic) and/or for the treatment/therapy of cardiovascular conditions and/or urinary incontinence and/or diarrhoea and/or pruritus and/or alcohol and/or narcotics and/or drug dependence and/or inflammation. As a rule the substances are also suitable for treating depression and/or for improving alertness and attentiveness, and/or improving libido.

It has now been found that the class of compounds of the general formula I is characterized by a pronounced analgesic action. Furthermore the compounds of the general formula I exhibit a marked affinity for the binding site 2 of the sodium channel (BTX binding), for the benzothiazepine and the phenylalkylamine binding site of the L-type calcium channel (diltiazem and verapamil binding), and inhibit synaptosomal noradrenaline uptake (NA uptake inhibition). Accordingly the class of compounds of the general formula I is also suitable for use as a local anaesthetic and/or anti-arrythmic and/or anti-emetic and/or nootropic (neurotropic) and/or for the treatment/therapy of cardiovascular conditions and/or urinary incontinence and/or diarrhoea and/or pruritus and/or alcohol and/or narcotics and/or drug dependence, and/or inflammation. As a rule the class of compounds of the general formula I is also suitable for improving alertness and attentiveness and/or improving libido and/or for treating depression.

The invention thus relates to substituted 3-amino-3-arylpropan-1-ols of the general formula I,

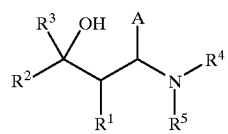

wherein the radicals $R^1$ to $R^5$ and A have the meanings given above,
  and the corresponding diastereomers or enantiomers in the form of their bases or salts of physiologically compatible acids,
  whereas 1-benzyl-2-(dimethylaminophenylmethyl) cyclohexanol, its diastereomers and its enantiomers in the form of their bases and its reaction product with methyliodide are disclaimed.

Preferred are compounds of the general formula I in which $R^1$ and $R^2$ together form a $(CH_2)_{2-6}$ ring, in particular a $(CH_2)_4$ ring, which is optionally substituted by phenyl, $R^3$ to $R^5$ and A have the meanings according to the definition of the general formula I, or compounds of the general formula I in which $R^3$ denotes a substituted $C_{1-3}$ alkylphenyl of the formula XII, $R^1$, $R^2$, $R^4$ and $R^5$ and A have the meanings according to the definition of the general formula I, or compounds of the general formula I in which $R^3$ denotes an aryl radical with optionally heteroatoms in the ring system and the substituents $R^6$ to $R^8$ on the aryl ring, $R^1$, $R^2$, $R^4$ and $R^5$ and A have the meanings according to the definition of the general formula I, or compounds of the general formula I in which A denotes a radical from the group of substituted phenyl of the formula XI

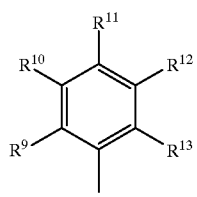

XI wherein
$R^9$ to $R^{13}$ denote, in each case independently of one another, H, F, Cl, Br, I, $CF_3$, OH, $OR^{14}$, $OCF_3$, $SR_{14}$, $SO_2CH_3$, $SO_2CF_3$, $C_{1-6}$ alkyl, phenyl, CN, $COOR^{14}$, $NO_2$ or $R^9$ and $R^{10}$ or $R^{10}$ and $R^{11}$ together form a $OCH_2O$ or $OCH_2CH_2O$ ring,
$R^{14}$ denotes $C_{1-6}$ alkyl, phenyl, benzyl, phenethyl
or A denotes an unsubstituted or substituted thiophene or an unsubstituted or substituted furan, and the radicals $R^1$ to $R^5$ have the meanings according to the definition of the general formula I.

Also preferred are compounds of the general formula I in which $R^1$ and $R^2$ together form a $(CH_2)_{2-6}$ ring, in particular a $(CH_2)_4$ ring, which is optionally substituted by phenyl, $R^3$ denotes a substituted $C_{1-3}$ alkylphenyl of the formula XII, $R^4$ to $R^5$ and A have the meanings according to the definition of the general formula I, or compounds of the general formula I in which $R^1$ and $R^2$ together form a $(CH_2)_{2-6}$ ring, in particular a $(CH_2)_4$ ring, which is optionally substituted by phenyl, $R^3$ denotes an aryl radical with optionally heteroatoms in the ring system and the substituents $R^6$ to $R^8$ on the aryl ring, and $R^4$ to $R^5$ and A have the meanings according to the definition of the general formula I, or compounds of the general formula I in which $R^1$ and $R^2$ together form a $(CH_2)_4$ ring, which is optionally substituted by phenyl, A denotes a radical from the group of substituted phenyl of the formula XI or unsubstituted or substituted thiophene or unsubstituted or substituted furan, $R^3$ denotes a substituted $C_{1-3}$ alkylphenyl of the formula XII, and $R^4$ to $R^5$ have the meanings according to the definition of the general formula I, or compounds of the general formula I in which $R^1$ and $R^2$ together form a $(CH_2)_4$ ring, which is optionally substituted by phenyl, A denotes a radical from the group of substituted phenyl of the formula XI or unsubstituted or substituted thiophene or unsubstituted or substituted furan, $R^3$ denotes an aryl radical with optionally heteroatoms in the ring system and the substituents $R^6$ to $R^8$ on the aryl ring, and $R^4$ to $R^5$ have the meanings according to the definition of the general formula I.

Also preferred are compounds of the general formula I in which $R^1$ and $R^2$ together form a $(CH_2)_4$ ring, A denotes unsubstituted or substituted thiophene, $R^3$ denotes a substituted $C_{1-3}$ alkylphenyl of the formula XII, and $R^4$ to $R^5$ have the meanings according to the definition of the general formula I, or compounds of the general formula I in which $R^1$ and $R^2$ together form a $(CH_2)_4$ ring, A denotes unsubstituted or substituted thiophene, $R^3$ denotes an aryl radical with optionally heteroatoms in the ring system and the substituents $R^6$ to $R^8$ on the aryl ring, and $R^4$ to $R^5$ have the meanings according to the definition of the general formula I, or compounds of the general formula I in which R1 and R2 together form a $(CH_2)_4$ ring, A denotes unsubstituted or substituted furan, $R^3$ denotes a substituted $C_{1-3}$ alkylphenyl of the formula XII, and R4 to R5 have the meanings according to the definition of the general formula I.

Compounds of the general formula I in which $R^1$ and $R^2$ together form a $(CH_2)_4$ ring A denotes unsubstituted or substituted furan, $R^3$ denotes an aryl radical with optionally heteroatoms in the ring system and the substituents $R^6$ to $R^8$ on the aryl ring, and $R^4$ to $R^5$ have the meanings according to the definition of the general formula I.

Substituents on the substituted thiophene radicals or substituted furan radicals are preferably selected from the group consisting of $C_{1-6}$ alkyl, halogen (particularly preferably Br, Cl or F), OR, SR, aryl $SO_2R$, $NO_2$, CN and COOR, wherein R is $C_{1-6}$ alkyl. More than one substituent may be present on the substituted thiophene or furan radicals, but preferably the substituted thiophene and furan radicals are monosubstituted.

Further preferred compounds include:
2-(dimethylaminophenylmethyl)-1-(3-methoxyphenyl) cyclohexanol and the corresponding hydrochloride
2-(dimethylaminophenylmethyl)-1-(3-fluorophenyl) cyclohexanol and the corresponding hydrochloride
2-(dimethylaminophenylmethyl)-1-phenylcyclohexanol and the corresponding hydrochloride
3-[2-(dimethylaminophenylmethyl)-1-hydroxycyclohexyl]phenol and the corresponding hydrochloride
2-(dimethylaminophenylmethyl)-1-(4-methoxyphenyl) cyclohexanol and the corresponding hydrochloride
1-(4-chlorophenyl)-2-(dimethylaminophenylmethyl) cyclohexanol and the corresponding hydrochloride
2-(dimethylaminophenylmethyl)-1-(4-fluorophenyl) cyclohexanol and the corresponding hydrochloride
2-(dimethylaminophenylmethyl)-1-p-tolylcyclohexanol and the corresponding hydrochloride
1-(3-chlorophenyl)-2-[dimethylamino-(3-methoxyphenyl)-methyl]cyclohexanol and the corresponding hydrochloride
1-(4-dimethylaminophenyl)-2-(dimethylaminophenylmethyl)cyclohexanol and the corresponding hydrochloride
1-benzo[1,3]dioxol-4-yl-2-(dimethylaminophenylmethyl)-cyclohexanol and the corresponding hydrochloride
1-(3,4-dimethoxyphenyl)-2-(dimethylaminophenylmethyl)-cyclohexanol and the corresponding hydrochloride
2-(dimethylaminophenylmethyl)-1-(3-methoxybenzyl)-cyclohexanol and the corresponding hydrochloride 1-benzyl-2-(dimethylaminophenylmethyl)cyclohexanol, hydrochloride 2-(dimethylaminophenylmethyl)-1-(4-fluoro-3-trifluoromethylphenyl)cyclohexanol and the corresponding hydrochloride 2-(dimethylaminophenylmethyl)-1-(4-trifluoromethoxybenzyl)cyclohexanol and the corresponding hydrochloride 2-(dimethylaminophenylmethyl)-1-furan-3-ylcyclolexanol and the corresponding hydrochloride 1-butyl-2-(dimethylaminophenylmethyl)cyclohexanol and the corresponding hydrochloride 1-(3,4-dichlorophenyl)-2-(dimethylaminophenylmethyl)-cyclohexanol and the corresponding hydrochloride (+)-1-(3,4-dichlorophenyl)-2-(dimethylaminophenylmethyl)cyclohexanol and the corresponding hydrochloride (−)-1-(3,4-dichlorophenyl)-2-(dimethylaminophenylmethyl)cyclohexanol and the corresponding hydrochloride 4-[2-(dimethylaminophenylmethyl)-1-hydroxycyclohexyl]-phenol and the corresponding hydrochloride 2-(dimethylaminophenylmethyl)-1-naphthalene-2-ylcyclohexanol] and the corresponding hydrochloride 2-[dimethylamino-(4-trifluoromethylphenyl)methyl]-1-(3-methoxybenzyl)cyclohexanol and the corresponding hydrochloride 1-(4-chlorobenzyl)-2-(dimethylaminophenylmethyl)-1-cyclohexanol and the corresponding hydrochloride 2-(dimethylaminophenylmethyl)-1-(2-fluorobenzyl)cyclohexanol and the corresponding hydrochloride 2-(dimethylaminophenylmethyl)-1-(4-fluorobenzyl)cyclohexanol and the corresponding hydrochloride 1-(2,5-dimethoxyphenyl)-2-(dimethylaminophenylmethyl)-cyclohexanol and the corresponding hydrochloride 1-(2-chloro-4-fluorobenzyl)-2-(dimethylaminophenylmethyl)cyclolhexanol and the corresponding hydrochloride 1-(4-tert.-butylbenzyl)-2-(dimethylaminophenylmethyl)-cyclohexanol and the corresponding hydrochloride 2-(dimethylaminophenylmethyl)-1-(3-fluorobenzyl)cyclohexanol and the corresponding hydrochloride 1-(2-chlorobenzyl)-2-(dimethylaminophenylmethyl)cyclohexanol and the corresponding hydrochloride 1-benzo[1,3]dioxol-5-yl-2-[dimethylamino(3-methoxyphenyl)methyl]cyclohexanol and the corresponding hydrochloride 1-(3-chlorobenzyl)-2-(dimethylaminophenylmethyl)cyclohexanol and the corresponding hydrochloride 1-(2,4-dichlorobenzyl)-2-(dimethylaminophenylmethyl)-cyclohexanol and the corresponding hydrochloride 1-benzyl-2-[dimethylaminophenyl-(3-phenoxyphenyl)-methyl]cyclohexanol and the corresponding hydrochloride 1-benzyl-2-[dimethylaminophenyl-(3-methoxyphenyl)-methyl]cyclohexanol and the corresponding hydrochloride 2-(dimethylaminophenylmethyl)-1-(3-trifluoromethylbenzyl)cyclohexanol and the corresponding hydrochloride 2-(dimethylamino-(3-methoxyphenyl)methyl]-1-(3-methoxybenzyl)cyclohexanol and the corresponding hydrochloride 2-[(2-chlorophenyl)dimethylaminomethyl]-1-naphthalene-2-ylcyclohexanol and the corresponding hydrochloride 1-benzyl-2-[(3,4-dichlorophenyl)dimethylaminomethyl]-cyclohexanol and the corresponding hydrochloride 2-[(3,4-dichlorophenyl)(dimethylaminomethyl]-1-phenethyl-cyclohexanol and the corresponding hydrochloride 1-benzyl-2-[dimethylamino-(4-fluorophenyl)methyl]cyclohexanol and the corresponding hydrochloride 2-[(3-chlorophenyl)(dimethylaminomethyl]-1-phenyl-cyclohexanol and the corresponding hydrochloride 1-(2,4-dichlorophenyl)-2-(3-dimethylaminomethyl)-1-cyclohexanol and the corresponding hydrochloride 1-benzyl-2-[(3-chlorophenyl)dimethylaminomethyl] cyclohexanol and the corresponding hydrochloride 1-benzyl-2-[(2-chlorophenyl)dimethylaminomethyl] cyclohexanol and the corresponding hydrochloride 1-(4-tert.-butylbenzyl)-2-[(3,4-dichlorophenyl) dimethylaminometlhyl)cyclohexanol and the corresponding hydrochloride 2-[dimethylamino-(4-fluorophenyl)methyl]-1-(3-trifluoromethylbenzyl)cyclohexanol and the corresponding hydrochloride 2-(dimethylaminophenylmethyl)bicyclohexyl-1-ol and the corresponding hydrochloride 2-(dimethylaminophenylmethyl)-1-(4-methoxybenzyl)-cyclohexanol and the corresponding hydrochloride 1-(2,4-difluorobenzyl)-2-(dimethylaminophenylmethyl)-cyclohexanol and the corresponding hydrochloride 1-(4-tert.-butylbenzyl)-2-[(3-chlorophenyl) dimethylaminomethyl]cyclohexanol and the corresponding hydrochloride 2-[dimethylamino-(3-phenoxyphenyl)methyl]-1-phenethyl-cyclohexanol and the corresponding hydrochloride 2-[dimethylamino-(3-phenoxyphenyl)methyl]-1-(3-trifluoromethylbenzyl)cyclohexanol and the corresponding hydrochloride 1-(2,5-difluorobenzyl)-2-(dimethylaminophenylmethyl) cyclohexanol and the corresponding hydrochloride 1-(3,4-difluorobenzyl)-2-(dimethylaminophenylmethyl) cyclohexanol and the corresponding hydrochloride 1-(2-chloro-6-fluorobenzyl)-2-(dimethylaminophenylmethyl)cyclohexanol and the corresponding hydrochloride 1-(2,3-difluorobenzyl)-2-(dimethylaminophenylmethyl) cyclohexanol and the corresponding hydrochloride 1-benzyl-2-[(4-chlorophenyl)dimethylaminomethyl] cyclohexanol and the corresponding hydrochloride 1-dimethylamino-3-ethyl-2-methyl-1,5-diphenylpentane-3-ol and the corresponding hydrochloride 1-(2-chlorobenzyl)-2-[(2-chlorophenyl)-dimethylaminomethyl]cyclohexanol and the corresponding hydrochloride 1-benzyl-2-[(4-bromophenyl)dimethylaminomethyl] cyclohexanol and the corresponding hydrochloride 2-[(4-chlorophenyl)dimethylaminomethyl]-1-(4-trifluoromethylphenyl)cyclohexanol and the corresponding hydrochloride 2-[(4-chlorophenyl)dimethylaminomethyl]-1-(3-trifluoromethylbenzyl)cyclohexanol and the corresponding hydrochloride 1-(4-tert.-butylbenzyl)-2-[dimethylamino-(3-phenoxyphenyl)methyl]cyclohexanol and the corresponding hydrochloride 4-{dimethylamino-[2-hydroxy-2-(4-trifluoromethylphenyl)cyclohexyl]methyl}benzonitryl and the corresponding hydrochloride 2-(dimethylamino-o-tolylmethyl)-1-phenylcyclohexanol and the corresponding hydrochloride 1-benzyl-2-(dimethylamino-o-tolylmethyl)cyclohexanol and the corresponding hydrochloride 2-(dimethylaminophenylmethyl)-1-(3-phenylpropyl)cyclohexanol and the corresponding hydrochloride 2-[(2-chlorophenyl)dimethylaminomethyl]-1-[2-(4-fluorophenyl)ethyl]cyclohexanol and the corresponding hydrochloride 2-dimethylaminothiophene-2-ylmethyl]-1-(3-trifluoromethylbenzyl)cyclolhexanol and the corresponding hydrochloride Methyl-4-[2-(dimethylaminophenylmethyl)-1-hydroxycyclohexyl]benzoate and the corresponding hydrochloride 1-benzyl-2-(dimethylaminophenylmethyl)-4-phenylcyclhexanol and the corresponding hydrochloride 1-(4-bromophenyl)-2-(dimethylaminophenylmethyl)cyclohexanol and the corresponding hydrochloride 2-(dimethylaminophenylmethyl)-1-naphthalene-1-ylcyclohexanol and the corresponding hydrochloride 2-(dimethylaminophenylmethyl)-1-(2-methylsulfanylphenyl)cyclohexanol and the corresponding hydrochloride 1-benzyl-2-(dimethylaminonaphthalene-2-ylmethyl)cyclohexanol and the corresponding hydrochloride 1-benzyl-2-(dimethylaminonapentafluorophenylmethyl)cyclohexanol and the corresponding hydrochloride 1-benzyl-2-(phenylpiperidin-1-ylmethyl)cyclolhexanol and the corresponding hydrochloride 2-(dimethylaminophenylmethyl)-1-(4-trifluoromethylphenyl)cyclohexanol and the corresponding hydrochloride 3-(4-tert.-butylbenzyl)-1-dimethylamino-2-methyl-1-phenylpentan-3-ol and the corresponding hydrochloride 2-(dimethylamino-o-tolylmethyl)-1-phenethylcyclohexanol and the corresponding hydrochloride 1-(4-tert.-butylbenzyl)-2-[dimethylaminothiophen-2-ylmethyl]cyclohexanol and the corresponding hydrochloride Compounds according to the invention are also compounds of the general formula I as diastereomers or enantiomers in the form of their bases or salts of physiologically compatible acids.

In a special embodiment of the invention the compounds according to the invention including the disclaimed compounds are used as a mixture of the enantiomers in non-equimolar amounts as active agent in a medicinal drug, optionally together with further active agents. In this case the proportion of one enantiomer is preferably between 5 and 45 wt. %.

The expression "$C_{1-6}$ alkyl" denotes within the scope of the present invention straight-chain or branched hydrocarbons with 1 to 6 carbon atoms. Methyl, ethyl, propyl, isopropyl, n-butyl, sec.-butyl, tert.-butyl, n-pentyl, neopentyl and n-hexyl may be mentioned by way of example.

The expression "$C_{3-7}$ cycloalkyl" denotes within the scope of the present invention saturated cyclic hydrocarbons or straight-chain or branched alkyl radicals that contain saturated cyclic hydrocarbons, with a total of 3 to 7 carbon atoms. Cyclopropyl, cyclopropylmethyl, methylcyclopropyl, cyclobutyl, 1-cyclopropylethyl, 2-cyclopropylethyl, cyclopentyl, cyclopentylmethyl, cyclohexyl or cycloheptyl may be mentioned by way of example.

The expression "aryl" denotes within the scope of the present invention preferably aromatic ring systems, optionally singly or multiply substituted, which may optionally contain heteroatoms in the ring system. The aryl radicals are preferably singly or multiply substituted by the radicals $R^9$ to $R^{13}$. The preferably 5-membered or 6-membered unsaturated heterocyclic compounds, optionally condensed with further rings, optionally singly or multiply substituted may contain one or two heteroatoms such as nitrogen, oxygen and/or sulfur in the ring system.

There may be mentioned by way of example from the group of heteroaryl compounds: furan, thiophene, pyrrole, pyridine, pyrimidine, quinoline, isoquinoline, phthalazine or quinazoline.

Furthermore, processes for preparing the compound of the general formula I are also an object of the invention.

These processes for producing the compounds of the general formula I with the exception of 1-benzyl-2-(dimethylaminophenylmethyl)-cyclohexanol, its diastereomers and its enantiomers are characterised in that Mannich bases of the formula II are reacted with suitable nucleophilic compounds, preferably organometallic compounds $R^3Y$ in which Y denotes MgCl, MgBr, MgI or Li, at temperatures between −70° C. and +110° C.

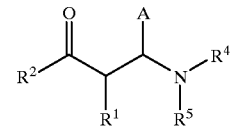

II

The conversion of a Mannich base of the formula II with a Grignard compound $R^3Y$ in which Y denotes MgCl, MgBr or MgI, or with an organolithium compound $R^3Li$, may be carried out in an aliphatic ether, for example diethyl ether and/or tetrahydrofuran, a hydrocarbon, for example hexane or toluene, or mixtures of hydrocarbons and aliphatic ethers, at temperatures between −70° C. and +110° C. The preparation of a Grignard compound $R^3Y$ may be carried out with or without the addition of an entrainment reagent, preferably 1,2-dibromomethane. Alternatively, aromatic Grignard compounds $R^3Y$ may be obtained by reacting an aromatic iodide $R^3I$ with an organomagnesium compound, for example isopropylmagnesium chloride or diisopropylmagnesium, by iodine-magnesium exchange. organolithium compounds $R^3Li$ can be obtained from organohalogen compounds $R^3Z$, in which Z denotes Cl, Br or I, by reaction with for example a n-butyllithium/liexane solution by halogen-lithium exchange.

In the reaction of a Manriich base of the formula II with an organometallic compound $R^3Y$, depending on the reaction conditions preferably tertiary alcohols having the relative configuration of the formula Ia are obtained, in which the aminoarylmethyl group is arranged in the cis position relative to the hydroxl group when $R^1$ and $R^2$ form a ring system. In open-chain systems the analogous relative stereochemistry is obtained, which is specified as anti. The compounds of the general formula I, as well as their salts, for example the hydrochlorides, can be obtained in a diastereomer pure form by column chromatographic separation or by crystallisation.

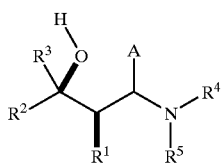

Ia

The Mannich bases of the formula II can be obtained by reacting enamines of the formula III with an imminium salt of the formula IV, in which Y denotes for example Cl⁻, AlCl$_4^-$, Br⁻ or I⁻.

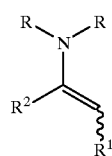

III

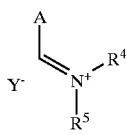

IV

The enamines are prepared by processes known in the literature from ketones of the formula V arid secondary amines, for example dimethylamine, pyrrolidine, piperidine or morpholine (Acta Chem. Scand. B 38 (1984) 49–53). The imminium salts are prepared by processes known in the literature by reacting aminals of the formula VI with acid chlorides, for example acetyl chloride or thionyl chloride (Houben-Weyl—Methoden der Organischen Chemie, E21b (1995) 1925–1929).

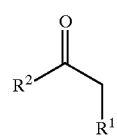

V

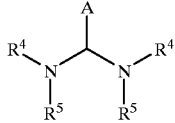

VI

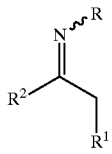

VII

The imminium salts of the formula IV need not be separated, but can be produced in situ and reacted with enamines of the formula III to form Mannich bases of the formula II (Agnew. Chem. 106 (1994) 2531–2533). On account of the enamine-imine tautomerism, which is similar to the keto-enol tautomerism, imines of the formula VII may also be used instead of the enamines of the formula III. Alternatively, ketones of the formula V can also be reacted directly with imminium salts of the formula IV.

Mannich bases of the formula II may however alos be prepared directly be reacting enamines of the formula III with an aromatic aldehyde of the formula VIII and a secondary amine HNR$^4$R$^5$, which may also be in the formula of the corresponding hydrochloride HNR$^4$R$^5$, HCl, in the presence of triethylamine, chlorotrimethylsilane and sodium iodide (Synlett (1997) 974–976).

VIII

Depending on the reaction conditions, the Mannich bases of the formula II prepared by the aforedescribed processes are preferably obtained having the relative configuration of the formula IIa, in which the amino group is arranged anti to R$^1$. The compounds of the formula IIa, as well as their salts, for example the hydrochlorides, can be obtained in a diastereomter pure form by crystallisation or by chromatographic separation.

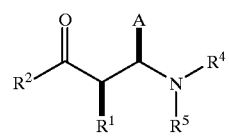

IIa

The formulation of Mannich bases of the formula II by 1,4-addition of secondary amines of the formula X to enones of the formula IX, which are obtained by the aldol condensation of ketones of the formula V with aromatic aldehydes of the formula VIII, proceeds in a less stereo-selective manner however (U.S. Pat. No. 4,017,637). This procedure is accordingly suitable for preparing the other possible stereoisomters.

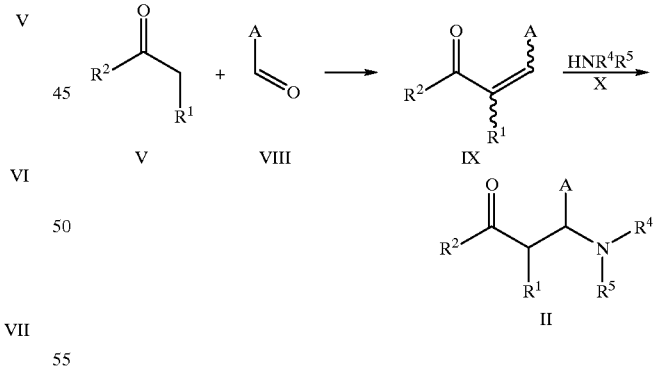

If chiral amines are used to prepare enamines of the formula III or imines of the formula VII, then enantiomer-enriched to enantiomer-pure Mannich bases of the formula II may be obtained in the following Mannich reaction (Houben-Weyl—Methoden der Organischen Chemie, E21b (1995) 1925–1929). 3-amino-3-arylpropan-1-ol compounds of the general formula I in which R$^3$ contains a phenolic substituent can be prepared for example from the corresponding methyl ether derivatives with diisobutylaluminium hydride in an aromatic hydrocarbon, for example toluene, at a temperature between 60° C. and 130° C. (Synthesis (1975) 617–630).

The compounds of the formula I can be converted in a manner known per se into their salts with physiologically compatible acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. The salt formulation is preferably carried out in a solvent, for example diethyl ether, diisopropyl ether, alkyl acetates, acetone and/or 2-butanone. Moreover, trimethylchlorosilane in aqueous solution is suitable for preparing the hydrochlorides.

The substances corresponding to formula I are toxicologically safe, which means that they can be used as a pharmaceutical active agent in medicinal drugs. A further object of the invention are accordingly medicinal drugs containing as active agent at least one compound of the general formula I. The medicinal drugs according to the invention are preferably used as analgesics.

Biochemical investigation has shown that the substances according to the general formula I, in addition to their analgesic action, a pronounced affinity for the binding site 2 of the sodium channel (BTX binding), or the benzothiazepine and phenylalkylamine binding site of the L-type calcium channel (diltiazem and verapamil binding) and inhibit synaptosomal noradrenaline uptake (NA uptake inhibition). In addition to their particularly preferred use in the treatment of pain, the substances according to the general formula I are therefore also suitable for use as a local anaesthetic and/or anti-arrytlimic and/or anti-emetic and/or nootropic (neurotropic) and/or for the treatment/therapy of cardiovascular conditions and/or urinary incontinence and/or diarrhoea and/or pruritis and/or alcohol and/or narcotics and/or drug dependence and/or inflammation. As a rule the substances according to the invention are also suitable for treating depression and/or for improving alertness and attentiveness, and/or improving libido.

The analgesics according to the invention contain, in addition to at least one 3-amino-3-arylpropan-1-ol derivative of the formula I, excipients, fillers, solvents, diluents, dyes and/or binders. The choice of auxiliary substances as well as the amounts thereof to be used depends on whether the medicinal drug is to be administered orally, intravenously, intraperitoneally, intradermally, intramuscularly, intranasally, buccally or topically, for example to treat skin infections, eye infections or infections of the mucous membranes. For oral application suitable preparations are in the form of tablets, sugar-coated pills, capsules, granular powders, drops, juices and syrups, while for parenteral, topical and inhalative application suitable forms are solutions, suspensions, easily reconstitutable dry preparations as well as sprays. Compounds according to the invention of the formula I in a sustained-release substance, in dissolved form or in a plaster, optionally with the addition of agents promoting penetration of the skin, are suitable percutaneous application preparations. Forms of preparations that can be used orally or percutaneously may produce a delayed release of the compounds according to the invention of formula I.

The amount of active agent to be administered to the patient depends on the patient's weight, on the type of application, symptoms and the severity of the illness. Normally 0.5 to 500 mg/kg of at least one 3-amino-3-arylpropan-1-ol derivative of the formula I are administered.

Pharmacological Investigations

Analgesic Effect in the Writing Test in Mice

The analgesic effect was investigated in the phenylquinone-induced writhing test in mice (as modified by I. C. Hendershot and J. Forsaith (1959) J. Pharmacol. Exp. Ther. 125, 237–240). Male NMRI mice weighing 25 to 30 g were used for the test. Groups of 10 animals each received by intraperitoineal application, for each substance dose, 0.3 ml/mouse of a 0.02% aqueous solution of phenylquinone (phenylbenzoquinone, Sigma Company, Deisenhofen; solution prepared with addition of 5% of ethanol and kept in a water bath at 45° C.) 10 minutes after intravenous administration of the test substances. The animals were placed individually in observation cages. The number of pain-induced stretching movements (so-called writhing reactions=straightening of the body together with stretching of the rear extremities) was measured by means of a push-button counter 5 to 20 minutes after administration of the phenylquinone. Animals that had received only physiological saline solution served as controls. All substances were tested in the standard dose of 10 mg/kg. The percentage inhibition (% inhibition) of the writhing reaction produced by a substance was calculated according to the following formula:

$$\% \text{ inhibition} = 100 - \frac{\text{writhing reactions of the treated animals}}{\text{writhing reactions of the control animals}} \times 100$$

For some substances the $ED_{50}$ values were calculated with 95% confidence range of the writhing reaction by means of regression analysis (evaluation program from Martens EDV Service, Eckental) from the dose-dependent reduction in the writhing reactions compared to phenylquinone control groups investigated in parallel.

All the compounds according to the invention that were investigated exhibited a pronounced analgesic effect. The results are summarised in Table 1.

TABLE 1

(Part ½): Analgesia Examination in the Writhing Test in Mice

| Example | % Inhibition of the writhing reaction at 10 mg/kg intravenously | Example | % Inhibition of the writhing reaction at 10 mg/kg intravenously |
|---|---|---|---|
| 1 | 85 | 29 | 96 |
| 2 | 88 | 30 | 85 |
| 3 | 83 | 31 | 76 |
| 4 | 75 | 32 | 100 |
| 5 | 100 | 33 | 84 |
| 6 | 83 | 34 | 99 |
| 7 | 85 | 35 | 81 |
| 8 | 81 | 36 | 100 |
| 9 | 73 | 37 | 93 |
| 10 | 97 | 38 | 85 |
| 11 | 99 | 39 | 94 |
| 12 | 95 | 40 | 72 |
| 13 | 100 | 41 | 88 |
| 14 | 70 | 42 | 76 |
| 15 | 73 | 43 | 80 |
| 16 | 75 | 44 | 100 |
| 17 | 100 | 45 | 82 |
| 18 | 100 | 46 | 68 |
| +19 | 74 | 47 | 89 |
| −19 | 88 | 48 | 94 |
| 20 | 96 | 49 | 100 |
| 21 | 97 | 50 | 85 |
| 22 | 68 | 51 | 99 |
| 23 | 100 | 52 | 70 |
| 24 | 97 | 53 | 90 |
| 25 | 100 | 54 | 98 |

TABLE 1-continued (Part ½): Analgesia Examination in the Writhing Test in Mice

| Example | % Inhibition of the writhing reaction at 10 mg/kg intravenously | Example | % Inhibition of the writhing reaction at 10 mg/kg intravenously |
|---|---|---|---|
| 26 | 94 | 55 | 92 |
| 27 | 82 | 56 | 94 |
| 28 | 100 | 57 | 84 |

TABLE 1

(Part ⅔): Analgesia Examination in the Writhing Test in Mice

| Example | % Inhibition of the writhing reaction at 10 mg/kg intravenously |
|---|---|
| 58 | 98 |
| 59 | 59 |
| 60 | 63 |
| 61 | 90 |
| 62 | 94 |
| 63 | 86 |
| 64 | 88 |
| 65 | 76 |
| 66 | 91 |
| 67 | 84 |
| 68 | 55 |
| 69 | 45 |
| 70 | 98 |
| 71 | 55 |
| 72 | 89 |
| 73 | 75 |
| 74 | 37 |
| 75 | 57 |
| 76 | 60 |
| 77 | 54 |
| 78 | 73 |
| 79 | 71 |
| 80 | 61 |
| 81 | 75 |
| 82 | 100 |

Biochemical Investigations

Investigations on the Noradrenaline Uptake Inhibition (NA Uptake Inhibition)

In order to carry out these in vitro studies, synaptosomes are isolated fresh from rat brains. In each case a so-called "$P_2$" fraction is used, which is prepared according to the protocol of Gray and Whittaker (E. G. Gray and V. P. Whittaker (1962) J. Anat. 76, 79–88). For the NA uptake these vesicular particles are isolated from the hypothalamus of male rat brains.

The following characteristic data were determined for the NA transporter:

NA uptake: Km=0.32±0.11 $\mu$M (in each case N=4, i.e. mean values±SEM from 4 independent series of experiments that were carried out in the form of triple parallel experiments).

A detailed description of the methodology can be found in the literature (M. Ch. Frink, H.-H. Hennies, W. Englberger, M. Haurand and B Wilffert (1996) Arzneim.-Forsch./Drug Res. 46 (III), 11, 1029–1036).

Binding Investigations in the L Calcium Channel Benzothiazepine Binding Site (Diltiazem Binding)

The biological membrane material was isolated from the rat cerebral cortex. [$^3$H]-cis-(+)-diltiazem (5 nM in the assay) was used as ligand. The material was incubated for 20 minutes at 25° C. The radioactivity that is measured in the presence of (±)-diltiazem ($10^{-6}$ M in the assay) is defined as non-specific binding. After completion of incubation the non-bound fraction of the radioactive ligand is separated by means of a filtration process using Whatman Glasfiber GF/B membranes. The membranes are washed and the radioactivity is then measured using a $\beta$-counter. The method is based on the details published by Schoemaker and Langer (H. Schoemaker and S. Z. Langer (1985) Eur. J. Pharmacol. 111, 273–277). The $K_D$ value for this high-affinity binding site was 4.10±0.75 nM (N=3, i.e. mean values±SEM from 3 independent series of experiments that had been carried out in triple parallel experiments).

Phenylalkylamine Binding Site (Verapamil Binding)

The biological material (ion channel particles) was prepared on the basis of the publication of Reynolds, Gould and Snyder (I. J. Reynolds, R. J. Gould and S. H. Snyder (1983) J. Pharmacol. 95, 319–321).

N-methyl-[$^3$H]-verapamil (2 nM in the assay) was used as radioligand. The radioactivity that is measured in the presence of non-radioactive verapamil ($10^{-4}$ M in the assay) is defined as non-specific binding. The material was incubated at 25° C. for 45 minutes. The material was then filtered using a Whatman GF/B filter, followed by washing. The radioactivity remaining on the filter (ion channel binding) was measured using a $\beta$-counter.

The $K_D$ value for this binding site was found to be 138.6 nM (N=2, i.e. mean values from 2 independent series of experiments that had been carried out in the form of triple parallel experiments).

Binding Investigations in the Sodium Channel Binding Site 2 (BTX Binding)

The binding site 2 of the sodium channel is the so-called batrachotoxin (BTX) binding site. [$^3$H]-batrachlotoxin A20 $\alpha$-benzoate (10 nM in the assay) was used as ligand. These ion channel particles (synaptosomes) were concentrated from rat cerebral cortex according to the procedure of Gray and Whittaker (E. G. Gray and V. P. Whittaker (1962) J. Anat. 76, 79–88). The radioactivity that is measured in the presence of veratridine (0.3 mM in the assay) is defined as non-specific binding. The material was incubated at 37° C. for 120 minutes. The assay conditions are carried out according to the protocol published by Pauwels, Leysen and Laduron (P. J. Pauwels, J. E. Leysen and P. M. Laduron (1986) Eur. J. Pharmacol. 124, 291–298).

The $K_D$ value for this binding site is 24.63±1.56 nM. (N=3, i.e. mean values±SEM from 3 independent series of experiments that were carried out in the form of triple parallel experiments).

Evaluation

In addition to the percentage inhibition of the test systems at fixed test substance concentrations (NA uptake: 1 $\mu$M in the assay; ion channel assays: 10 M in the assay), the dose dependencies were investigated. For this purpose $IC_{50}$ values are obtained, which can be converted to inhibitor constants ($K_i$) according to the "Cheng-Prusoff equation" (Y. C. Clieng and W. H. Prusoff (1973) Biochem. Pharmacol. 22, 3099–3108). The $IC_{50}$ values were obtained by means of the computer program "Figure P" (version 6.0, Biosoft, Cambridge, England). Km values were calculated according to Lineweaver and Burk (H. Lineweaver and D. Burk (1934) J. Am. Chem. Soc. 56, 658–666). The "Ligand" computer program (version 4, Biosoft, England) was used to obtain Ken values.

The results of the biochemical investigations are summarised in Table 2.

TABLE 2

(Part 1/3): Biochemistry

| Example | NA Uptake Inhibition at 1 μM | Verapamil Binding at 10 μM | Diltiazem Binding at 10 μM | BTX Binding at 10 μM |
|---|---|---|---|---|
| 1 | 41 | 76 | 65 | 77 |
| 2 | 52 | 76 | 52 | 80 |
| 3 | 41 | 68 | 50 | 78 |
| 4 | 49 | 57 | 46 | 70 |
| 5 | 70 | 56 | 54 | 97 |
| 6 | 51 | 60 | 96 | 90 |
| 7 | 38 | 56 | 78 | 86 |
| 8 | 50 | 56 | 68 | 88 |
| 9 | 62 | | 91 | 89 |
| 10 | 48 | 61 | 69 | 88 |
| 11 | 54 | 61 | 85 | 79 |
| 12 | 87 | 69 | 51 | 69 |
| 13 | 95 | | 88 | 94 |
| 14 | 100 | | 88 | 89 |
| 15 | 44 | 87 | 97 | 94 |
| 16 | 89 | 91 | 100 | 98 |
| 17 | 57 | 72 | 54 | 70 |
| 18 | 84 | 75 | 81 | 95 |
| 19 | 50 | 81 | | 97 |
| +19 | 62 | 82 | 85 | 92 |
| −19 | 36 | 83 | 85 | 96 |
| 20 | 68 | | 69 | 68 |
| 21 | 17 | 71 | 85 | 94 |
| 22 | 91 | 80 | 72 | 98 |
| 23 | 99 | | 100 | 94 |
| 24 | 98 | | 93 | 92 |
| 25 | 98 | | 85 | 91 |
| 26 | 5 | | 87 | 85 |
| 27 | 89 | | 96 | 97 |
| 28 | 63 | | 89 | 100 |

(Part 2/3): Biochemistry

| Example | NA Uptake Inhibition at 1 μM | Verapamil binding at 10 μM | Diltiazem binding at 10 μM | BTX binding at 10 μM |
|---|---|---|---|---|
| 29 | 96 | | 72 | 88 |
| 30 | 98 | | 98 | 96 |
| 31 | 43 | | 90 | 85 |
| 32 | 100 | | 98 | 94 |
| 33 | 83 | | 86 | 98 |
| 34 | 96 | | 100 | 100 |
| 35 | 100 | | 87 | 92 |
| 36 | 91 | | | 98 |
| 37 | 100 | | 94 | 90 |
| 38 | 17 | | 67 | 97 |
| 39 | 61 | | 76 | 97 |
| 40 | 58 | | 86 | 98 |
| 41 | 100 | | 87 | 94 |
| 42 | 82 | | 50 | 89 |
| 43 | 14 | | 73 | 94 |
| 44 | 99 | | 71 | 95 |
| 45 | 89 | | 67 | 96 |
| 46 | 35 | | 93 | 96 |
| 47 | 100 | | 84 | 100 |
| 48 | 29 | | 86 | 96 |
| 49 | 100 | | 93 | 90 |
| 50 | 100 | | 93 | 95 |
| 51 | 10 | | 77 | 99 |
| 52 | 38 | | 98 | 99 |
| 53 | 49 | | 92 | 97 |
| 54 | 96 | | 76 | 98 |
| 55 | 38 | | 76 | 94 |
| 56 | 92 | | 88 | 99 |
| 57 | 99 | | 83 | 97 |
| 58 | 0 | | 80 | 100 |

(Part 3/3): Biochemistry

| Example | NA Uptake Inhibition at 1 μM | Verapamil Binding at 10 μM | Diltiazem Binding at 10 μM | BTX Binding at 10 μM |
|---|---|---|---|---|
| 59 | 26 | | 64 | 86 |
| 60 | 56 | | 79 | 95 |
| 61 | 100 | | 89 | 98 |
| 62 | 80 | | 83 | 93 |
| 63 | 94 | | 95 | 99 |
| 64 | 36 | | 87 | 100 |
| 65 | 0 | | 72 | 78 |
| 66 | 15 | | 65 | 89 |
| 67 | 83 | | 98 | 97 |
| 68 | 49 | | 88 | 98 |
| 69 | 76 | | 93 | 96 |
| 70 | 74 | | 91 | 93 |
| 71 | 88 | | 74 | 81 |
| 72 | 64 | | 97 | 99 |
| 73 | 61 | | 89 | 93 |
| 74 | 24 | | 83 | 93 |
| 75 | 0 | | 89 | 93 |
| 76 | 80 | | 73 | 90 |
| 77 | 27 | | 27 | 56 |
| 78 | 84 | | 95 | 96 |
| 79 | 58 | | 67 | 93 |
| 80 | 18 | | 100 | 100 |
| 81 | 66 | | 83 | 99 |
| 82 | 0 | | 85 | 98 |

EXAMPLES

The following examples serve to illustrate the process according to the invention in more detail The yields of the prepared compounds are not optimised. All temperatures are uncorrected.

The term "ether" denotes diethyl ether.

Silica gel 60 (0.040–0.063 mm) from E. Merck, Darmstadt, was used as stationary phase for the column chromatography.

The thin-layer chromatography investigations were carried out with HPTLC ready prepared plates, silica gel 60 F 254, from E. Merck, Darmstadt.

The racemate separations were carried out on a Chiracel OD column 250×4.6 mm with a precolumn from Daicel.

The mixing ratios of the solvents for all chromatography investigations are in each case expressed in volume/volume.

RT denotes room temperature, vol. % denotes volume per cent, m % denotes wt. per cent and % ee denotes enantiomeric excess in per cent.

Example 1

2-(dimethlylaminophenylmethyl)-1-(3-methoxyphenyl)cyclohexanol, hydrochloride

1st Stage

Benzylidene dimethyl ammonium chloride 10 g (56 mmole) of N,N,N',N'-tetramethyl-C-phenylmethanediamine (J. Am. Chem. Soc. 77 (1955) 1114–1116) were dissolved in 100 ml of ether and cooled to 0° C. in an ice bath. 4.0 ml (56 mmole) of acetyl chloride were added under nitrogen. After the first few drops a white salt precipitated out and the temperature rose slightly. After 15 hours at RT the liquid was decanted off and the solids were washed three times, each time with 100 ml of ether, filtered under nitrogen through a protective gas frit, and dried to constant weight in an oil pump vacuum. 7.7 g of benzylidene dimethyl ammonium chloride (80.9% of theory) were obtained in this way.

2nd Stage 2-(dimethylaminophenylmethyl)cyclohexanone 7.1 ml (44 mmole) of 1-(pyrrolidino)-1-cyclohexene were dissolved in 45 ml of dichloromethane and cooled under nitrogen to −70° C. in a dry ice/isopropanol bath. 7.5 g (44 mmole) of benzylidene dimethyl ammonium chloride from Stage 1 were added while stirring, the mixture was heated to −30° C. within two to three hours, and then kept for 15 hours at this temperature. The mixture was worked up by adding 60 ml of semi-concentrated hydrochloric acid and stirring for 5 minutes. The mixture was washed at RT with 50 ml of ether, 440 ml of ammonia solution (25 vol. %) was added to the aqueous phase, and the latter was quickly extracted three times, each time with 150 ml of ether. The combined organic extracts were dried over sodium sulfate, filtered, and concentrated by evaporation on a rotary evaporator without heating (500 to 10 mbar). 10.1 g of crude base (99.5% of theory) were obtained in this way. 9.81 g (42.4 mmole) of the crude base were dissolved in 83 ml of 2-butatnone, and 0.76 ml (42.2 mmole) of water and 5.36 ml (42.4 mmole) of chlorotrimethylsilane were added in succession. The solution was kept for 15 hours at RT, and the precipitated solids were suction filtered, washed with small amounts of ether, and dried to constant weight in an oil pump vacuum. 8.92 g of the hydrochloride of 2-(dimethylaminophenylmethyl)cyclohexanone (78.6% of theory) were obtained in this way.

3rd Stage 2-(dimethylaminophenylmethyl)-1-(3-methoxyphenyl)cyclohexanol, hydrochloride 1.08 g (44.5 mmole) of magnesium turnings were stirred in 10 ml of tetrahydrofuran of analysis purity. 5.57 ml (44.5 mmole) of 3-bromoanisole dissolved in 40 ml of tetrahydrofuran were added dropwise so that the reaction mixture boiled gently. After completion of the addition the mixture was stirred for a further hour at RT. From 11 g (41.1 mmole) of the hydrochloride of 2-(dimethylaminophenylmethyl)cyclohexanone obtained after Stage 2, the base was released by adding 100 ml of water and 10 ml of caustic soda (32 m %), extracted three times, each time with 100 ml of ether, and the combined organic extracts were dried over sodium sulfate, filtered, and concentrated by evaporation on a rotary evaporator without heating (500 to 10 mbar). 8.57 g (37 mmole) of this base were dissolved in 10 ml of tetrahydrofuran, added dropwise to the Grignard reagent, and stirred for 15 hours at RT. The reaction mixture was worked up by adding dropwise 40 ml of saturated ammonium chloride solution while cooling in an ice bath, and extracted three times at RT with in each case 100 ml of ethyl acetate. The combined organic extracts were dried over sodium sulfate, filtered, and concentrated by evaporation on a rotary evaporator (500 to 10 mbar). 12.4 g of crude base (99.0% of theory) were obtained. The crude base was dissolved in 125 ml of 2-butanone, and 0.33 ml (18.3 mmole) of water and 4.63 ml (36.5 mmole) of chlorotrimethylsilanie were added in succession. The solution was kept for 15 hours at RT, and the precipitated solids were suction filtered, washed with small portions of ether and dried to constant weight in an oil pump vacuum. 8.27 g of 2-(dimethylaminophenylmethyl)-1-(3-methoxyphenyl)cyclohexanol, hydrochloride (59.4% of theory) with a melting point of 227°–229° C. were obtained in this way.

Example 2

2-(dimethylaminophenylmethyl)-1-(3-fluorophenyl)cyclohexaniol, hydrochloride 0.87 g (36.0 mmole) of magnesium turnings was stirred in 10 ml of ether of analysis purity. 4.02 ml (36.0 mmole) of 3-bromofluorobenzene dissolved in 30 ml of ether were added dropwise so that the reaction mixture boiled gently. After completion of the addition the mixture was stirred for a further hour at RT. 7.0 g (30 mmole) of the 2-(dimethylaminophenylmethyl)cyclohexanone prepared according to Example 1 were dissolved in 10 ml of ethers added dropwise to the Grignard reagent while cooling in an ice bath, and stirred for 15 hours at RT. The reaction solution was worked up by adding 40 ml of saturated ammonium chloride solution while cooling in an ice bath, and was extracted three times at RT with in each case 100 ml of ethyl acetate. The combined organic extracts were dried over sodium sulfate, filtered, and concentrated by evaporation on a rotary evaporator (500 to 10 mbar). 9.27 g of crude base (93.6% of theory) were obtained. 6.04 g of 2-(dimethylaminophenyl-methyl)-1-(3-fluorophenyl)cyclohexanol, hydrochloride (54.8% of theory) were obtained from the crude base according to Example 1 ($3^{rd}$ Stage) with chlorotrimethylsilane/water in 2-butanone. The hydrochloride decomposes when heated above 140° C.

Example 3

2-(dimethylaminophenylmethyl)-1-phenylcyclohexanol, hydrochloride 0.87 g (36.0 mmole) of magnesium turnings was stirred in 10 ml of ether of analysis purity. 3.8 ml (36.0 mmole) of bromobenzene dissolved in 30 ml of ether were added dropwise so that the reaction mixture boiled gently. After completion of the addition the reaction mixture was stirred for a further hour at RT. 7.0 g (30 mmole) of the 2-(dimethyl-aminophenylmethyl)cyclohexanone prepared according to Example 1 were dissolved in 10 ml of ether, added dropwise to the Grignard reagent while cooling in an ice bath, and stirred for 15 hours at RT. The reaction mixture was worked up by adding 40 ml of saturated ammonium chloride solution while cooling in an ice bath, and was extracted three times at RT with in each case 100 ml of ethyl acetate. The combined organic extracts were dried over sodium sulfate, filtered, and concentrated by evaporation on a rotary evaporator (500 to 10 mbar). 8.99 g of crude base (96.0% of theory) were obtained. 6.85 g of 2-(dimethylaminophenylmethyl)-1-phenyl-cyclo-hexanol, hydrochloride (65.4% of theory) were obtained from the crude base according to Example 1 ($3^{rd}$ stage) with chlorotrimethylsilane/water in 2-butanone. The hydrochloride decomposes when heated above 140° C.

Example 4

3-[2-(dimethylaminophenylmethyl)-1-hydroxycyclohexyl]phenol, hydrochloride $1^{st}$ Stage (3-bromophenoxy)trimethylsilane 23.4 g (0.145 mole) of hexamethylsilazane were added dropwise under nitrogen to 49.3 g (0.285 mole) of 3-bromophenol, and the solution was heated slowly to 150° C. and stirred for one hour until no more gas was produced. The solution was purified by distillation at 6 mbar, the main fraction boiling at 79° C. 66.7 g of (3-bromophenoxy)trimetlhylsilane (95.5's of theory) were obtained in this way.

$2^{nd}$ Stage

3-[2-(dimethylaminophenylmethyl)-1-hydroxycyclohexyl]phenol, hydrochloride 1.25 g (51.6 mmole) of magnesium turnings were stirred in 10 ml of ether of analysis purity. 12.7 g (51.6 mmole)of (3-bromophenoxy)trimethylsilane from stage 1, dissolved in 30 ml of ether, were added dropwise so that the reaction mixture boiled gently. After completion of the addition the reaction mixture was stirred for a further hour at RT. 10.0 g (43.0 mmole) of 2-(dimethylaminophenylmethyl) cyclohexanone prepared according to Example 1 were dissolved in 10 ml of ether, added dropwise to the Grignard reagent while cooling in an ice bath, and stirred for 15 hours at RT. The reaction mixture was worked up by adding 150 ml of hydrochloric acid (1 M), two phases being formed, one of which was an acetone-soluble oil. The aqueous phase and the acetone-soluble oil were adjusted with sodium bicarbonate to be slightly alkaline (pH ca. 8) and extracted three times at RT with in each case 100 ml of ethyl acetate. The combined organic extracts were dried over sodium sulfate, filtered, and concentrated by evaporation on a rotary evaporator (500 to 10 mbar). 7.51 g of crude base were obtained, which were added to a 5.5×50 cm column filled with silica gel. Elution with ethyl acetate/methanol (24:1) yielded 0.85 g of base, from which a hydrochloride was precipitated according to the procedure described in Example 1 ($3^{rd}$ stage) with chlorotrimethylsilane/water in 2-butanone. The base was released from the hydrochloride with 10 ml of water and sodium bicarbonate (pH ca. 8), extracted three times with in each case 30 ml of ether, and the combined organic extracts were dried over sodium sulfate, filtered and concentrated by evaporation on a rotary evaporator (500 to 10 mbar). The 670 mg of base that were obtained were added to a 3×17 cm column filled with silica gel. Elution with ethyl acetate/n-hexane (2:3) yielded 580 mg of base, from which 0.53 g of the 3-[2-(di-methylaminophenylmethyl)-1-hydroxycyclohexyl]phenol, hydrochloride (3.4% of theory) were obtained with 0.16 ml of hydrochloric acid (32 m %) and 5 ml of acetone. The hydrochloride decomposes on heating above 140° C.

Example 5

2-(dimethylaminophenylmethyl)-1-(4-methoxyphenyl)cyclohexanol, hydrochloride 0.88 g (36.3 mmole) of magnesium turnings was stirred in 10 ml of tetrahydrofuran of analysis purity. 4.55 ml (36.3 mmole) of 4-bromoanisole dissolved in 30 ml of tetrahydrofuran were added dropwise so that the reaction mixture boiled gently. After completion of the addition the reaction mixture was stirred for a further hour at RT. 7.0 g (30.3 mmole) of 2-(dimethylaminophenylmethyl)cyclohexanone prepared according to Example 1 were dissolved in 10 ml of tetrahydrofuran, added dropwise to the Grignard reagent while cooling in an ice bath, and stirred for 15 hours at RT. The reaction solution was worked up by adding 40 ml of saturated ammonium chloride solution while cooling in an ice bath, and extracted three times at RT with in each case 100 ml of ethyl acetate. The combined organic extracts were dried over sodium sulfate, filtered and concentrated by evaporation on a rotary evaporator (500 to 10 mbar). 10.5 g of crude base (102% of theory) were obtained. 4.24 g of 2-(dimethylaminophenylmethyl)-1-(4-methoxyphenyl) cyclohexanol, hydrochloride (37.2% of theory) were obtained from the crude base according to the procedure described in Example 1 ($3^{rd}$ stage) with chlorotrimethylsilane/water in 2-butanone. The hydrochloride decomposes on heating above 150° C.

Example 6

1-(4-chlorophenyl)-2-(dimethylaminophenylmethyl) cyclohexanol, hydrochloride 0.63 g (25.9 mmole) of magnesium turnings was stirred in 10 ml of ether of analysis purity. 4.97 g (25.9 mmole) of 4-bromochlorobenzene dissolved in 30 ml of ether were added dropwise so that the reaction mixture boiled gently. After completion of the addition the reaction mixture was boiled for a further hour at RT. 5.0 g (21.6 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction solution was worked up by adding 40 ml of saturated ammonium chloride solution while cooling in an ice bath, and extracted three times at RT with in each case 100 ml of ethyl acetate. The combined organic extracts were dried over sodium sulfate, filtered and concentrated by evaporation on a rotary evaporator (500 to 10 mbar). 7.24 g of crude base (97.4% of theory) were obtained. 5.43 g of 1-(4-chlorophenyl)-2-(dimethylaminophenylmethyl)cyclohexanol, hydrochloride (66.0%) of theory) were obtained from the crude base according to the procedure described in Example 1 ($3^{rd}$ stage) with chlorotrimethylsilane/water in 2-butanone. The hydrochloride decomposes on heating above 175° C.

Example 7

2-(dimethylaminophenylmethyl)-1-(4-fluorophenyl) cyclohexanol, hydrochloride 0.50 g (20.7 mmole) of magnesium turnings was stirred in 10 ml of ether of analysis purity. 2.28 ml (20.7 mmole) of 4-bromofluorobenzene dissolved in 20 ml of ether were added dropwise so that the reaction mixture boiled gently. After completion of the addition the reaction mixture was stirred for a further hour at RT. 4.0 g (17.3 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction solution was worked up by adding 30 ml of saturated ammonium chloride solution while cooling in an ice bath, and was extracted three times at RT with in each case 80 ml of ethyl acetate. The combined organic extracts were dried over sodium sulfate, filtered, and concentrated by evaporation on a rotary evaporator (500 to 10 mbar). 5.50 9 of crude base (97.2% of theory) were obtained. 3.61 g of 2-(dimethylaminophenylmethyl)-1-(4-fluorophenyl) cyclohexanol, hydrochloride (57.4% of theory) were obtained from the crude base according to the procedure described in Example 1 ($3^{rd}$ stage) with chlorotrimethylsilane/water in 2-butanone. The hydrochloride decomposes on heating above 150° C.

Example 8

2-(dimethylaminophenylmethyl)-1-p-tolylcyclohexanol, hydrochloride 0.50 g (20.7 mmole) of magnesium turnings was stirred in 10 ml of ether of analysis purity. 2.55 ml (20.7 mmole) of 4-bromotoluene dissolved in 20 ml of ether were added dropwise so that the reaction mixture boiled gently. After completion of the addition the reaction mixture was stirred for a further hour at RT. 4.0 g (17.3 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction solution was worked up by adding 30 ml of saturated ammonium chloride solution while cooling in an ice bath, and was extracted three times at RT with in each case 80 ml of ethyl acetate. The combined organic extracts were dried over sodium sulfate, filtered, and concentrated by evaporation on a rotary evaporator (500 to 10 mbar). 5.35 g of crude base (95.7% of theory) were obtained. 1.73 g of 2-(dimethylaminophenylmethyl)-1-p-tolylcyclohexanol, hydrochloride (27.8% of theory) with a melting point of 168–169° C. were obtained from the crude base according to the procedure described in Example 1 ($3^{rd}$ stage) with chlorotrimethylsilane/water in 2-butanone.

Example 9

1-(3-chlorophenyl)-2-[dimethylamino-((3-methoxyphenyl)methyl]cyclohexanol, hydrochloride $1^{st}$ Stage C-(3-methoxyphenyl)-N,N,N',N'-tetramethylmethanediamine 18.3 ml (0.15 mole) of 3-anisaldehyde were heated for five hours at 50° C. with 38 ml (0.30 mole) of dimethylamine solution (40 m % in water) while stirring, and then stirred for a further 15 hours at RT. The reaction solution was worked up by adding 20 ml of saturated potassium carbonate solution and solid potassium carbonate until a pH of ca. 9 was reached. The reaction solution was extracted three times, each time with 200 ml of ethyl acetate. The combined organic extracts were dried over potassium carbonate, filtered, and concentrated by evaporation on a rotary evaporator (500 to 10 mbar). 27.0 g of C-(3-methoxyphenyl)-N,N,N',N'tetramethylmethanediamine (86.3% of theory) were obtained in this way.

$2^{nd}$ Stage (3-methoxybenzylidene)dimethyl ammonium chloride 30 g (144 mmole) of C-(3-methoxyphenyl)-N,N,N',N'-tetramethylmethanediamine from stage 1 were dissolved in 200 ml of ether and cooled in an ice bath (methanol/ice 1:1) to –10° C. 10.3 ml (144 mmole) of acetyl chloride were added dropwise under nitrogen. A white salt precipitated out, and the temperature rose slightly. After 15 hours at RT the solution was decanted off, and the solids were washed three times, each time with 100 ml of ether, filtered through a protective gas frit under nitrogen, and dried to constant weight in an oil pump vacuum. 19.8 g of (3-methoxybenzylidene)dimethyl ammonium chloride (68.8% of theory) were obtained in this way.

$3^{rd}$ Stage

2-[dimethylamino-(3-methoxyphenyl)methyl] cyclohexanone 15.3 ml (95 mmole) of 1-(pyrrolidino)-1-cyclohexene were dissolved in 100 ml of dichloromethane and cooled under nitrogen in a dry ice/isopropanol bath to –70° C. 19 g (95 mmole) of (3-methoxybenzylidene)dimethyl ammonium chloride from stage 2 were added while stirring, and the mixture was heated to –30° C. within two to three hours and kept for 15 hours at this temperature. The reaction mixture was worked up by adding 60 ml of semi-concentrated hydrochloric acid and stirred for a further 5 minutes. The mixture was extracted at RT with 50 ml of ether, 100 ml of ammonia solution (25 vol. %) was added to the aqueous phase, and the latter was extracted quickly three times, each time with 200 ml of ether. The combined organic extracts were dried over sodium sulfate, filtered, and concentrated by evaporation on a rotary evaporator without heating (500 to 10 mbar). 19.1 g of crude base (76.6% of theory) were obtained in this way. 18.0 g of the hydrochloride of 2-[dimethylamino-(3-methoxyphenyl)-methyl] cyclohexanone (63.7% of theory) having a melting point of 142° C. were obtained from the crude base according to the procedure described in Example 1 ($2^{nd}$ stage) with chlorotrimethylsilane/water in 2-butanone.

$4^{th}$ Stage 1-(3-chlorophenyl)-2-[dimethylamino-(3-methoxyphenyl) methyl]cyclohexanol, hydrochloride 0.55 g (22.4 mmole) of magnesium turnings was stirred in 10 ml of ether of analysis purity. 2.6 ml (22.4 mmole) of 3-bromochlorobenzene dissolved in 20 ml of ether were added dropwise so that the reaction mixture boiled gently. After completion of the addition the reaction mixture was stirred for a further hour at RT. The base was freed front 6 g (20.1 mmole) of the hydrochloride of 2-[dimethylamino-(3-methoxyphenyl)methyl]-cyclohexanone obtained according to stage 3, with 60 ml of water and 5 ml of caustic soda (32 m %), was extracted three times, each time with 60 ml of ether, and the combined organic extracts were dried over sodium sulfate, filtered, and concentrated by evaporation on a rotary evaporator without heating (500 to 10 mbar). 4.9 g (18.7 mmole) of this base were dissolved in 10 ml of ether, added dropwise to the Grigiard reagent while cooling in an ice bath, and stirred for 15 hours at RT. The reaction solution was worked up by adding 30 ml of saturated anmonium chloride solution while cooling in an ice bath and was extracted three times at RT, each time with 80 ml of ethyl acetate. The combined organic extracts were dried over sodium sulfate, filtered, and concentrated by evaporation on a rotary evaporator (500 to 10 mbar). 6.51 g of crude base (100% of theory) were obtained. 5.0 g of 1-(3-chlorophenyl)-2-[dimethylamino-(3-methoxyphenyl) methyl]cyclohexanol, hydrochloride (70.1% of theory) having a melting point of 131° C.–133° C. were obtain ed from the crude base according to the procedure describe bed in Example 1 ($3^{rd}$ stage) with chlorotrimethylsilane/water in 2-butanone.

Example 10

1-(4-dimethylaminophenyl)-2-[dimethylaminophenylmethyl]cyclohexanol, hydrochloride 0.50 g (20.7 mmole) of magnesium turnings was stirred in 5 ml of tetrahydrofuran of analysis purity. 4.14 g (20.7 mmole ) of 4-bromo-N,N-dimethylaniline dissolved in 10 ml of tetrahydrofuran were added dropwise so that the reaction mixture boiled gently. After completion of the addition the reaction mixture w as stirred for a further hour at 55° C. 4.0 g (17.3 mmole) of the 2-(dimethylaminophenylmethyl) cyclohexanone prepared according to Example 1 were dissolved in 10 ml of tetrahydrofuran, added to the Grignard reagent while cooling in an ice bate, and stirred for 15 hours at RT. The reaction solution was worked up by adding 40 ml of saturated ammonium chloride solution while cooling in an ice bath, and was extracted three times at RT, each time with 100 ml of ethyl acetate. The combined organic extracts were dried over sodium sulfate, filtered, and concentrated by evaporation on a rotary evaporator (500 to 10 mbar). 6.24 g of crude base (102% of theory) were obtained, from which a hydrochloride was precipitated according to the procedure described in Example 1 ($3^{rd}$ stage) with chlorotrimethylsilane/water in 2-butanone. The base was freed from the hydrochloride with 30 ml of water and 4 ml of caustic soda (32 m %), extracted three times, each time with 30 ml of ether, and the combined organic extracts were dried over sodium sulfate, filtered, and concentrated by evaporation on a rotary evaporator (500 to 10 mbar). 1.90 g of crude base (26.9% of theory) were obtained. 0.88 g of 1-(4-dimethyl-aminophenyl)-2-(dimethylaminophenylmethyl]cyclohexanol, hydrochloride (10.9% of theory) having a melting point of 124° C.–125° C. were obtained from the crude base according to the procedure described in Example 1 ($3^{rd}$ stage) with chlorotrimethylsilane/water in 2-butanone.

Example 11

1-benzo[1,3]dioxol-4-yl-2-(dimethylaminophenylmethyl)cyclohexanol, hydrochloride 2.61 g (13 mmole) of 4-bromo-1,2-methylenedioxybenzene were dissolved in 10 ml of tetrahydrofuran and cooled under nitrogen to –70° C. in a dry ice/isopropanol bath. 9.35 ml (15 mmole) of n-butyllithium (1.6 1M in hexane) were added dropwise while stirring so that the temperature did not rise above –60° C.). The reaction mixture was stirred for 30 minutes, following which 3.0 g (13 mmole) of the 2-(dimethylaminophenyl-methyl)cyclohexanone prepared according to Example 1 and dissolved in 10 ml of tetrahydrofuran were added dropwise while cooling in an ice bath, and the whole was then heated to RT over two hours. The reaction mixture was worked up by adding 20 ml of saturated ammonium chloride solution while cooling in an ice bath and was extracted three times at RT, each time with 70 ml of ethyl acetate. The combined organic extracts were dried over sodium sulfate, filtered, and concentrated by evaporation on a rotary evaporator (500 to 10 mbar). 4.67 g of crude base (102% of theory) were obtained. 3.05 g of 1-benzo[1,3] dioxol-4-yl-2-(dimethylaminophenyl-methyl)cyclohexanol, hydrochloride (60.3% of theory) having a melting point of 209° C. were obtained from the crude base according to the procedure described in Example 1 ($3^{rd}$ stage) with chlorotrimethylsilane/water in 2-butanone.

Example 12

(3,4-dimethoxyphenyl)-2-(dimethylaminophenylmethyl)cyclohexanol, hydrochloride 2.82 g (13 mmole) of 3-bromoveratrole were dissolved in 20 ml of tetrahydrofuran and cooled under nitrogen to –70° C. in a dry ice/isopropanol bath. 9.35 ml (15 mmole) of n-butyllithium (1.6 M in hexane) were added dropwise while stirring so that the temperature did not rise above –60° C. The reaction solution was stirred for a further 30 minutes, following which 3.0 g (13 mmole) of the 2-(dimethylaminophenylmethyl)cyclohexanone prepared according to Example 1 and dissolved in 10 ml of tetrahydrofuran were added dropwise while cooling in an ice bath and then heated to RT within two hours. The reaction solution was worked up by adding 20 ml of saturated ammonium chloride solution while cooling in an ice bath, and was extracted three times at RT, each time with 70 ml of ethyl acetate. The combined organic extracts were dried over sodium sulfate, filtered, and concentrated by evaporation on a rotary evaporator (500 to 10 mbar). 5.09 g of crude base (106% of theory) were obtained. 3.73 g of (3,4-dimethoxyphenyl)-2-(dimethylaminophenylmethyl)cyclohexanol, hydrochloride (70.8% of theory) having a melting point of 205–207° C. were obtained from the crude base according to the procedure described in Example 1 ($3^{rd}$ stage) with chlorotrimethylsilane/water in 2-butanone.

Example 13

2-(dimethylaminophenylmethyl)-1-(3-methoxybenzyl)cyclohexanol, hydrochloride 0.63 g (25.9 mmole) of magnesium turnings was stirred in 10 ml of ether of analysis purity. 5.21 g (25.9 mmole) of 3-methoxybenzyl bromide dissolved in 20 ml of ether were added dropwise so that the reaction mixture boiled gently. After completion of the addition the reaction mixture was stirred for a further hour at RT. 5.0 g (21.6 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction solution was worked up by adding 40 ml of saturated ammonium chloride solution while cooling in an ice bath, and was extracted three times at RT, each time with 80 ml of ethyl acetate. The combined organic extracts were dried over sodium sulfate, filtered, and concentrated by evaporation on a rotary evaporator (500 to 10 mbar). 7.53 g of crude base (98.6 of theory) were obtained. 4.45 g of 2-(dimethylaminophenylmethyl)-1-(3-methoxybenzyl)cyclohexanol, hydrochloride (52.8% of theory) were obtained from the crude base according to the procedure described in Example 1 ($3^{rd}$ stage) with chlorotrimethylsilane/water in 2-butanone. The hydrochloride decomposes when heated above 160° C.

Example 14

1-benzyl-2-(dimethylaminophenylmethyl)cyclohexanol, hydrochloride 0.63 g (25.9 mmole) of magnesium turnings was stirred in 10 ml of ether of analysis purity. 4.43 g (25.9 mmole) of benzyl bromide dissolved in 20 ml of ether were added dropwise so that the reaction mixture boiled gently. After completion of the addition the reaction mixture was stirred for a further hour at RT. 5.0 g (21.6 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction mixture was worked up by adding 40 ml of saturated ammonium chloride solution while cooling in an ice bath, and was extracted three times at RT, each time with 80 ml of ethyl acetate. The combined organic extracts were dried over sodium sulfate, filtered, and concentrated by evaporation on a rotary evaporator (500 to 10 mbar). 6.84 g of crude base (97.9° of theory) were obtained. 1.61 g of 1-benzyl-2-(dimethylaminophenylmethyl)cyclohexanol, hydrochloride (20.7% of theory) having a melting point of 223–225° C. were obtained from the crude base according to the procedure described in Example 1 ($3^{rd}$ stage) with chlorotrimethylsilane/water in 2-butanone.

Example 15

2-(dimethylaminophenylmethyl)-1-(4-fluoro-3-trifluoromethylphenyl)cyclohexanol, hydrochloride 0.25 g (10.3 mmole) of magnesium turnings was stirred in 15 ml of ether of analysis purity. 2.2 g (10.3 mmole) of 5-bromo-2-fluorobenzotrifluoride dissolved in 15 ml of ether were added dropwise so that the reaction mixture boiled gently. After completion of the addition the reaction mixture was stirred for a further hour at RT. 1.80 g (8.57 mmole) of the 2-(dimethylaminophenylmethyl)cyclohexanone prepared according to Example 1 were dissolved in 15 ml of ether, added dropwise to the Grignard reagent while cooling in an ice bath, and stirred for 15 hours at ET. The reaction mixture was worked up by adding 20 ml of saturated anmonium chloride solution while cooling in an ice bath, and was extracted three times at RT, each time with 40 ml of ethyl acetate. The combined organic extracts were dried over sodium sulfate, filtered, and concentrated by evaporation on a rotary evaporator (500 to 10 mbar). 3.9 g of crude base (126% of theory) were obtained. 2.14 g of 2-(dimethylaminophenylmethyl)-1-(4-fluoro-3-trifluoromethylphenyl)cyclohexanol, hydrochloride (63.7% of theory) having a melting point of 234–237° C. were obtained from the crude base according to the procedure described in Example 1 (3$^{rd}$ stage) with chlorotrimethylsilane/water in 2-butanone.

Example 16

2-(dimethylaminophenylmethyl)-1-(4-trifluoromethoxybenzyl)cyclohexanol, hydrochloride 0.10 g (4.2 mmole) of magnesium turnings was stirred in 10 ml of ether of analysis purity. 1.0 g (4.2 mmole) of 4-(trifluoromethoxy)benzyl bromide dissolved in 10 ml of ether was added dropwise so that the reaction mixture boiled gently. After completion of the addition the reaction mixture was stirred for a further hour at RT. 0.8 g (3.5 mmole) of the 2-(dimethylaminophenylmethyl)cyclohexanone prepared according to Example 1 was dissolved in 10 ml of ether, added dropwise to the Grignard reagent while cooling in an ice bath, and stirred for 15 hours at RT. The reaction mixture was worked up by adding 20 ml of saturated ammonium chloride solution while cooling in an ice bath, and was extracted three times at RT, each time with 30 ml of ethyl acetate. The combined organic extracts were dried over sodium sulfate, filtered, and concentrated by evaporation on a rotary evaporator (500 to 10 mbar). 1.65 g of crude base (121% of theory) were obtained. 0.64 g of 2-(dimethylaminophenylmethyl)-1-(4-trifluoromethoxybenzyl)cyclohexanol, hydrochloride (41.7% of theory) were obtained from the crude base according to the procedure described in Example 1 (3$^{rd}$ stage) with chlorotrimethylsilane/water in 2-butanone. The hydrochloride decomposes on heating above 178° C.

Example 17

2-(dimethylaminophenylmethyl)-1-furan-3-ylcyclohexanol, hydrochloride 1.0 g (6.8 mmole) of 3-bromofuran was dissolved in 10 ml of tetrahydrofuran and cooled under nitrogen to −70° C. in a dry ice/isopropanol bath. 5.1 ml (8.1 mmole) of n-butyllithium (1.6 M in hexane) were added dropwise while stirring so that the temperature did not rise above −60° C.). The reaction mixture was stirred for a further 30 minutes and then 1.57 g (6.8 mmole) of the 2-(dimethylaminophenylmethyl)cyclohexanone prepared according to Example 1 dissolved in 10 ml of tetrahydrofuran were added dropwise while cooling in an ice bath, and heated to RT within two hours. The reaction mixture was worked up by adding 20 ml of saturated ammonium chloride solution while cooling iii an ice bath, and was extracted three times at RT, each time with 50 ml of ethyl acetate. The combined organic extracts were dried over sodium sulfate, filtered, and concentrated by evaporation on a rotary evaporator (500 to 10 mbar) 2.15 g of crude base (106% of theory) were obtained, from which a hydrochloride was precipitated according to the procedure described in Example 1 (3$^{rd}$ stage) with chlorotrimethylsilane/water in 2-butanone. The base was freed from the hydrochloride with 20 ml of water and 3 ml of caustic soda (32 m %), was extracted three times, each time with 30 ml of ether, and the combined organic extracts were dried over sodium sulfate, filtered, and concentrated by evaporation on a rotary evaporator (500 to 10 mbar). 1.29 g of crude base (63.4% of theory) were obtained, which were added to a 4×30 cm column filled with silica gel. Elution with diisopropyl ether/methanol (4.7:0.3) yielded 0.33 g of base, from which 0.28 g of 2-(dimethylaminophenylmethyl)-1-furan-3-ylcyclohexanol, hydrochloride (12.4% of theory) was obtained according to the procedure described in Example 1 (3$^{rd}$ stage) with chlorotrimethylsilane/water in 2-butanone. The hydrochloride decomposes on heating above 130° C.

Example 18

1-butyl-2-(dimethylaminophenylmethyl) cyclohexanol, hydrochloride 2.43 g (7.2 mmole) of (1-bromonaphthalene-2-yloxy)-tert.-butyldimethylsilane were dissolved in 10 ml of tetrahydrofuran and cooled to −70° C. in a dry ice/isopropanol bath. 5.4 ml (8.6 mmole) of n-butyllithium (1.6 M in hexane) were added dropwise under nitrogen while stirring, and then stirred for a further 30 minutes. 2.7 g (7.2 mmole) of the 2-(dimethylaminophenylmethyl)cyclohexanone prepared according to Example 1 and dissolved in 10 ml of tetrahydrofuran were added dropwise and the reaction mixture was heated to RT within two hours. The reaction mixture was worked up by adding 20 ml of saturated ammonium chloride solution while cooling in an ice bath, and was extracted three times at RT, each time with 50 ml of ethyl acetate. The combined organic extracts were dried over sodium sulfate, filtered, and concentrated by evaporation on a rotary evaporator (500 to 10 mbar). 4.65 g of crude base were obtained (223% of theory), to which were added 10 ml of n-hexane, 9 ml of methanol and 4.7 ml of hydrochloric acid (2 N). The aqueous phase was separated, the methanol was distilled off on a rotary evaporator (500 to 10 mbar), the solution was adjusted alkaline (pH ca. 9) with sodium carbonate solution (1 M), and was extracted three times at RT, each time with 50 ml of ethyl acetate. The combined organic extracts were dried over sodium sulfate, filtered, and concentrated by evaporation on a rotary evaporator (500 to 10 mbar). 2.34 g of crude base (53.4% of theory) were obtained, which were added to a 3.5×15 cm column filled with silica gel. Elution with ethyl acetate/n-hexane (2:3) yielded 0.23 g of base, from which 0.13 g of 1-butyl-2-(dimethylaminophenylmethyl)cyclohexanol, hydrochloride (5.5% of theory) was obtained according to the procedure described in Example 1 (3$^{rd}$ stage) with chlorotrimethylsilane/water in 2-butanone. The hydrochloride decomposes on heating above 110° C.

Example 19

(−)-1(3,4-dichlorophenyl)-2-(dimethylaminophenylmethyl)cyclohexanol, hydrochloride, and (+)-1-(3,4-dichlorophenyl)-2-(dimethylaminophenylmethyl)cyclohexanol, hydrochloride 0.78 g (32.1 mmole) of magnesium turnings was stirred in 10 ml of ether of analysis purity. 7.13 g (31.0 mmole) of 1-bromo-3,4-dichlorobenzene dissolved in 20 ml of ether were added dropwise so that the reaction mixture boiled gently. After completion of the addition the reaction mixture was stirred for a further hour at RT. 6.0 g (26.0 mmole) of the 2-(dimethylaminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 40 ml of saturated ammonium chloride solution while cooling in an ice bath, and was extracted three times at RT, each time with 100 ml of ethyl acetate. The combined organic extracts were dried over sodium sulfate, filtered, and concentrated by evaporation on a rotary evaporator (500 to 10 mbar). 10.4 g of crude base (106% of theory) were obtained.

1.96 g (5.2 mmole) of this base were dissolved in 20 ml of 15 2-butanone, 0.78 g of L(+) tartaric acid (5.2 mmole) was added and dissolved by heating, and the reaction mixture was kept for one week at 4° C., a white precipitate being formed. The precipitate was filtered off, washed several times with a small amount of 2-butanone and ether, dissolved in 20 ml of water, following which the base was freed with 2 ml of caustic soda (32 m %) and extracted three times, each time with 30 ml of ethyl acetate. The combined organic extracts were dried over sodium sulfate, filtered, and concentrated by evaporation on a rotary evaporator (500 to 10 mbar). 0.69 g (1.8 mmole) of crude base was obtained. The optical purity was determined by HPLC. The crude base was dissolved in hexane/isopropanol/diethylamine (990:10:1) (0.1 vol. %), and 20 µl of the solution were injected into a Chiracel OD 250×4.6 mm colunm with a precolumn (Daicel) and eluted with the solvent system hexane/isopropanol/diethylamine (990:10:1) at a flow rate of 1 ml/min through the column. The base was detected at a wavelength of 254 nm. The degree of purity was 98.8% ee. 0.32 g (0.77 mmole) of (−)-1-(3,4-dichlorophenyl)-2-(dimethylaminophenylmethyl)cyclohexanol, hydrochloride (29.7% of theory) having an angle of rotation of $[\alpha]D^{20}$=−27.9 (c=1.097 in methanol) was obtained from the crude base according to the procedure described in Example 1 ($3^{rd}$ stage) with chlorotrimethylsilane/water in 2-butanone. The mother liquor of the filtered-off base/tartaric acid mixture was concentrated by evaporation and the base was freed with caustic soda as described in the case of the previously obtained precipitate, following which a hydrochloride was precipitated with chlorotrimethylsilane/water in 2-butanone. The base was once more freed from the hydrochloride with caustic soda, 0.62 g (1.6 mmole) of crude base being obtained. This crude base was dissolved in 6 ml of 2-butanone, 0.25 g (1.6 mmole) of D(−) tartaric acid was added, the resultant precipitate was filtered off, washed several times with a small amount of 2-butanone and ether, dissolved in 20 ml of water, and the base was then freed with 2 ml of caustic soda (32 m %) and extracted three times, each time with 30 ml of ethyl acetate. The combined organic extracts were dried over sodium sulfate, filtered, and concentrated by evaporation on a rotary evaporator (500 to 10 mbar). 0.33 g (0.87 mmole) of crude base was obtained. The optical purity was determined as above by HPLC. The purity was 98.5% ee. 0.12 g (0.29 mmole) of (+)-1-(3,4-dichlorophenyl)-2-(dimethylaminophenylmethyl)cyclohexanol, hydrochloride (11.1% of theory) having an angle of rotation of $[\alpha]D^{20}$=+27.3 (c=1.081 in methanol) was obtained from the crude base according to the procedure described in Example 1 ($3^{rd}$ stage) with chlorotrimethylsilane/water in 2-butanone.

Example 20

4-[2-(dimethylaminophenylmethyl)-1-hydroxycyclohexyl]phenol, hydrochloride 0.38 g (15.5 mmole) of magnesium turnings was stirred in 5 ml of tetrahydrofuran of analysis purity. 3.81 g (15.5 mmole) of 1-(4-bromophenoxy)-1-ethoxyethane dissolved in 5 ml of tetrahydrofuran were added dropwise so that the reaction mixture boiled gently. After completion of the addition the reaction mixture was stirred for a further hour at 55° C. 3.0 g (13.0 mmole) of the 2-(dimethylaminophenylmethyl)cyclohexanone prepared according to Example 1 were dissolved in 15 ml of tetrahydrofuran, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, each time with 80 ml of ethyl acetate. The combined organic extracts were dried over sodium sulfate, filtered, and concentrated on a rotary evaporator (500 to 10 mbar). 5.25 g of crude base were obtained, which were dissolved in 20 ml of ether followed by the addition of 10 ml of hydrochloric acid (1 N). The aqueous phase was separated and sufficient sodium bicarbonate was added to adjust the pH to ca. 8. The base was extracted three times, each time with 20 ml of ether, and the combined organic extracts were dried over sodium sulfate, filtered, and concentrated by evaporation on a rotary evaporator (500 to 10 mbar). 1.96 g of crude base (46.3% of theory) were obtained, from which 1.8 g of 4-[2-(dimethylaminophenylmethyl)-1-hydroxycyclohexyl]phenol, hydrochloride were obtained (38.6% of theory) with 0.49 ml of hydrochloric acid (32 m %,) and 20 ml of acetone. The hydrochloride decomposes on heating above 140° C.

Example 21

2-(dimethylaminophenylmethyl)-1-naphthalene-2-ylcyclohexanol, hydrochloride 1.01 g (25.9 mmole) of potassium were added under nitrogen to 1.37 g (14.2 mmole) of dry magnesium chloride dissolved in 35 ml of tetrahydrofuran, and heated to 65° C. while stirring.

The suspension was heated under reflux for three hours, 2.99 g (14.0 mmole) of 2-bromonaphthalene dissolved in 10 ml of tetrahydrofuran were added dropwise, the reaction mixture was stirred for a further 1.5 hours, cooled to RT, 2.65 g (13.0 mmole) of the 2-(dimethylaminophenylmethyl)cyclohexanone prepared according to Example 1 and dissolved in 10 ml of tetrahydrofuran were then added dropwise, and the reaction mixture was stirred for 15 hours at BT. The reaction mixture was worked up by adding 20 ml of saturated ammonium chloride solution while cooling in an ice bath, and was extracted three times at RT, each time with 80 ml of ethyl acetate. The combined organic extracts were dried over sodium sulfate, filtered, and concentrated by evaporation on a rotary evaporator (500 to 10 mbar). 4.2 g of crude base (102% of theory) were obtained, from which a hydrochloride was precipitated according to Example 1 ($3^{rd}$ stage) with chlorotrimethylsilane/water in 2-butanone. The base was freed from the hydrochloride with 20 ml of water and 3 ml of caustic soda (32 m %), and was extracted three times, each time with 30 ml of ether, and the combined organic extracts were dried over sodium sulfate, filtered, and concentrated by evaporation on a rotary evaporator (500 to 10 mbar). 0.42 g of 2-(dimethylaminophenylmethyl)-1-napththalene-2-ylcyclohexanol, hydrochloride (9.2% of theory) was obtained from the crude base according to the procedure described in Example 1 ($3^{rd}$ stage) with chlorotrimethylsilane/water in 2-butanone. The hydrochloride decomposes on heating above 240° C.

Example 22

2-[dimethylamino-(4-trifluoromethylphenyl)methyl]-1-(3-methoxybenzyl)cyclohexanol, hydrochloride 1st Stage N,N,N',N'-tetramethyl-C-(4-trifluoromethylphenyl) methanediamine 81 ml (0.632 mole) of dimethylamine solution (40 m % in water) were added to 55 g (0.315 mole) of 4-(trifluoromethyl) benzaldehyde while stirring and cooling in an ice bath, and the mixture was stirred for a further 15 hours at RT. The reaction mixture was worked up by adding 40 ml of saturated potassium carbonate solution and solid potassium carbonate until a pH of ca. 9 was reached. The reaction mixture was extracted three times, each time with 300 ml of ethyl acetate. The combined organic extracts were dried over potassium carbonate, filtered, and concentrated by evaporation on a rotary evaporator (500 to 10 mbar). 68.3 g of N,N,N',N'-tetramethyl-C-(4-trifluoromethylphenyl) methanediamine (87.8% of theory) were obtained in this way.

2nd Stage

2-[dimethylamino-(4-trifluoromethylphenyl)methyl] cyclohexanone 63 g (2.56 mmole) of N,N,N',N'-tetramethyl-C-(4-trifluoromethylphenyl)methanediamine from stage 1 were dissolved in 450 ml of ether and cooled to 0° C. in an ice bath. 18.3 ml (256 mmole) of acetyl chloride were added dropwise under nitrogen and the reaction mixture was stirred for 15 hours at RT. The solution was cooled to −70° C. with a dry ice/isopropanol bath, 38.7 g (256 mmole) of 1-(pyrrolidino)-1-cyclohexene dissolved in 300 ml of dichloromethane were added dropwise, the mixture was heated to −30° C. within three hours, and kept for 15 hours at this temperature. The reaction mixture was worked up by adding 200 ml of semi-concentrated hydrochloric acid and stirred for a further 5 minutes. The phases were separated and the aqueous solution was extracted at RT with 150 ml of ether, following which 400 ml of ammonia solution (5 vol. %) were added and the mixture was quickly extracted three times, each time with 400 ml of ether. The combined organic extracts were dried over sodium sulfate, filtered, and concentrated on a rotary evaporator without heating (500 to 10 mbar) 63.1 g of crude base (82.4% of theory) were obtained in this way. 51.4 g of the hydrochloride of 2-[dimethylamino-(4-trifluoromethylphenyl)methyl] cyclohexanone (59.8% of theory) having a melting point of 139–140° C. were obtained from the crude base according to the procedure described in Example 1 (2nd stage) with chlorotrimethylsilane/water in 2-butanone.

3rd Stage

2-[dimethylamino-(4-trifluoromethylphenyl)methyl]-1-(3-methoxybenzyl)cyclohexanol, hydrochloride 0.29 g (12.0 mmole) of magnesium turnings was stirred in 5 ml of ether of analysis purity. 2.42 g (12.0 mmole) of 3-methoxybenzyl bromide dissolved in 10 ml of ether were added dropwise so that the reaction mixture boiled gently. After completion of the addition the reaction mixture was stirred for a further hour at RT. 3.0 g (10.0 mmole) of the 2-[dimethyl-amino-(4-trifluoromethylphenyl)methyl] cyclohexanone prepared according to stage 2 were dissolved in 5 ml of ether, added dropwise to the Grignard reagent while cooling in an ice bath, and stirred for 15 hours at RT. The reaction solution was worked up by adding 30 ml of saturated ammonium chloride solution while cooling in an ice bath, and was extracted three times at RT, each time with 50 ml of ethyl acetate. The combined organic extracts were dried over sodium sulfate, filtered, and concentrated by evaporation on a rotary evaporator (500 to 10 mbar). 5.60 g of crude base (133% of theory) were obtained. 3.26 g of 2-[dimethylamino-(4-trifluoromethyl-phenyl)methyl]-1-(3-methoxybenzyl)cyclohexanol, hydrochloride (70.9% of theory) were obtained from the crude base according to the procedure described in Example 1 (3rd stage) with chlorotrimethylsilane/water in 2-butanone. The hydrochloride decomposes on heating above 133° C.

Example 23

1-(4-chlorobenzyl)-2-(dimethylaminophenylmethyl)-1-cyclohexanol, hydrochloride 0.38 g (15.6 mmole) of magnesium turnings was stirred in 15 ml. of ether of analysis purity. 1.99 g (15.6 mmole) of 4-chlorobenzyl bromide dissolved in 15 ml of ether were added dropwise so that the reaction mixture boiled gently. After completion of the addition the reaction mixture was stirred for a further hour at RT. 3.0 g (13.0 mmole) of the 2-(dimethyl-aminophenylmethyl)cyclohexanone prepared according to Example 1 were dissolved in 15 ml of ether, added dropwise to the Grignard reagent while cooling in an ice bath, and stirred for 15 hours at RT. The reaction solution was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation on a rotary evaporator (500 to 10 mbar). 4.48 g of crude base (96.5% of theory) were obtained. 1.74 g of 1-(4-chlorobenzyl)-2-(dimethylaminophenylmethyl)-1-cyclohexanol, hydrochloride (34.0% of theory) were obtained from the crude base according to the procedure described in Example 1 (3rd stage) with chlorotrimethylsilane/water in 2-butanone. The hydrochloride decomposes on heating above 208° C.

Example 24

2-(dimethylaminophenylmethyl)-1-(2-fluorobenzyl) cyclohexanol, hydrochloride 0.38 g (15.6 mmole) of magnesium turnings was stirred in 15 ml of ether of analysis purity. 1.85 g (15.6 mmole) of 2-fluorobenzyl bromide dissolved in 15 ml of ether were added dropwise so that the reaction mixture boiled gently. After completion of the addition the reaction mixture was stirred for a further hour at RT. 3.0 g (13.0 mmole) of the 2-(dimethylaminophenylmethyl)cyclohexanone prepared according to Example 1 were dissolved in 15 ml of ether, added dropwise to the Grignard reagent while cooling in an ice bath, and stirred for 15 hours at RT. The reaction solution was worked up by adding 30 ml of saturated ammonium chloride solution while cooling in an ice bath, and was extracted three times at RT with in each case 60 ml of ethyl acetate. The combined organic extracts were dried over sodium sulfate, filtered, and concentrated by evaporation on a rotary evaporator (500 to 10 mbar). 3.50 g of crude base (79.0% of theory) were obtained. 1.75 g of 2-(dimethylaminophenylmethyl)-1-(2-fluorobenzyl) cyclohexanol, hydrochloride (35.7% of theory) were obtained from the crude base according to the procedure described in Example 1 (3rd stage) with chlorotrimethylsilane/water in 2-butanone. The hydrochloride decomposes on heating above 175° C.

Example 25

2-(dimethylaminophenylmethyl)-1-(4-fluorobenzyl) cyclohexanol, hydrochloride 0.38 g (15.6 mmole) of magnesium turnings was stirred in 15 ml of ether of analysis purity. 1.87 g (15.6 mmole) of 4-fluorobenzyl bromide dissolved in 15 ml of ether were added dropwise so that the reaction mixture boiled gently. After completion of the addition the reaction mixture was stirred for a further hour at RT. 3.0 g (13.0 mmole) of the 2-(dimethyl-aminophenylmethyl)cyclohexanone prepared according to Example 1 were dissolved in 15 ml of ether, added dropwise to the Grignard reagent while cooling in an ice bath, and stirred for 15 hours at RT. The reaction solution was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation an a rotary evaporator (500 to 10 mbar). 4.51 g of crude base (102% of theory) were obtained. 2.59 g of 2-(dimethylaminophenylmethyl)-1-(4-fluorobenzyl) cyclohexanol, hydrochloride (52.8% of theory) were obtained from the crude base according to the procedure described in Example 1 ($3^{rd}$ stage) with chlorotrimethylsilane/water in 2-butanone. The hydrochloride decomposes on heating above 203° C.

Example 26

1-(2,5-dimethoxyphenyl)-2-(dimethylaminophenylmethyl)cyclohexanol, hydrochloride 0.38 g (15.6 mmole) of magnesium turnings was stirred in 15 ml of tetrahydrofuran of analysis purity. 3.39 g (15.6 mmole) of 1-bromo-2,5-dimethoxybenzene dissolved in 15 ml of tetrahydrofuran were added dropwise so that the reaction mixture boiled gently. After completion of the addition the reaction mixture was stirred for a further 1.5 hours at 65° C. 3.0 g (13.0 mmole) of the 2-(dimethylaminophenylmethyl) cyclohexanone prepared according to Example 1 were dissolved in 15 ml of tetrahydro-furan, added dropwise to the Grignard reagent while cooling in an ice bath, and stirred for 15 hours at RT. The reaction solution was worked up by adding 30 ml of saturated anmonium chloride solution while cooling in an ice bath, and was extracted three times at RT with in each case 60 ml of ethyl acetate. The combined organic extracts were dried over sodium sulfate, filtered, and concentrated by evaporation on a rotary evaporator (500 to 10 mbar). 5.17 g of crude base (108% of theory) were obtained. 4.43 g of 1-(2,5-dimethoxy-phenyl)-2-(dimethylaminophenylmethyl)cyclohexanol, hydrochloride (84.2% of theory) with a melting point above 240° C. were obtained from the crude base according to the procedure described in Example 1 ($3^{rd}$ stage) with chlorotri-methylsilane/water in 2-butanone.

Example 27

1-(2-chloro-4-fluorobenzyl)-2-(dimethylaminophenylmethyl)cyclohexanol, hydrochloride 0.38 g (15.6 mmole) of magnesium turnings was stirred in 10 ml of ether of analysis purity. 2.79 g (15.6 mmole) of 2-chloro-4-fluorobenzyl bromide dissolved in 10 ml of ether were added dropwise so that the reaction mixture boiled gently. After completion of the addition the reaction mixture was stirred for a further hour at RT. 3.0 g (13.0 mmole) of the 2-(dimethyl-aminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation on a rotary evaporator (500 to 10 mbar). 4.52 g of crude base (92.8% of theory) were obtained. The crude base was dissolved in 45 ml of 2-butanone and some ethyl acetate, 0.11 ml (6.0 mmole) of water and 1.52 ml (12.0 mmole) of chlorotrimethylsilane were added in succession, and the reaction mixture was kept for 15 hours at RT. The solvents were distilled off on a rotary evaporator (500 to 10 mbar), the residue was taken up in 20 ml of ether, the remaining solids were filtered off, washed with small portions of ether, and dried to constant weight in an oil pump vacuum. 4.45 g of 1-(2-chloro-4-fluorobenzyl)-2-(dimethylaminophenylmethyl)cyclohexanol, hydrochloride (83.2% of theory) were obtained in this way. The hydrochloride decomposes on heating above 100° C.

Example 28

1-(4-tert.-butylbenzyl)-2-(dimethylaminophenylmethyl)cyclohexanol, hydrochloride 0.33 g (13.5 mmole) of magnesium turnings was stirred in 10 ml of ether of analysis purity. 2.46 g (13.5 mmole) of 4-tert.butylbenzyl chloride dissolved in 10 ml of ether were added dropwise so that the reaction mixture boiled gently. After completion of the addition the reaction mixture was stirred for a further hour at RT. 3.0 g (13.0 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation on a rotary evaporator (500 to 10 mbar). 4.18 g of crude base (98.1% of theory) were obtained. 2.16 g of 1-(4-tert.-butylbenzyl)-2-(dimethylaminophenylmethyl) cyclohexanol, hydrochloride (46.2% of theory) with a melting point of 227–229° C. were obtained from the crude base according to the procedure described in Example 1 ($3^{rd}$ stage) with chlorotrimethylsilane/water in 2-butanone.

Example 29

2-(dimethylaminophenylmethyl)-1-(3-fluorobenzyl) cyclohexanol, hydrochloride 0.38 g (15.6 mmole) of magnesium turnings was stirred in 10 ml of ether of analysis purity. 1.89 g (15.6 mmole) of 3-fluorobenzyl bromide dissolved in 10 ml of ether were added dropwise so that the reaction mixture boiled gently. After completion of the addition the reaction mixture was stirred for a further hour at RT. 3.0 g (13.0 mmole) of the 2-(dimethyl-aminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation on a rotary evaporator (500 to 10 mbar). 4.59 of crude base (104% of theory) were obtained, from which a hydrochloride was precipitated according to the procedure of Example 1 ($3^{rd}$ stage) with chlorotrimethylsilane/water in 2-butanone. The base was treed from the hydrochloride with 40 ml of water and 5 ml of caustic soda (32 m %), extracted three times, each time with 40 ml of ether, and the combined organic extracts were dried over sodium sulfate, filtered, and concentrated by evaporation on a rotary evaporator (500 to 10 mbar). 3.42 g of crude base (77.2% of theory) were obtained. 2.72 g of 2-(dimethylaminophenylmethyl)-1-(3-fluorobenzyl)cyclohexanol, hydrochloride (55.5% of theory) with a melting point of 146–147° C. were obtained from the crude base according to the procedure described in Example 1 ($3^{rd}$ stage) with chlorotrimethylsilane/water in 2-butanone.

Example 30

1-(2-chlorobenzyl)-2-(dimethylaminophenylmetlhyl)cyclohexanol, hydrochloride 0.38 g (15.6 mmole) of magnesium turnings was stirred in 15 ml of ether of analysis purity. 2.0 ml (15.6 mmole) of 2-chlorobenzyl chloride dissolved in 15 ml of ether were added dropwise so that the reaction mixture boiled gently. After completion of the addition the reaction mixture was stirred for a further hour at RT. 3.0 g (13.0 mmole) of the 2-(dimethylaminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation on a rotary evaporator (500 to 10 mbar). 4.50 g of crude base (97.0% of theory) were obtained, from which a hydrochloride was precipitated according to Example 1 ($3^{rd}$ stage) with chlorotrimethylsilane/water in 2-butanone. The base was freed from the hydrochloride with 40 ml of water and 5 ml of caustic soda (32 m %), extracted three times, each time with 40 ml of ether, and the combined organic extracts were dried over sodium sulfate, filtered, and concentrated by evaporation on a rotary evaporator (500 to 10 mbar). 2.90 g of crude base were obtained, which were added to a 3.5×15 cm column filled with silica gel. Elution with ethyl acetate/n-hexane (2:5) yielded 1.59 g of base, from which 1.75 g of 1-(2-chlorobenzyl)-2-(dimethylaminophenylmethyl)cyclohexanol, hydrochloride (34.2% of theory) were obtained according to the procedure described in Example 1 (3rd stage) with chlorotrimethylsilane/water in 2-butanone. The hydrochloride decomposes on heating above 130° C.

Example 31

1-benzo[1,3]dioxol-5-yl-2-[dimethylamino-(3-methoxyphenyl)methyl]cyclohexanol, hydrochloride 2.61 g (13.0 mmole) of 4-bromo-1,2-methylenedioxybenzene were dissolved in 10 ml of tetrahydrofuran and cooled to −70° C. under nitrogen in a dry ice/isopropanol bath. 7.9 ml (13.0 mmole) of n-butyllithium (1.6 M in hexane) were added dropwise while stirring so that the temperature did not rise above −60° C. The reaction mixture was stirred for a further 30 minutes and then 3.0 g (10.8 mmole) of the 2-[dimethylamino-(3-methoxyphenyl)methyl]cyclohexanone prepared according to Example 9 and dissolved in 10 ml of tetrahydrofuran were added dropwise while cooling in an ice bath, and the whole was heated to RT within two hours. The reaction mixture was worked up by adding 20 ml of saturated ammonium chloride solution while cooling in an ice bath, and was extracted three times at RT, each time with 20 ml of ethyl acetate. The combined organic extracts were dried over sodium sulfate, filtered, and concentrated by evaporation on a rotary evaporator (500 to 10 mbar). 4.10 g of crude base (98.8% of theory) were obtained, from which 1.96 g of 1-benzo[1,3]dioxol-5-yl-2-[dimethylamino-(3-methoxyphenyl)methyl]cyclohexanol, hydrochloride (43.2% of theory) were obtained according to the procedure described in Example 1 ($3^{rd}$ stage) with chlorotrimethylsilane/water in 2-butanone. The hydrochloride decomposes on heating above 109° C.

Example 32

1-(3-chlorobenzyl)-2-(dimethylaminophenylmethyl)cyclohexanol, hydrochloride 0.38 g (15.6 mmole) of magnesium turnings was stirred in 15 ml of ether of analysis purity. 2.0 ml (15.6 mmole) of 3-chlorobenzyl chloride dissolved in 15 ml of ether were added dropwise so that the reaction mixture boiled gently. After completion of the addition the reaction mixture was stirred for a further hour at RT. 3.0 g (13.0 mmole) of the 2-(dimethyl-aminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation on a rotary evaporator (500 to 10 mbar). 4.55 of crude base (98.0% of theory) were obtained, from which a hydrochloride was precipitated according to Example 1 ($3^{rd}$ stage) with chlorotrimethylsilane/water in 2-butanone. The base was freed from the hydrochloride with 40 ml of water and 5 ml of caustic soda (32 m %), extracted three times, each time with 40 ml of ether, and the combined organic extracts were dried over sodium sulfate, filtered, and concentrated by evaporation on a rotary evaporator (500 to 10 mbar). 2.87 g of crude base were obtained, to which were added 5 ml of ethyl acetate-hexane in a ratio of 2:5. The insoluble residue was filtered off and dried. 2.11 g of base was obtained, from which 1.68 g of 1-(3-chlorobenzyl)-2-(dimethylaminophenylmethyl)cyclohexanol, hydrochloride (32.8% of theory) with a melting point of 185° C.–188° C. was precipitated according to the procedure described in Example 1 ($3^{rd}$ stage) with chlorotrimethylsilane/water in 2-butanone.

Example 33

1-(2,4-dichlorobenzyl)-2-(dimethylaminophenylmethyl)cyclohexanol, hydrochloride 0.38 g (15.6 mmole) of magnesium turnings was stirred in 10 ml of ether of analysis purity. 3.04 g (15.6 mmole) of 2,4-dichlorobenzyl chloride dissolved in 10 ml of ether were added dropwise so that the reaction mixture boiled gently. After completion of the addition the reaction mixture was stirred for a further hour at RT. 3.0 g (13.0 mmole) of the 2-(dimethylaminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, each time with 60 ml of ethyl acetate. The combined organic extracts were dried over sodium sulfate, filtered, and concentrated by evaporation on a rotary evaporator (500 to 10 mbar). 2.14 g of crude base (97.0% of theory) were obtained, from which a hydrochloride was precipitated according to Example 1 ($3^{rd}$ stage) with chlorotrimethylsilane/water in 2-butanone. The base was freed from the hydrochloride with 20 ml of water and 3 ml of caustic soda (32 m %), extracted three times, each time with 20 ml of ether, and the combined organic extracts were dried over sodium sulfate, filtered, and concentrated by evaporation on a rotary evaporator (500 to 10 mbar). 1.19 g of crude base were obtained, from which 0.45 g of 1-(2,4-dichlorobenzyl)-2-(dimethylaminophenylmethyl) cyclohexanol, hydrochloride (8.1% of theory) was obtained according to the procedure described in Example 1 ($3^{rd}$ stage) with chlorotri-methylsilane/water in 2-butanone. The hydrochloride decomposes on heating above 140° C.

Example 34

1-benzyl-2-[dimethylaminophenyl-(3-phenoxyphenyl)methyl]cyclohexanol, hydrochloride $1^{st}$ Stage 2-[dimethylamino-(3-phenoxyphenyl)methyl]cyclohexanone 2.47 g (30.3 mmole) of freshly dried dimethylamine hydrochloride were added while stirring to 67 ml (66.6 mmole) of sodium iodide solution (1 M in acetonitrile) cooled in an ice bath to 0° C., following which 8.4 ml (60.5 mmole) of triethylamine and 8.4 ml (66.6 mmole) of chlorotrimethylsilane were added dropwise, and the whole was stirred for a further hour at RT. 6.0 ml (30.3 mmole) of 3-phenoxybenzaldehyde were added to the reaction mixture while cooling in an ice bath, and the whole was stirred for a further hour at RT. The reaction mixture was cooled again to 0° C. in an ice bath, and 4.58 g (30.3 mmole) of 1-(pyrrolidino)-1-cyclohexene were added and the whole was stirred for a further two hours at RT. The reaction mixture was worked up by adding 45 ml of semi-concentrated hydrochloric acid while cooling in an ice bath, stirred for 10 minutes, washed twice each time with 45 ml of ether, and adjusted in the alkaline range (pH ca. 9) with 115 ml of dilute ammonia solution (5 vol. %)). The reaction mixture was extracted three times, each time with 45 ml of ether, and the combined organic extracts were dried over sodium sulfate, filtered, and concentrated by evaporation on a rotary evaporator (500 to 10 mbar) without heating. 7.41 g of crude base (75.7% of theory) were obtained in this way. 4.83 g of the hydrochloride of 2-[dimethylamino-(3-phenoxyphenyl)methyl]cyclohexanone (44.4% of theory) were obtained from the crude base according to the procedure described in Example 1 ($2^{nd}$ stage) with chlorotrimethylsilane/water in 2-butanone.

$2^{nd}$ Stage 1-benzyl-2-[dimethylaminophenyl-(3-phenoxyphenyl) methyl]cyclohexanol, hydrochloride 0.27 g (11.1 mmole) of magnesium turnings was stirred in 5 ml of ether of analysis purity. 1.90 g (11.1 mmole) of benzyl bromide dissolved in 10 ml of ether were added dropwise so that the reaction mixture boiled gently. After completion of the addition the reaction mixture was stirred for a further hour at RT. The base was freed with 30 ml of water and 5 ml of ammonia solution (25 vol. %) from 3.7 g (11.4 mmole) of the hydrochloride of 2-[dimethylaminophenyl-(3-phenoxyphenyl) methyl] cyclohexanone obtained from stage 1, was extracted three times, each time with 30 ml of ether, and the combined organic extracts were dried over sodium sulfate, filtered, and concentrated by evaporation on a rotary evaporator without heating (500 to 10 mbar). 3.0 g (9.3 mmole) of this base were dissolved in 10 ml of ether, added dropwise to the Grignard reagent while cooling in an ice bath, and stirred for 15 hours at RT. The reaction mixture was worked up by adding 15 ml of saturated ammonium chloride solution while cooling in an ice bath, and was extracted three times at RT, each time with 15 ml of ether. The combined organic extracts were dried over sodium sulfate, filtered, and concentrated by evaporation on a rotary evaporator (500 to 10 mbar). 3.51 g of crude base (91.1% of theory) were obtained, from which a hydrochloride was precipitated according to Example 1 (3rd stage) with chlorotrimethylsilane/water in 2-butanone. The base was freed from the hydrochloride with 30 ml of water and 5 ml of ammonia solution (25 vol. %), extracted three times, each time with 15 ml of ether, and the combined organic extracts were dried over sodium sulfate, filtered, and concentrated by evaporation on a rotary evaporator (500 to 10 mbar). 2.55 g of crude base (65.9% of theory) were obtained, which were added to a 5×33 cm column filled with silica gel. Elution with ethyl acetate/n-hexane in a ratio of 1:4 yielded 1.92 g of base, from which 0.51 g of 1-benzyl-2-[dimethylamino-phenyl-(3-phenoxyphenyl)methyl]cyclohexanol, hydrochloride (12.1% of theory) with a melting point of 189–190° C. was obtained according to the procedure described in Example 1 (3rd stage) with chlorotrimethylsilanie/water in 2-butanone.

Example 35

1-benzyl-2-[dimethylaminophenyl-(3-methoxyphenyl)methyl]cyclohexanol, hydrochloride 0.32 g (13.0 mmole) of magnesium turnings was stirred in 10 ml of ether of analysis purity. 2.22 g (13.0 mmole) of benzyl bromide dissolved in 10 ml of ether were added dropwise so that the reaction mixture boiled gently. After completion of the addition the reaction mixture was stirred for a further hour at RT. 3.0 g (10.8 mmole) of the 2-[dimethylaminophenyl-(3-methoxyphenyl)methyl] cyclohexanone prepared according to Example 9 were dissolved in 10 ml of ether, added dropwise to the Grignard reagent while cooling in an ice bath, and stirred for 15 hours at RT. The reaction mixture was worked up by adding 15 ml of saturated anmonium chloride solution while cooling in an ice bath, and was extracted three times at RT, with in each case 15 ml of ether. The combined organic extracts were dried over sodium sulfate, filtered, and concentrated by evaporation on a rotary evaporator (500 to 10 mbar). 3.58 g of crude base (93.7% of theory) were obtained, from which a hydrochloride was precipitated according to Example 1 ($3^{rd}$ stage) with chlorotrimethylsilane/water in 2-butanone. The base was freed from the hydrochloride with 30 ml of water and 5 ml of ammonia solution (25 vol. %), extracted three times, each time with 15 ml of ether, and the combined organic extracts were dried over sodium sulfate, filtered, and concentrated by evaporation on a rotary evaporator (500 to 10 mbar). 3.2 g of crude base (76.2% of theory) were obtained, which were added to a 5×33 cm column filled with silica gel. Elution with ethyl acetate/n-hexane in a ratio of 1:4 yielded 1.69 g of base, from which 1.60 g of 1-benzyl-2-[dimethylaminophenyl-(3-methoxyphenyl)methyl] cyclohexanol, hydrochloride (38.0% of theory) having a melting point range of 101° C.–115° C. were obtained according to Example 1 (3$^{rd}$ stage) with chlorotrimethylsilane/water in 2-butanone.

Example 36

2-(dimethylaminophenylmethyl)-1-(3-trifluoromethylbenzyl)cyclohexanol, hydrochloride 0.33 g (13.5 mmole) of magnesium turnings was stirred in 10 ml of ether of analysis purity. 2.62 g (13.5 mmole) of 3-chloromethylbenzotrifluoride dissolved in 10 ml of ether were added dropwise so that the reaction mixture boiled gently. After completion of the addition the reaction mixture was stirred for a further hour at RT. 2.60 g (11.2 mmole) of the 2-(dimethylaminophenylmethyl)cyclohexaione prepared according to Example 1 were dissolved in 15 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT, with in each case 60 ml of ethyl acetate. The combined organic extracts were dried over sodium sulfate, filtered, and concentrated by evaporation on a rotary evaporator (500 to 10 mbar). 4.49 g of crude base (104% of theory) were obtained, from which a hydrochloride was precipitated according to Example 1 (3$^{rd}$ stage) with chlorotrimethylsilane/water in 2-butanone. The base was freed from the hydrochloride with 30 ml of water and 5 ml of ammonia solution (25 vol. %), extracted three times, each time with 30 ml of ether, and the combined organic extracts were dried over sodium sulfate, filtered, and concentrated by evaporation on a rotary evaporator (500 to 10 mbar). 3.49 g of crude base were obtained, from which 1.80 g of 2-(dimethylaminophenylmethyl)-1-(3-trifluoromethylbenzyl)cyclohexanol, hydrochloride (37.4% of theory) with a melting point of 184° C.–186° C. were obtained according to Example 1 (3$^{rd}$ stage) with chlorotrimethylsilane/water in 2-butanone.

Example 37

2-(dimethylamino-(3-methoxyphenyl)methyl]-1-(3-methoxybenzyl)cyclohexanol, hydrochloride 0.32 g (13.0 mmole) of magnesium turnings was stirred in 10 ml of ether of analysis purity. 2.61 g (13.0 mmole) of 3-methoxybenzyl bromide dissolved in 10 ml of ether were added dropwise so that the reaction mixture boiled gently. After completion of the addition the reaction mixture was stirred for a further hour at RT. 3.0 g (10.8 mmole) of the 2-[dimethyl-amino-(3-methoxyphenyl)methyl] cyclohexanone prepared according to Example 9 were dissolved in 10 ml of ether, added dropwise to the Grignard reagent while cooling in an ice bath, and stirred for 15 hours at RT. The reaction mixture was worked up by adding 15 ml of saturated ammonium chloride solution while cooling in an ice bath, and was extracted three times at RT, each time with 15 ml of ether. The combined organic extracts were dried over sodium sulfate, filtered, and concentrated by evaporation on a rotary evaporator (500 to 10 mbar). 3.87 g of crude base (101% of theory) were obtained, from which a hydrochloride was precipitated according to Example 1 (3$^{rd}$ stage) with chlorotrimethylsilane/water in 2-butanone. The base was freed from the hydrochloride with 30 ml of water and 5 ml of ammonia solution (25 vol. %), extracted three times, each time with 15 ml of ether, and the combined organic extracts were dried over sodium sulfate, filtered, and concentrated by evaporation on a rotary evaporator (500 to 10 mbar). 2.34 g of crude base (61.2% of theory) were obtained, from which 2.04 g of 2-[dimethylamino-(3-methoxyphenyl)methyl]-1-(3-methoxybenzyl) cyclohexanol, hydrochloride (48.4% of theory) were obtained according to Example 1 (3$^{rd}$ stage) with chlorotrimethylsilane/water in 2-butanone. The hydrochloride decomposes on heating above 75° C.

Example 38

2-[(2-chlorophenyl)dimethylaminomethyl]-1-naphthalene-2-ylcyclohexanol, hydrochloride 1$^{st}$ Stage

2-[(2-chlorophenyl)dimethylaminomethyl]cyclohexanone 17.4 g (213 mmole) of freshly dried dimethylamine hydrochloride were added while stirring to 471 ml (469 mmole) of sodium iodide solution (1 M in acetonitrile) cooled to 0° C. in an ice bath, followed by the dropwise addition of 60 ml (427 mmole) of triethylamine and 60 ml (469 mmole) of chlorotrimethylsilane, and the whole was stirred for one hour at RT. 24 ml (213 mmole) of 2-chlorobenzaldehyde were added while cooling in an ice bath, and the reaction mixture was stirred for a further hour at RT. The reaction mixture was cooled once more to 0° C. in an ice bath, following which 34 ml (213 mmole) of 1-(pyrrolidino)-1-cyclohexene were added, and the whole was stirred for a further two hours at RT. The reaction mixture was worked up by adding 300 ml of semi-concentrated hydrochloric acid while cooling with ice, stirring for 10 minutes, washing twice, each time with 300 ml of ether, and then adjusting to the alkaline range (pH ca. 9) with 770 ml of dilute ammonia solution (5 vol. %). The reaction mixture was extracted three times, each time with 300 ml of ether, and the combined organic extracts were dried over sodium sulfate, filtered, and concentrated by evaporation on a rotary evaporator (500 to 10 mbar) without heating. 38.3 g of crude base (67.5% of theory) were obtained in this way. 33.6 g of the hydrochloride of 2-[(2-chlorophenyl)dimethylaminomethyl]cyclohexanone (52.0% of theory) were obtained from the crude base according to the procedure described in Example 1 (2$^{nd}$ stage) with chlorotrimethylsilane/water in 2-butanone.

2$^{nd}$ Stage

2-[(2-chlorophenyl)dimethylaminomethyl]-1-naphthalene-2-ylcyclohexanol, hydrochloride 0.27 g (11.1 mmole) of magnesium turnings was stirred in 5 ml of ether of analysis purity. 2.32 g (11.1 mmole) of 2-bromonaphthalene dissolved in 10 ml of ether were added dropwise so that the reaction mixture boiled gently. After completion of the addition the reaction mixture was stirred for one hour at RT. The base was freed from 3.0 g (11.2 mmole) of the hydrochloride of 2-[(2-chlorophenyl)dimethylaminomethyl]cyclohexanone obtained according to stage 1 with 30 ml of water and 5 ml of ammonia solution (25 vol. %), extracted three times, each time with 30 ml of ether, and the combined organic extracts were dried over sodium sulfate, filtered, and concentrated by evaporation on a rotary evaporator without heating (500 to 10 mbar). 2.50 g (9.3 mmole) of this base were dissolved in 10 ml of ether, added dropwise to the Grignard reagent while cooling in an ice bath, and stirred for 15 hours at RT. The reaction mixture was worked up by adding 15 ml of saturated ammonium chloride solution while cooling in an ice bath and was extracted three times at RT, each time with 15 ml of ether. The combined organic extracts were dried over sodium sulfate, filtered, and concentrated by evaporation on a rotary evaporator (500 to 10 mbar). 4.05 g of crude base (110% of theory) were obtained, from which a hydrochloride was precipitated according to Example 1 ($3^{rd}$ stage) with chlorotrimethylsilane/water in 2-butanone. The base was freed from the hydrochloride with 30 ml of water and 5 ml of ammonia solution (25 vol. %), extracted three times, each time with 15 ml of ether, and the combined organic extracts were dried over sodium sulfate, filtered, and concentrated by evaporation on a rotary evaporator (500 to 10 mbar). 2.2 g of crude base (60.0% of theory) were obtained, which were added to a 3×26 cm column filled with silica gel. Elution with ethyl acetate-hexane (1:4) yielded 0.95 g of base, from which 0.47 g of 2-[(2-chlorophenyl)dimethylaminomethyl]-1-naphthalene-2-ylcyclohexanol, hydrochloride (11.3% of theory) with a melting point above 230° C. were obtained according to the procedure described in Example 1 ($3^{rd}$ Stage) with chlorotrimethylsilane/water in 2-butanone.

Example 39

1-benzyl-2-[(3,4-dichlorophenyl) dimethylaminomethyl]cyclohexanol, hydrochloride $1^{st}$ Stage 2-[(3,4-dichlorophenyl)dimethylaminomethyl] cyclohexanone 7.92 g (97.1 mmole) of freshly dried dimethylamine hydrochloride were added while stirring to 214 ml (214 mmole) of sodium iodide solution (1 M in acetonitrile) cooled to 0° C. with an ice bath, followed by the dropwise addition of 27 ml (194 mmole) of triethylamine and 27 ml (214 mmole) of chlorotrimethylsilane, and the whole was stirred for a further hour at RT. 17.0 g (97.1 mmole) of 3,4-dichlorobenzaldehyde were added while cooling with ice, and the whole was stirred for a further hour at RT. The reaction mixture was cooled again to 0° C. with an ice bath, following which 14.7 g (97.1 mmole) of 1-(pyrrolidino)-1-cyclohexene were added, and the whole was stirred for a further two hours at RT. The reaction mixture was worked up by adding 130 ml of semi-concentrated hydrochloric acid, stirred for 10 minutes, washed twice with in each case 125 ml of ether, and adjusted in the alkaline range (pH ca. 9) with 300 ml of dilute ammonia solution (5 vol. %). The reaction mixture was extracted three times with 125 ml of ether each time, and the combined organic extracts were dried over sodium sulfate, filtered, and concentrated by evaporation on a rotary evaporator (500 to 10 mbar) without heating. 26.6 g of crude base (91% of theory) were obtained in this way. 26.7 g of the hydrochloride of 2-[(3,4-dichlorophenyl) dimethylaminomethyl]cyclohexanone (81.8% of theory) were obtained from the crude base according to the procedure described in Example 1 ($2^{nd}$ stage) with chlorotrimethylsilane/water in 2-butanone.

$2^{nd}$ Stage 1-benzyl-2-[(3,4-dichlorophenyl)dimethylaminomethyl] cyclohexanol, hydrochloride The base was freed from 3.5 g (10.4 mmole) of the hydrochloride of 2-[(3,4-dichlorophenyl) dimethylaminomethyl]cyclohexanone obtained according to stage 1 with 30 ml of water and 10 ml of ammonia solution (25 vol. %), extracted three times, each time with 30 ml of ether, and the combined organic extracts were dried over sodium sulfate, filtered, and concentrated by evaporation on a rotary evaporator without heating (500 to 10 mbar). 3.0 g (10.0 mmole) of this base were dissolved in 10 ml of tetrahydrofuran, added dropwise while cooling with an ice bath to 6.0 ml (12.0 mmole) of benzylmagnesium chloride (2 M solution in tetrahydrofuran), and stirred for 15 hours at RT. The reaction mixture was worked up by adding 15 ml of saturated ammonium chloride solution while cooling in an ice bath, and was extracted three times at RT, each time with 15 ml of ether. The combined organic extracts were dried over sodium sulfate, filtered, and concentrated by evaporation on a rotary evaporator (500 to 10 mbar). 3.05 g of crude base (77.9% of theory) were obtained, from which 2.88 g of 1-benzyl-2-[(3,4-dichlorophenyl)dimethylaminomethyl] cyclohexanol, hydrochloride (67.1% of theory) were obtained according to the procedure described in Example 1 ($3^{rd}$ Stage) with chlorotrimethylsilane/water in 2-butanone. The hydrochloride decomposes on heating above 200° C.

Example 40

2-[(3,4-dichlorophenyl)dimethylaminomethyl]-1-phenethylcyclohexanol, hydrochloride 3.0 g (10.0 mmole) of the 2-[(3,4-dichlorophenyl) dimethylaminomethyl]cyclohexanone prepared according to Example 39 were dissolved in 10 ml of tetrahydrofuran, added dropwise while cooling in an ice bath to 12.0 ml (12.0 mmole) of phenethylmagnesium chloride (1 M solution in tetrahydrofuran) and stirred for 15 hours at RT. The reaction solution was worked up by adding 15 ml of saturated ammonium chloride solution while cooling in an ice bath, and was extracted three times at RT with in each case 15 ml of ether. The combined organic extracts were dried over sodium sulfate, filtered and concentrated by evaporation on a rotary evaporator (500 to 10 mbar). 3.88 g of crude base (95.5% of theory) were obtained from which, after adding 30 ml of n-hexane, an oil was obtained according to the procedure described in Example 1 ($3^{rd}$ Stage) with chlorotrimethylsilane/ water in 2-butanone. After decanting the solvents the oil was stirred in 5 ml of water and 20 ml of ether, arid the resultant precipitate was filtered off and dried. 3.04 g of 2-[(3,4-dichlorophenyl) dimethylaminomethyl]-1-phenethylcyclo-hexanol, hydrochloride (68.7% of theory) were obtained in this way. The hydrochloride decomposes on heating above 130° C.

Example 41

1-benzyl-2-[dimethylamino-(4-fluorophenyl)methyl] cyclohexanol, hydrochloride $1^{st}$ Stage 2-[dimethylamino-(4-fluorophenyl)methyl]cyclohexanone 19.7 g (242 mmole) of freshly dried dimethylamine hydrochloride were added while stirring to 532 ml (532 mmole) of sodium iodide solution (1 M in acetonitrile) cooled to 0° C. with an ice bath, followed by the dropwise addition of 67 ml (483 mmole) of triethylamine and 67 ml (532 mmole) of chlorotrimethylsilane, and the whole was stirred for a further hour at RT. 30.0 g (242 mmole) of 4-fluorobenzaldehyde were added while cooling with ice, and the whole was stirred for a further hour at RT. the reaction mixture was cooled again to 0° C. with an ice bath, 36.6 g (242 mmole) of 1-(pyrrolidino)-1-cyclohexene were added, and the whole was stirred for a further two hours at RT. The reaction mixture was worked up by adding 300 ml of semi-concentrated hydrochloric acid, while cooling with ice, stirred for 10 minutes, washed twice with in each case 250 ml of ether, and adjusted to the alkaline range (pH ca. 9) with 750 ml of dilute ammonia solution (5 vol. %). The reaction mixture was extracted three times with 250 ml of ether each time, and the combined organic extracts were dried over sodium sulfate, filtered, and concentrated by a rotary evaporator (500 to 10 mbar) without heating. 51.0 g of crude base (84.6% of theory) were obtained in this way.

41.7 g of the hydrochloride of 2-[dimethylamino-(4-fluorophenyl)methyl]cyclohexanone (60.3% of theory) were obtained from the crude base according to the procedure described in Example 1 ($2^{nd}$ stage) with chlorotrimethylsilane/water in 2-butanone.

$2^{nd}$ Stage 1-benzyl-2-[dimethylamino-(4-fluorophenyl)methyl]cyclohexanol, hydrochloride The base was freed from 3.2 g (11.2 mmole) of the hydrochloride of 2-[dimethylamino-(4-fluorophenyl)methyl]cyclohexanone obtained according to stage 1 with 30 ml of water and 10 ml of ammonia solution (25 vol. %), extracted three times with 30 ml of ether each time, and the combined organic extracts were dried over sodium sulfate, filtered, and concentrated by evaporation on a rotary evaporator without heating (500 to 10 mbar). 2.69 g (10.8 mmole) of this base were dissolved in 10 ml of tetrahydrofuran, added dropwise while cooling in an ice bath to 6.5 ml (12.9 mmole) of benzylmagnesium chloride (2 M solution in tetrahydrofuran), and the whole was stirred for 15 hours at RT. The reaction mixture was worked up by adding 15 ml of saturated ammonium chloride solution while cooling in an ice bath and was extracted three times at RT, with 15 ml of ether each time. The combined organic extracts were dried over sodium sulfate, filtered, and concentrated by evaporation on a rotary evaporator (500 to 10 mbar). 3.42 g of crude base (84.1% of theory) were obtained, from which a hydrochloride was precipitated according to Example 1 ($3^{rd}$ stage) with chlorotrimethylsilane/water in 2-butanone. The base was freed from the hydrochloride with 30 ml of water and 5 ml of ammonia solution (25 vol. %), extracted three times with 15 ml of ether each time, and the combined organic extracts were dried over sodium sulfate, filtered, and concentrated by evaporation on a rotary evaporator (500 to 10 mbar). 2.89 g of crude base (78.6% of theory) were obtained, from which 2.58 g of 1-benzyl-2-[dimethylamino-(4-fluorophenyl)methyl]cyclohexanol, hydrochloride (63.3% of theory) having a melting point of 178° C. were obtained according to the procedure described in Example 1 ($3^{rd}$ stage) with chlorotrimethylsilane/water in 2-butanone.

Example 42

2-[(3-chlorophenyl)(dimethylaminomethyl]-1-phenylcyclohexanol, hydrochloride $1^{st}$ Stage 2-[(3-chlorophenyl)(dimethylaminomethyl]cyclohexanone 3.48 g (42.7 mmole) of freshly dried dimethylamine hydrochloride were added while stirring to 94 ml (94 mmole) of sodium iodide solution (1 M in acetonitrile), cooled to 0° C. with an ice bath, followed by the dropwise addition of 12 ml (85.4 mmole) of triethylamine and 12 ml (94 mmole) of chlorotrimethylsilane, and the whole was stirred for a further hour at RT. 4.8 ml (42.7 mmole) of 3-chlorobenzaldehyde were added while cooling with ice, and the whole was stirred for a further hour at RT. The reaction mixture was cooled again to 0° C. with an ice bath, 6.9 ml (42.7 mmole) of 1-(pyrrolidino)-1-cyclohexene were added, and the whole was stirred for a further two hours at RT. The reaction mixture was worked up by adding 60 ml of semi-concentrated hydrochloric acid, stirred for 10 minutes, washed twice with 60 ml of ether each time, and adjusted in the alkaline range (pH ca. 9) with 150 ml of dilute ammonia solution (5 vol. %). The reaction mixture was extracted three times with 60 ml of ether each time, and the combined organic extracts were dried over sodium sulfate, filtered, and concentrated by evaporation on a rotary evaporator without heating (500 to 10 mbar). 8.97 g of crude base (79.1% of theory) were obtained, from which a hydrochloride was precipitated according to Example 1 ($3^{rd}$ stage) with chlorotrimethylsilane/water in 2-butanone. The base was freed from the hydrochloride with 90 ml of water and 15 ml of ammonia solution (25 vol. %), extracted three times with 50 ml of ether each time, and the combined organic extracts were dried over sodium sulfate, filtered, and concentrated by evaporation on a rotary evaporator without heating (500 to 10 mbar). 7.05 g of crude base (62.1% of theory) were obtained, from which 7.38 g of the hydrochloride of 2-[(3-chlorophenyl)(dimethylaminomethyl]cyclohexanone (57.2% of theory) were obtained according to the procedure described in Example 1 (2nd stage) with chlorotrimethylsilane/water in 2-butanone.

$2^{nd}$ Stage

2-[(3-chlorophenyl)(dimethylaminomethyl]-1-phenylcyclohexanol, hydrochloride

The base was freed from 2.5 g (8.27 mmole) of the hydrochloride of 2-[(3-chlorophenyl)(dimethylaminomethyl]cyclohexanone obtained according to stage 1 with 30 ml of water and 5 ml of ammonia solution (25 vol. %), extracted three times with 30 ml of ether each time, and the combined organic extracts were dried over sodium sulfate, filtered, and concentrated by evaporation on a rotary evaporator without heating (500 to 10 mbar). 2.0 g (7.5 mmole) of this base were dissolved in 5 ml of tetrahydrofuran, added dropwise while cooling in an ice bath to 4.5 ml (9.0 mmole) of phenylmagnesium chloride (2 M solution in tetrahydro-furan), and the whole was stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 2.30 g of crude base (88.8% of theory) were obtained, from which 2.18 g of 2-[(3-chlorophenyl)dimethylaminomethyl]-1-phenylcyclohexanol, hydrochloride (76.2% of theory) were obtained according to the procedure described in Example 1 ($3^{rd}$ stage) with chlorotrimethylsilane/water in 2-butanone. The hydrochloride decomposes on heating above 139° C.

Example 43

1-(2,4-dichlorophenyl)-2-(3-dimethylaminomethyl)-1-cyclohexanol, hydrochloride 0.76 g (31.2 mmole) of magnesium turnings was stirred in 10 ml of ether of analysis purity. A mixture of 1.34 ml (15.6 mmole) of dibromomethanie and 3.52 g of 1-bromo-2,4-dichlorobenzene dissolved in 10 ml of ether was added dropwise so that the reaction mixture boiled gently. After completion of the addition the reaction mixture was stirred for a further hour at RT. 3.0 g (15.6 mmole) of the 2(dimethylaminophenylmethyl) cyclohexanone prepared according to Example 1 were dissolved in 10 ml of ether, added dropwise while cooling in an ice bath to the Grignard reagent, and the whole was stirred for 15 hours at RT. The reaction mixture was worked up by adding 20 ml of saturated ammonium chloride solution while cooling in an ice bath, and was extracted three times at RT with 50 ml of ethyl acetate each time. The combined organic extracts were dried over sodium sulfate, filtered, and concentrated by evaporation on a rotary evaporator (500 to 10 mbar). 4.92 g of crude base (100% of theory) were obtained, from which a hydrochloride was precipitated according to Example 1 ($3^{rd}$ stage) with chlorotrimethylsilane/water in 2-butanone. The base was freed from the hydrochloride with 40 ml of water and 5 ml of caustic soda (32 m %), extracted three times, each time with 40 ml of ether, and the combined organic extracts were dried over sodium sulfate, filtered, and concentrated by evaporation on a rotary evaporator (500 to 10 mbar). 4.53 g of crude base were obtained, which were added to a 3.5×30 cm column filled with silica gel. Elution with ethyl acetate/ n-hexane (1:4) yielded 2.74 g of base, from which 2.46 g of 1-(2,4-dichloroplhenyl)-2-(3-diinethylaminomethyl)-1-cyclohexanol, hydrochloride (45.6%, of theory) having a melting point of 192° C.–195° C. were obtained according to the procedure described in Example 1 ($3^{rd}$ Stage) with chlorotrimethylsilane/water in 2-butanone.

Example 44

1-benzyl-2-[(3-chlorophenyl)dimethylaminomethyl] cyclohexanol, hydrochloride 2.0 g (7.5 mmole) of the 2-[(3-chlorophenyl) dimethylaminomethyl]cyclohexanone prepared according to Example 42 were dissolved in 10 ml of tetrahydrofuran, added dropwise while cooling in an ice bath to 4.5 ml (9.0 mmole) of benzylmagnesium chloride (2 M solution in tetrahydrofuran) and stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 2.61 g of crude base (97.0% of theory) were obtained, from which 1.24 g of 1-benzyl-2-[(3-chlorophenyl)dimethylaminomethyl]cyclohexanol hydrochloride (41.8% of theory) having a melting point of 161° C.–163° C. were obtained according to the procedure described in Example 1 ($3^{rd}$ Stage) with chlorotrimethylsilane/water in 2-butanone.

Example 45

1-benzyl-2-[(2-chlorophenyl)dimethylaminomethyl] cyclohexanol, hydrochloride 0.27 g (11.3 mmole) of magnesium turnings was stirred in 5 ml of ether of analysis purity. 1.93 g (11.3 mmole) of benzyl bromide dissolved in 10 ml of ether were added dropwise so that the reaction mixture boiled gently. After completion of the addition the reaction mixture was stirred for a further hour at RT. 2.5 g (9.4 mmole) of the 2-[(2-chlorophenyl) dimethyl-aminomethyl]cyclohexanone prepared according to Example 38 were dissolved in 10 ml of ether, added dropwise while cooling in an ice bath to the Grignard reagent, and stirred for 15 hours at RT. The reaction mixture was worked up by adding 20 ml of saturated ammonium chloride solution while cooling in an ice bath, and was extracted three times at RT with 20 ml of ether each time. The combined organic extracts were dried over sodium sulfate, filtered, and concentrated by evaporation on a rotary evaporator (500 to 10 mbar). 3.18 g of crude base (94.4% of theory) were obtained, from which a hydrochloride was precipitated according to Example 1 ($3^{rd}$ stage) with chlorotrimethylsilane/water in 2-butanone. The base was freed from the hydrochloride with 20 ml of water and 5 ml of amnmonia solution (25 vol. %), extracted three times, each time with 20 ml of ether, and the combined organic extracts were dried over sodium sulfate, filtered, and concentrated by evaporation on a rotary evaporator (500 to 10 mbar). 1.93 g of crude base were obtained, which were added to a 3×25 cm column filled with silica gel. Elution with ethyl acetate/n-hexane (1:4) yielded 0.92 g of base, from which 0.43 g of 1-benzyl-2-[(2-chlorophenyl) dimethylamino-methyl]cyclohexanol, hydrochloride (11.5% of theory) having a melting point of 170° C. were obtained according to the procedure described in Example 1 ($3^{rd}$ Stage) with chlorotrimethylsilane/water in 2-butanone.

Example 46

1-(4-tert.-butylbenzyl)-2-[(3,4-dichlorophenyl) dimethylaminomethyl]cyclohexanol, hydrochloride 0.24 g (9.9 mmole) of magnesium turnings was stirred in 5 ml of ether of analysis purity. 1.81 g (9.9 mmole) of 4-tert.-butylbenzyl chloride dissolved in 5 ml of ether were added dropwise so that the reaction mixture boiled gently. After completion of the addition the reaction mixture was stirred for a further hour at RT. 2.48 g (8.3 mmole) of the 2-[(3,4-dichlorophenyl)dimethylaminomethyl] cyclohexanone prepared according to Example 39 were dissolved in 10 ml of ether, added dropwise while cooling in an ice bath to the Grignard reagent, and stirred for 15 hours at RT. The reaction mixture was worked up by adding 15 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 3.69 g of crude base (99.6% of theory) were obtained, from which 1.54 g of 1-(4-tert.-butylbenzyl)-2-[(3,4-dichlorophenyl) dimethylaminomethyl]cyclohexanol, hydrochloride (38.3% of theory) were obtained according to the procedure described in Example 1 ($3^{rd}$ Stage) with chlorotrimethylsilane/water in 2-butanone. The hydrochloride decomposes on heating above 210° C.

Example 47

2-[dimethylamino-(4-fluorophenyl)methyl]-1-(3-trifluoromethylbenzyl)cyclohexanol, hydrochloride 0.29 g (12.1 mmole) of magnesium turnings was stirred in 5 ml of ether of analysis purity. 2.35 g (12.1 mmole) of 3-chlorobenzotrifluoride dissolved in 5 ml of ether were added dropwise so that the reaction mixture boiled gently. After completion of the addition the reaction mixture was stirred for a further hour at RT. 2.51 g (10.1 mmole) of the 2-[dimethylamino-(4-fluorophenyl)methyl]cyclohexanone prepared according to Example 41 were dissolved in 5 ml of ether, added dropwise to the Grignard reagent while cooling in an ice bath, and stirred for 15 hours at RT. The reaction mixture was worked up by adding 15 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 4.15 g of crude base (101% of theory) were obtained, from which 3.10 g of 2-[dimethylamino-(4-fluorophenyl)methyl]-1-(3-trifluoromethylbenzyl)cyclo-hexanol, hydrochloride (69.1% of theory) were obtained according to the procedure described in Example 1 (3rd Stage) with chlorotrimethylsilane/water in 2-butanone. The hydrochloride decomposes on heating above 210° C.

Example 48

2-(dimethylaminophenylmethyl)bicyclohexyl-1-ol, hydrochloride 3.0 g (13.0 mmole) of the 2-(dimethylaminophenylmethyl)cyclohexanone prepared according to Example 1 were dissolved in 10 ml of tetrahydrofuran, added dropwise while cooling in an ice bath to 7.8 ml (15.6 mmole) of cyclohexylmagnesium chloride (2 M solution in tetrahydrofuran), and stirred for 15 hours at RT. The reaction mixture was worked up by adding 20 ml of saturated ammoniun chloride solution while cooling in an ice bath and extracted three times at RT, with 20 ml of ether each time. The combined organic extracts were dried over sodium sulfate, filtered, and concentrated by evaporation on a rotary evaporator (500 to 10 mbar). 4.03 g of crude base (98.5% of theory) were obtained, from which 2.22 g of 2-(dimethylaminophenylmethyl)bicyclohexyl-1-ol, hydrochloride (48.5% of theory) with a melting point of 220° C.–223° C. were obtained according to the procedure described in Example 1 ($3^{rd}$ Stage) with chlorotrimethylsilane/water in 2-butanone.

Example 49

2-(dimethylaminophenylmethyl)-1-(4-methoxybenzyl)cyclohexanol, hydrochloride 0.38 g (15.6 mmole) of magnesium turnings was stirred in 15 ml of tetrahydrofuran of analysis purity. 2.44 g (15.6 mmole) of 4-methoxybenzyl chloride dissolved in 15 ml of tetrahydrofuran were added dropwise so that the reaction mixture boiled gently. After completion of the addition the reaction mixture was stirred for a further 1.5 hours at 65° C. 3.0 g (13.0 mmole) of the 2-(dimethylaminophenylmethyl)cyclohexanone prepared according to Example 1 were dissolved in 15 ml of tetrahydrofuran, added dropwise while cooling in an ice bath to the Grignard reagent, and stirred for 15 hours at RT. The reaction mixture was worked up by adding 20 ml of saturated ammonium chloride solution while cooling in an ice bath, and extracted three times at RT with 20 ml of ether each time. The combined organic extracts were dried over sodium sulfate, filtered, and concentrated by evaporation on a rotary evaporator (500 to 10 mbar). 4.26 g of crude base (93.0% of theory) were obtained, from which 2.87 g of 2-(di-methylaminophenylmethyl)-1-(4-methoxybenzyl)cyclohexanol, hydrochloride (56.8% of theory) were obtained according to the procedure described in Example 1 ($3^{rd}$ Stage) with chlorotrimethylsilane/water in 2-butanone. The hydrochloride decomposes on heating above 130° C.

Example 50

1-(2,4-difluorobenzyl)-2-(dimethylaminophenylmethyl)cyclohexanol, hydrochloride 0.29 g (11.9 mmole) of magnesium turnings was stirred in 5 ml of ether of analysis purity. 2.47 g (11.9 mmole) of 2,4-difluorobenzyl bromide dissolved in 10 ml of ether were added dropwise so that the reaction mixture boiled gently. After completion of the addition the reaction mixture was stirred for a further hour at RT. 2.30 g (9.9 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and extracted three times at RT with 15 ml of ether each time. The combined organic extracts were dried over sodium sulfate, filtered, and concentrated by evaporation on a rotary evaporator (500 to 10 mbar). 1.78 g of crude base (49.9% of theory) were obtained. The aqueous solution was extracted three times with 15 ml of ether and 15 ml of dichloromethane each time. The combined organic extracts were dried over sodium sulfate, filtered, and concentrated by evaporation on a rotary evaporator (500 to 10 mbar). 1.31 g of crude base (36.7% of theory) were obtained. The hydrochloride was precipitated from both bases according to Example 1 ($3^{rd}$ stage) with chlorotrimethylsilane/water in 2-butanone. 0.95 g of 1-(2,4-difluorobenzyl)-2-(dimethylaminophenylmethyl)cyclohexanol, hydrochloride (20.2% of theory) was obtained from the first base, and 1.27 g of 1-(2,4-difluorobenzyl)-2-(dimethylaminophenylmethyl)cyclohexanol, hydrochloride (32.4% of theory) with a melting point of 178° C. was obtained from the second base.

Example 51

1-(4-tert.-butylbenzyl)-2-[(3-chlorophenyl)dimethylaminomethyl]cyclohexanol, hydrochloride 0.22 g (9.0 mmole) of magnesium turnings was stirred in 5 ml of ether of analysis purity. 1.65 g (9.0 mmole) of 4-tert.-butylbenzyl chloride dissolved in 5 ml of ether were added dropwise so that the reaction mixture boiled gently. After completion of the addition the reaction mixture was stirred for a further hour at RT. 2.0 g (7.5 mmole) of the 2-[(chloro-phenyl)dimethylaminomethyl]cyclohexanone obtained according to Example 38 were dissolved in 10 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and extracted three times at RT with 15 ml of ether each time. The combined organic extracts were dried over sodium sulfate, filtered, and concentrated by evaporation on a rotary evaporator (500 to 10 mbar). 2.50 g of crude base (80.1% of theory) were obtained, from which 1.03 g of 1-(4-tert.-butylbenzyl)-2-[(3-chlorophenyl)dimethylaminomethyl]cyclohexanol, hydrochloride (30.5% of theory) having a melting point above 225° C. were obtained according to the procedure described in Example 1 ($3^{rd}$ Stage) with chlorotrimethylsilane/water in 2-butanone.

Example 52

2-[dimethylamino-(3-phenoxyphenyl)methyl]-1-phenethylcyclohexanol, hydrochloride 2.0 g (6.2 mmole) of the 2-[dimethylamino-(3-phenoxyphenyl)methyl]cyclohexanone prepared according to Example 34 were dissolved in 9 ml of tetrahydrofuran, added dropwise while cooling in an ice bath to 7.4 ml (9.0 mmole) of phenethylmagnesium chloride (1 M solution in tetrahydrofuran), and stirred for 15 hours at RT. The reaction mixture was worked up by adding 10 ml of saturated ammonium chloride solution while cooling in an ice bath, and extracted three times at RT with 10 ml of ether each time. The combined organic extracts were dried over sodium sulfate, filtered, and concentrated by evaporation on a rotary evaporator (500 to 10 mbar). 2.55 g of crude base (96.0% of theory) were obtained, from which a hydrochloride was precipitated according to Example 1 ($3^{rd}$ stage) with chlorotrimethylsilane/water in 2-butanone. The base was freed from the hydrochloride with 20 ml of water and 5 ml of ammonia solution (25 vol. %), extracted three times, each time with 10 ml of ether, and the combined organic extracts were dried over sodium sulfate, filtered, and concentrated by evaporation on a rotary evaporator (500 to 10 mbar). 1.51 g of crude base (56.8% of theory) were obtained, from which 1.31 g of 2-[dimethylamino-(3-phenoxyphenyl)methyl]-1-phenethylcyclohexanol, hydrochloride (45.2% of theory) were obtained according to the procedure described in Example 1 (3$^{rd}$ Stage) with chlorotrimethylsilane/water in 2-butanone. The hydrochloride decomposes on heating above 120° C.

Example 53

2-[dimethylamino-(3-phenoxyphenyl)methyl]-1-(3-trifluoromethylbenzyl)cyclohexanol, hydrochloride 0.18 g (7.4 mmole) of magnesium turnings was stirred in 5 ml of ether of analysis purity. 1.44 g (7.4 mmole) of 3-chloromethylbenzotrifluoride dissolved in 5 ml of ether were added dropwise so that the reaction mixture boiled gently. After completion of the addition the reaction mixture was stirred for one hour at RT. 2.0 g (6.2 mmole) of the 2-[dimethylamino-(3-phenoxyphenyl)methyl]cyclohexanone prepared according to Example 34 were dissolved in 15 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and was extracted three times at RT with 10 ml of ether each time. The combined organic extracts were dried over sodium sulfate, filtered, and concentrated by evaporation on a rotary evaporator (500 to 10 mbar). 2.85 g of crude base (95.3% of theory) were obtained, from which a hydrochloride was precipitated according to Example 1 (3$^{rd}$ stage) with chlorotrimethylsilane/water in 2-butanone. The base was freed from the hydrochloride with 20 ml of water and 5 ml of ammonia solution (25 vol. %), extracted three times, each time with 10 ml of ether, and the combined organic extracts were dried over sodium sulfate, filtered, and concentrated by evaporation on a rotary evaporator (500 to 10 mbar). 0.94 g of crude base (31.4% of theory) was obtained, from which 0.35 g of 2-[dimethylamino-(3-phenoxyphenyl)methyl]-1-(3-trifluoromethylbenzyl)cyclohexaniol, hydrochloride (10.8% of theory) was obtained according to the procedure described in Example 1 (3$^{rd}$ Stage) with chlorotrimethylsilane/water in 2-butanone. In order to purify the hydrochloride the latter was stirred with 120 ml of cyclohexane at 50° C., cooled in an ice bath, decanted, and the residue was dried. 0.27 g of hydrochloride (8.4% of theory) was obtained in this way.

Example 54

1-(2,5-difluorobenzyl)-2-(dimethylaminophenylmethyl)cyclohexanol, hydrochloride 0.29 g (11.9 mmole) of magnesium turnings was stirred in 5 ml of ether of analysis purity. 2.47 g (11.9 mmole) of 2,5-difluorobenzyl bromide dissolved in 10 ml of ether were added dropwise so that the reaction mixture boiled gently. After completion of the addition the reaction mixture was stirred for a further hour at RT. 2.30 g (9.9 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction mixture was worked up by adding 15 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 3.49 g of crude base (97.8% of theory) were obtained, from which a hydrochloride was precipitated according to Example 1 (3$^{rd}$ stage) with chlorotrimethylsilane/water in 2-butanone. The base was freed from the hydrochloride with 30 ml of water and 10 ml of ammonia solution (25 vol. %), extracted three times, each time with 20 ml of ether, and the combined organic extracts were dried over sodium sulfate, filtered, and concentrated by evaporation on a rotary evaporator (500 to 10 mbar). 2.75 g of crude base (77.0% of theory) were obtained, from which 2.21 g of 1-(2,5-difluoro-benzyl)-2-(dimethylaminophenylmethyl)cyclohexanol, hydrochloride (56.4% of theory) with a melting point of 219° C.–221° C. were obtained according to the procedure described in Example 1 (3$^{rd}$ Stage) with chlorotrimethylsilane/water in 2-butanone.

Example 55

1-(3,4-difluorobenzyl)-2-(dimethylaminophenylmethyl)cyclohexanol, hydrochloride 0.29 g (11.9 mmole) of magnesium turnings was stirred in 5 ml of ether of analysis purity. 2.47 g (11.9 mmole) of 3,4-difluorobenzyl bromide dissolved in 10 ml of ether were added dropwise so that the reaction mixture boiled gently. After completion of the addition the reaction mixture was stirred for a further hour at RT. 2.30 g (9.9 mmole) of the 2-(dimethyl-aminophenylmethyl)cyclohexanone prepared according to Example 1 were dissolved in 10 ml of ether, added dropwise to the Grignard reagent while cooling in an ice bath, and stirred for 15 hours at RT. The reaction mixture was worked up by adding 15 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 3.58 g of crude base (100% of theory) were obtained, from which a hydrochloride was precipitated according to Example 1 (3$^{rd}$ stage) with chlorotrimethylsilane/water in 2-butanone. The base was freed from the hydrochloride with 30 ml of water and 10 ml of ammonia solution (25 vol. %), extracted three times, each time with 20 ml of ether, and the combined organic extracts were dried over sodium sulfate, filtered, and concentrated by evaporation on a rotary evaporator (500 to 10 mbar). 2.31 g of crude base (64.7% of theory) were obtained, from which 2.0 g of 1-(3,4-difluoro-benzyl)-2-(dimethylaminophenylmethyl)cyclohexanol, hydrochloride (51.0% of theory) with a melting point of 185° C.–188° C. were obtained according to the procedure described in Example 1 (3$^{rd}$ Stage) with chlorotrimethylsilane/water in 2-butanone.

Example 56

1-(2-chloro-6-fluorobenzyl)-2-(dimethylaminophenylmethyl)cyclohexanol, hydrochloride 0.38 g (15.6 mmole) of magnesium turnings was stirred in 10 ml of ether of analysis purity. 2.79 g (15.6 mmole) of 2-chloro-6-fluorobenzyl chloride dissolved in 10 ml of ether were added dropwise so that the reaction mixture boiled gently. After completion of the addition the reaction mixture was stirred for one hour at RT. 3.00 g (13.0 mmole) of the 2-(dimethylaminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 20 ml of saturated ammonium chloride solution while cooling in an ice bath, and was extracted three times at RT with 30 ml of ether each time. The combined organic extracts were dried over sodium sulfate, filtered, and concentrated by evaporation on a rotary evaporator (500 to 10 mbar). 4.92 g of crude base (101% of theory) were obtained, from which 3.28 g of 1-(2-chloro-6-fluorobenzyl)-2-(dimethylaminophenylmethyl)cyclohexanol, hydrochloride (61.2% of theory) were obtained according to the procedure described in Example 1 ($3^{rd}$ Stage) with chlorotrimethylsilane/water in 2-butanone. The hydrochloride decomposes on heating above 225° C.

Example 57

1-(2,3-difluorobenzyl)-2-(dimethylaminophenylmethyl)cyclohexanol, hydrochloride 0.41 g (16.8 mmole) of magnesium turnings was stirred in 10 ml of ether of analysis purity. 3.47 g (16.8 mmole) of 2,3-difluorobenzyl bromide dissolved in 10 ml of ether were added dropwise so that the reaction mixture boiled gently. After completion of the addition the reaction mixture was stirred for a further hour at RT. 3.23 g (14.0 mmole) of the 2-(dimethylaminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 20 ml of saturated ammonium chloride solution while cooling in an ice bath, and was extracted three times at RT with 20 ml of ether each time. The combined organic extracts were dried over sodium sulfate, filtered, and concentrated by evaporation on a rotary evaporator (500 to 10 mbar). 5.13 g of crude base (102% of theory) were obtained, from which 1.67 g of 1-(2,3-difluorobenzyl)-2-(dimethylamino-phenylmethyl)cyclohexanol, hydrochloride (30.0% of theory) were obtained according to the procedure described in Example 1 ($3^{rd}$ Stage) with chlorotrimethylsilane/water in 2-butanone. The hydrochloride decomposes on heating above 140° C.

Example 58

1-benzyl-2-[(4-chlorophenyl)dimethylaminomethyl]cyclohexanol, hydrochloride $1^{st}$ Stage 2-[(4-chlorophenyl)dimethylaminomethyl]cyclohexanone 15.1 g (185 mmole) of freshly dried dimethylamine hydrochloride were added while stirring to 407 ml (407 mmole) of sodium iodide solution (1 M in acetonitrile) cooled to 0° C. in an ice bath, following which 52 ml (370 mmole) of triethylamine and 52 ml (407 mmole) of chlorotrimethylsilane were added dropwise and the whole was stirred for a further hour at RT. 26.0 g (185 mmole) of 4-chlorobenzaldehyde were added while cooling with ice, and the whole was stirred for a further hour at RT. The reaction mixture was cooled again to 0° C. with an ice bath, 12.0 ml (185 mmole) of 1-(pyrrolidino)-1-cyclohexene were added, and the whole was stirred for a further two hours at RT. The reaction mixture was worked up by adding 280 ml of semi-concentrated hydrochloric acid while cooling in an ice bath, stirred for 10 minutes, washed twice with 280 ml of ether each time, and then adjusted to the alkaline range (pH ca. 9) with 700 ml of dilute amnmonia solution (5 vol. %). The reaction mixture was extracted three times with 280 ml of ether each time, and the combined organic extracts were dried over sodium sulfate, filtered, and concentrated by evaporation on a rotary evaporator without heating (500 to 10 mbar). 16.2 g of crude base (33.0% of theory) were obtained, from which 14.8 g of the hydrochloride of 2-[(4-chlorophenyl)dimethylaminomethyl]cyclohexanone (57.2% of theory) were obtained according to the procedure described in Example 1 (2nd Stage) with chlorotrimethylsilane/water in 2-butanone.

$2^{nd}$ Stage 1-benzyl-2-[(4-chlorophenyl)dimethylaminomethyl]cyclohexanol, hydrochloride The base was freed from 2.5 g (8.27 mmole) of the hydrochloride of 2-[(4-chlorophenyl)dimethylaminomethyl]cyclohexanone obtained according to stage 1 with 30 ml of water and 5 ml of amnonia solution (25 vol. %), was extracted three times with 30 ml of ether each time, and the combined organic extracts were dried over sodium sulfate, filtered, and concentrated by evaporation on a rotary evaporator without heating (500 to 10 mbar). 1.80 g (6.75 mmole) of this base were dissolved in 10 ml of tetrahydrofuran, added dropwise while cooling in an ice bath to 4.05 ml (8.13 mmole) of benzylmagnesium chloride (2 M solution in tetrahydro-furan), and stirred for 15 hours at RT. 2.30 g of crude base (94.9% of theory) were obtained, from which 1.24 g of 1-benzyl-2-[(4-chlorophenyl)dimethylaminomethyl]cyclohexanol, hydrochloride (46.7% of theory) were obtained according to the procedure described in Example 1 ($3^{rd}$ Stage) with chlorotrimethylsilane/water in 2-butanone. The hydrochloride decomposes on heating above 130° C.

Example 59

1-dimethylamino-3-ethyl-2-methyl-1,5-diphenylpentan-3-ol, hydrochloride $1^{st}$ Stage 1-(1-ethylpropenyl)pyrrolidine 99 g (1.39 mole) of pyrrolidine dissolved in 460 ml of n-pentane were added clropwise to 40 g (0.464 mole) of 3-pentanone dissolved in 1600 ml of n-pentane, and the solution was cooled to 0° C. in an ice bath. 48.4 g (0.255 mole) of titanium tetrachloride dissolved in 480 ml of n-pentane were added dropwise at 0° C.–10° C. within one hour, the mixture was stirred for two further hours at RT, and the suspension was filtered. The filtrate was concentrated by evaporation on a rotary evaporator (500 to 10 mbar), and 44.3 g of 1-(1-ethylpropenyl)pyrrolidine (68.6% of theory) were obtained in this way.

$2^{nd}$ Stage 1-dimethylamino-2-methyl-1-phenylpentan-3-one 25.9 g (318 mmole) of freshly dried dimethylamine hydrochloride were added while stirring to 700 ml (700 mmole) of sodium iodide solution (1 M in acetonitrile) cooled to 0° C. in an ice bath, followed by the dropwise addition of 89 ml (636 mmole) of triethylamine and 89 ml (700 mmole) of chlorotrimethylsilane, and the whole was stirred for a further hour at RT. 33.8 g (318 mmole) of benzaldehyde were added while cooling with ice, and the mixture was stirred for a further hour at RT. The reaction mixture was cooled again to 0° C. in an ice bath, 44.3 g (318 mmole) of 1-(1-ethylpropenyl) pyrrolidine from stage 1 were added, and the whole was stirred. for a further two hours at RT. The reaction mixture was worked up by adding 480 ml of semi-concentrated hydrochloric acid while cooling with ice, stirred for 10 minutes, washed twice with 480 ml of ether each time, and adjusted to the alkaline range (pH ca. 9) with 1200 ml of dilute ammonia solution (5 vol. %). The reaction mixture was extracted three times with 480 ml of ether each time, and the combined organic extracts were dried over sodium sulfate, filtered, and concentrated by evaporation on a rotary evaporator (500 to 10 mbar) without heating. 51.3 g of crude base (73.6% of theory) were obtained, from which 26.5 g of the hydrochloride of 1-dimethylamino-2-methlyl-1-phenyl-pentan-3-one (32.6% of theory) were obtained according to the procedure described in Example 1 (2nd Stage) with chlorotrimethylsilane/water in 2-butanone.

$3^{rd}$ Stage 1-dimethylamino-3-ethyl-2-methyl-1,5-diphenylpentan-3-ol, hydrochloride The base was freed from 2.5 g (9.77 mmole) of the hydrochloride of 1-dimethylamino-2-methyl-1-phenylpentan-3-one obtained according to stage 2 with 30 ml of water and 5 ml of ammonia solution (25 vol. %), extracted three times with 30 ml of ether each time, and the combined organic extracts were dried over sodium sulfate, filtered, and concentrated by evaporation on a rotary evaporator (500 to 10 mbar). 1.90 g (8.7 mmole) of this base were dissolved in 13 ml of tetrahydrofuran, added dropwise while cooling in an ice bath to 10.4 ml (10.4 mmole) of phenethylmagnesium chloride (1 M solution in tetrahydrofuran), and stirred for 15 hours at RT. The reaction mixture was worked up by adding 15 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 1.96 g of crude base (69.6% of theory) were obtained, from which a hydrochloride was precipitated according to Example 1 ($3^{rd}$ stage) with chlorotrimethylsilane/water in 2-butanone. The base was freed from the hydrochloride with 20 ml of water and 5 ml of ammonia solution (25 vol. %), extracted three times with 20 ml of ether each time, and the combined organic extracts were dried over sodium sulfate, filtered, and concentrated by evaporation on a rotary evaporator (500 to 10 mbar). 0.72 g of crude base was obtained, which was added to a 3.5×25 cm column filled with silica gel. Elution with ethyl acetate/n-hexane (1:4) yielded 0.41 g of base, from which 0.19 g of 1-dimethylamino-3-ethyl-2-methyl-1,5-diphenylpentan-3-ol, hydrochloride (6.0% of theory) having a melting point of 63° C.–66° C. was obtained according to the procedure described in Example 1 ($3^{rd}$ Stage) with chlorotrimethylsilane/water in 2-butanone.

Example 60

1-(2-chlorobenzyl)-2-[(2-chlorophenyl) dimethylaminomethyl]cyclohexanol, hydrochloride 0.22 g (9.0 mmole) of magnesium turnings was stirred in 5 ml of ether of analysis purity. 1.45 g (9.0 mmole) of 2-chlorobenzyl chloride dissolved in 5 ml of ether were added dropwise so that the reaction mixture boiled gently. After completion of the addition the reaction mixture was stirred for a further hour at RT. 2.00 g (7.5 mmole) of the 2-[(2-chlorophenyl)dimethylaminomethyl]cyclohexanone prepared according to Example 38 were dissolved in 10 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 2.57 g of crude base (87.1% of theory) were obtained, from which a hydrochloride was precipitated according to Example 1 ($3^{rd}$ stage) with chlorotrimethylsilane/water in 2-butanoine. The base was freed from the hydrochloride with 20 ml of water and 5 ml of ammonia solution (25 vol. %), extracted three times with 20 ml of ether each time, and the combined organic extracts were dried over sodium sulfate, filtered, and concentrated by evaporation on a rotary evaporator (500 to 10 mbar). 0.74 g of crude base was obtained, which was added to a 3×15 cm column filled with silica gel. Elution with ethyl acetate/n-hexane (1:4) yielded 0.60 g of base, from which 0.42 g of 1-(2-chlorobenzyl)-2-[(2-chlorophenyl) dimethylaminomethyl]cyclohexanol, hydrochloride (12.9% of theory) having a melting point of 146–147° C. was obtained according to the procedure described in Example 1 ($3^{rd}$ Stage) with chlorotrimethylsilane/water in 2-butanone.

Example 61

1-benzyl-2-[(4-bromophenyl)dimethylaminomethyl] cyclohexanol, hydrochloride $1^{st}$ Stage 2-[(4-bromophenyl)dimethylaminomethyl]cyclohexanone 2.64 g (32.4 mmole) of freshly dried dimethylamine hydrochloride were added while stirring to 71 ml (71 mmole) of sodium iodide solution (1 M in acetonitrile) cooled to 0° C. in an ice bath, followed by the dropwise addition of 9.0 ml (65 mmole) of triethylamine and 9.0 ml (71 mmole) of chlorotrimethylsilane, and the whole was stirred for a further hour at RT. 6.0 g (32.4 mmole) of 4-bromobenzaldehyde were added while cooling with ice, and the whole was stirred for a further hour at RT. The reaction mixture was cooled again to 0° C. with an ice bath, 5.2 ml (2.45 mmole) of 1-(pyrrolidino)-1-cyclohexene were added, and the whole was stirred for a further two hours at RT. The reaction mixture was worked up by adding 50 ml of semi-concentrated hydrochloric acid while cooling in an ice bath, stirred for 10 minutes, washed twice with 50 ml of ether each time, and then adjusted to the alkaline range (pH ca. 9) with 120 ml of dilute ammonia solution (5 vol. %). The reaction mixture was extracted three times with 50 ml of ether each time, and the combined organic extracts were dried over sodium sulfate, filtered, and concentrated by evaporation on a rotary evaporator (500 to 10 mbar) without heating. 7.37 g of crude base (73.3% of theory) were obtained, from which 6.48 g of the hydrochloride of 2-[(4-bromophenyl)dimethylaminomethyl]cyclohexanone (57.6% of theory) were obtained according to the procedure described in Example 1 (2nd Stage) with chlorotrimethylsilane/water in 2-butanone.

$2^{nd}$ Stage 1-benzyl-2-[(4-bromophenyl)dimethylaminomethyl] cyclohexanol, hydrochloride The base was freed from the 2.0 g (5.77 mmole) of the hydrochloride of 2-[(4-bromophenyl)dimethylaminomethyl] cyclohexanone obtained according to stage 1 with 20 ml of water and 5 ml of ammonia solution (25 vol. %), extracted three times with 20 ml of ether each time, and the combined organic extracts were dried over sodium sulfate, filtered, and concentrated by evaporation on a rotary evaporator without heating (500 to 10 mbar). 1.70 g (5.5 mmole) of this base were dissolved in 8.5 ml of tetrahydrofuran, added dropwise while cooling in an ice bath to 3.3 ml (6.6 mmole) of benzylmagnesium chloride (2 M solution in tetrahydrofuran), and stirred for 15 hours at RT. The reaction mixture was worked up by adding 10 ml of saturated ammonium chloride solution while cooling in an ice bath, and was extracted three times at RT with 10 ml of ether each time. The combined organic extracts were dried over sodium sulfate, filtered, and concentrated by evaporation on a rotary evaporator (500 to 10 mbar). 1.91 g of crude base (86.64% of theory) were obtained, from which 0.86 g of 1-benzyl-2-[(4-bromophenyl) dimethylaminomethyl]cyclohexanol, hydrochloride (35.9% of theory) were obtained according to the procedure described in Example 1 ($3^{rd}$ Stage) with chloro-trimethylsilane/water in 2-butanone. The hydrochloride decomposes on heating above 151° C.

Example 62

2-[(4-chlorophenyl)dimethylaminomethyl]-1-(4-trifluoromethylphenyl)cyclohexanol, hydrochloride 0.22 g (9.0 mmole) of magnesium turnings was stirred in 5 ml of ether of analysis purity. 2.03 g (9.0 mmole) of 4-bromo-benzotrifluoride dissolved in 5 ml of ether were added dropwise so that the reaction mixture boiled gently. After completion of the addition the reaction mixture was stirred for a further hour at RT. 2.00 g (7.5 mmole) of the 2-[(4-chloro-phenyl)dimethylaminomethyl]cyclohexanone prepared according to Example 58 were dissolved in 10 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 2.65 g of crude base (85.4% of theory) were obtained, from which a hydrochloride was precipitated according to Example 1 ($3^{rd}$ stage) with chlorotrimethylsilane/water in 2-butanone. The base was freed from the hydrochloride with 20 ml of water and 5 ml of ammonia solution (25 vol. %), extracted three times with 20 ml of ether each time, and the combined organic extracts were dried over sodium sulfate, filtered, and concentrated by evaporation on a rotary evaporator (500 to 10 mbar). 0.50 g of crude base (16.2% of theory) was obtained, from which 0.20 g of 2-[(4-chlorophenyl) dimethylaminomethyl]-(4-trifluoromethylphenyl) cyclohexanol, hydrochloride (6.0% of theory) with a melting point above 240° C. was obtained according to the procedure described in Example 1 ($3^{rd}$ Stage) with chlorotrimethylsilane/water in 2-butanone.

Example 63

2-[(4-chlorophenyl)dimethylaminomethyl]-1-(3-trifluoromethylbenzyl)cyclohexanol, hydrochloride 0.22 g (9.0 mmole) of magnesium turnings was stirred in 5 ml of ether of analysis purity. 1.76 g (9.0 mmole) of 3-chloromethylbenzotrifluoride dissolved in 5 ml of ether were added dropwise so that the reaction mixture boiled gently. After completion of the addition the reaction mixture was stirred for a further hour at RT. 2.00 g (7.5 mmole) of the 2-[(4-chlorophenyl)dimethylaminomethyl] cyclohexanone prepared according to Example 58 were dissolved in 10 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 1.46 g of crude base (45.6% of theory) were obtained, from which a hydrochloride was precipitated according to Example 1 ($3^{rd}$ stage) with chlorotrimethylsilane/water in 2-butanone. The base was freed from the hydrochloride with 15 ml of water and 5 ml of ammonia solution (25 vol. %), extracted three times with 15 ml of ether each time, and the combined organic extracts were dried over sodium sulfate, filtered, and concentrated by evaporation on a rotary evaporator (500 to 10 mbar). 0.33 g of crude base (10.3% of theory) was obtained, from which 0.12 g of 2-[(4-chlorophenyl) dimethylaminomethyl]-1-(3-trifluoromethylbenzyl) cyclohexanol, hydrochloride (3.6% of theory) was obtained according to the procedure described in Example 1 ($3^{rd}$ Stage) with chlorotrimethylsilane/water in 2-butanone. The hydrochloride decomposes on heating above 115° C.

Example 64

1-(4-tert.-butylbenzyl)-2-[dimethylamino-(3-phenoxyphenyl)methyl]cyclohexanol, hydrochloride 0.15 g (6.3 mmole) of magnesium turnings was stirred in 5 ml of ether of analysis purity. 1.15 g (6.3 mmole) of 4-tert.-butylbenzyl chloride dissolved in 5 ml of ether were added dropwise so that the reaction mixture boiled gently. After completion of the addition the reaction mixture was stirred for a further hour at RT. 1.70 g (5.3 mmole) of the 2-[dimethyl-amino-(3-phenoxyphenyl)methyl] cyclohexanone prepared according to Example 34 were dissolved in 5 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and was extracted three times at RT with 10 ml of ether each time. The combined organic extracts were dried over sodium sulfate, filtered, and concentrated by evaporation on a rotary evaporator (500 to 10 mbar). 2.01 g of crude base (68.6% of theory) were obtained, from which a hydrochloride was precipitated according to Example 1 ($3^{rd}$ stage) with chlorotrimethylsilane/water in 2-butanone. The base was freed from the hydrochloride with 20 ml of water and 5 ml of ammonia solution (25 vol. %), extracted three times with 15 ml of ether each time, and the combined organic extracts were dried over sodium sulfate, filtered, and concentrated by evaporation on a rotary evaporator (500 to 10 mbar). 0.70 g of crude base was obtained, which was added to a 3×15 cm column filled with silica gel. Elution with ethyl acetate/n-hexane (1:4) yielded 0.40 g of base, from which 0.22 g of 1-(4-tert.-butylbenzyl)-2-[dimethylamino-(3-phenoxyphenyl)methyl]cyclohexanol, hydrochloride (8.2% of theory) having a melting point of 192–195° C. was obtained according to the procedure described in Example 1 ($3^{rd}$ Stage) with chlorotrimethylsilane/water in 2-butanone. The hydrochloride decomposes on heating above 92° C.

Example 65

4-{dimethylamino-[2-hydroxy-2-(4-trifluoromethylphenyl)cyclohexyl] methyl}benzonitrile, hydrochloride $1^{st}$ Stage
4-[dimethylamino-(2-oxocyclohexyl]methyl}benzonitrile 2.8 g (34.3 mmole) of freshly dried dimethylamine hydrochloride were added while stirring to 75 ml (75 mmole) of sodium iodide solution (1 M in acetonitrile) cooled to 0° C. in an ice bath, followed by the dropwise addition of 9.6 ml (68.6 mmole) of triethylamine and 9.5 ml (75.5 mmole) of chlorotrimethylsilane, and the whole was stirred for one hour at RT. 4.50 g (34.3 mmole) of 4-cyanobenzaldehyde were added while cooling with ice, and the whole was stirred for a further hour at RT. The reaction mixture was cooled again to 0° C. in an ice bath, 5.5 ml (34.3 mmole) of 1-(pyrrolidino)-1-cyclohexene were added, and the reaction mixture was stirred for a further two hours at RT. The reaction mixture was worked up by adding 50 ml of semi-concentrated hydrochloric acid while cooling with ice, stirred for 10 minutes, washed twice with 50 ml of ether each time, and adjusted to the alkaline range (pH ca. 9) with 130 ml of dilute ammonia solution (5 vol. %). The reaction mixture was extracted three times with 50 ml of ether each time, and the combined organic extracts were dried over sodium sulfate, filtered, and concentrated by evaporation on a rotary evaporator (500 to 10 mbar) without heating. 8.2 g of crude base (93% of theory) were obtained, from which 6.75 g of the hydrochloride of 4-[dimethylamino-(2-oxocyclohexyl]methyl}benzonitrile (67.2% of theory) were obtained according to the procedure described in Example 1 (2nd Stage) with chlorotrimethylsilane/water in 2-butanone.

$2^{nd}$ Stage

4-{dimethylamino-[2-hydroxy-2-(4-trifluoromethylphenyl) cyclohexyl]methyl}benzonitrile, hydrochloride 0.34 g (14.0 mmole) of magnesium turnings was stirred in 10 ml of ether of analysis purity. 3.16 g (14.0 mmole) of 4-bromobenzotrifluoride dissolved in 10 ml of ether were added dropwise so that the reaction mixture boiled gently. After completion of the addition the reaction mixture was stirred for a further hour at RT. The base was freed from 3.5 g (12.0 mmole) of the hydrochloride of 4-[dimethylamino-(2-oxocyclohexyl)methyl]benzonitrile obtained according to stage 1 with 30 ml of water and 5 ml of ammonia solution (25 vol. %), extracted three times with 30 ml of ether each time, and the combined organic extracts were dried over sodium sulfate, filtered, and concentrated by evaporation on a rotary evaporator without heating (500 to 10 mbar). 3.0 g (11.7 mmole) of this base were dissolved in 10 ml of ether, added dropwise to the Grignard reagent while cooling in an ice bath, and stirred for 15 hours at RT. The reaction mixture was worked up by adding 20 ml of saturated ammonium chloride solution while cooling in an ice bath, and was extracted three times at RT with 20 ml of ether each time. The combined organic extracts were dried over sodium sulfate, filtered, and concentrated by evaporation on a rotary evaporator (500 to 10 mbar). 3.52 g of crude base (74.7% of theory) were obtained, from which 0.17 g of 4-{dimethylamino-[2-hydroxy-2-(4-trifluoromethylphenyl) cyclohexyl]methyl}-benzonitrile, hydrochloride (3.3% of theory) having a melting point above 250° C. was obtained according to the procedure described in Example 1 ($3^{rd}$ Stage) with chlorotrimethylsilane/water in 2-butanone.

Example 66

2-(dimethylamino-o-tolylmethyl)-1-phenylcyclohexanol, hydrochloride $1^{st}$ Stage 2-(dimethylamino-o-tolylmethyl)cyclohexanone 6.79 g (83.2 mmole) of freshly dried dimethylamine hydrochloride were added while stirring to 183 ml (183 mmole) of sodium iodide solution (1 M in acetonitrile) cooled to 0° C. in an ice bath, following which 23 ml (166 mmole) of triethylamine and 23 ml (183 mmole) of chlorotrimetlhylsilane were added dropwise and the whole was stirred for one hour at RT. 10.0 g (83.2 mmole) of 2-tolualdehyde were added while cooling with ice, and the reaction mixture was stirred for a further hour at RT. The reaction mixture was cooled again to 0° C. in an ice bath, 13.4 ml (83.2 mmole) of 1-(pyrrolidino)-1-cyclohexene were added, and the whole was stirred for a further two hours at RT. The reaction mixture was worked up by adding 125 ml of semi-concentrated hydrochloric acid while cooling with ice, stirred for 10 minutes, washed twice with 125 ml of ether each time, and adjusted to the alkaline range (pH ca. 9) with 310 ml of dilute ammonia solution (5 vol. %) The reaction mixture was extracted three times with 125 ml of ether each time, and the combined organic extracts were dried over sodium sulfate, filtered, and concentrated by evaporation on a rotary evaporator without heating (500 to 10 mbar). 11.8 g of crude base (57.8% of theory) were obtained, from which 10.4 g of the hydrochloride of 2-(dimethylamino-o-tolyl-methyl)cyclohexanone (44.4% of theory) were obtained according to the procedure described in Example 1 (2nd Stage) with chlorotrimethylsilane/water in 2-butanone.

$2^{nd}$ Stage 2-(dimethylamino-o-tolylmethyl)-1-phenylcyclohexanol, hydrochloride The base was freed from 3.0g (10.6 mmole) of the hydrochloride of 2-(dimethylamino-o-tolylmethyl) cyclohexanone obtained according to stage 1 with 30 ml of water and 5 ml of ammonia solution (25 vol. %), extracted three times with 30 ml of ether each time, and the combined organic extracts were dried over sodium sulfate, filtered, and concentrated by evaporation on a rotary evaporator without heating (500 to 10 mbar). 2.50 g (10.2 mmole) of this base were dissolved in 15 ml of tetrahydrofuran, added dropwise while cooling in an ice bath to 6.1 ml (12.2 mmole) of phenylmagnesium chloride (2 M solution in tetrahydrofuran), and stirred for 15 hours at RT. The reaction mixture was worked up by adding 15 ml of saturated ammonium chloride solution while cooling in an ice bath, and was extracted three times at RT with 20 ml of ether each time. The combined organic extracts were dried over sodium sulfate, filtered, and concentrated by evaporation on a rotary evaporator (500 to 10 mbar). 3.12 g of crude base (94.5% of theory) were obtained, from which 1.97 g of 2-(dimethylamino-o-tolylmethyl)-1-phenylcyclohexanol, hydrochloride (53.7% of theory) were obtained according to the procedure described in Example 1 ($3^{rd}$ Stage) with chlorotrimethylsilane/water in 2-butanone. The hydrochloride decomposes on heating above 137° C.

Example 67

1-benzyl-2-(dimethylamino-o-tolylmethyl) cyclohexanol, hydrochloride 2.0 g (7.5 mmole) of the 2-(dimethylamino-o-tolylmethyl) cyclohexanone prepared according to Example 66 were dissolved in 15 ml of tetrahydrofuran, added dropwise while cooling in an ice bath to 6.1 ml (12.2 mmole) of benzylmagnesium chloride (2 M solution in tetrahydrofuran), and stirred for 15 hours at RT. The reaction mixture was worked up by adding 158 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 3.39 g of crude base (98.5% of theory) were obtained, from which 0.83 g of 1-benzyl-2-(dimethylamino-o-tolylmethyl)cyclo-hexanol, hydrochloride (21.8% of theory) having a melting point of 180–183° C. was obtained according to the procedure described in Example 1 ($3^{rd}$ Stage) with chlorotrimethylsilane/water in 2-butanone.

Example 68

2-(dimethylaminophenylmethyl)-1-(3-phenylpropyl) cyclohexanol, hydrochloride 0.32 g (13.0 mmole) of magnesium turnings was stirred in 10 ml of ether of analysis purity. 2.58 g (13.0 mmole) of 1-bromo-3-phenylpropane dissolved in 10 ml of ether were added dropwise so that the reaction mixture boiled gently. After completion of the addition the reaction mixture was stirred for a further hour at,RT. 2.50 g (10.8 mmole) of the 2-(dimethylaminophenylmethyl)cyclohexanone prepared according to Example 1 were dissolved in 10 ml of ether, added dropwise to the Grignard reagent while cooling in an ice bath, and stirred for 15 hours at RT. The reaction mixture was worked up by adding 15 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 3.73 g of crude base (98.2% of theory) were obtained, from which 2.92 g of 2-(dimethylaminophenylmethyl)-1-(3-phenylpropyl) cyclohexanol hydrochloride (67.7% of theory) were obtained according to the procedure described in Example 1 ($3^{rd}$ Stage) with chlorotrimethylsilane/water in 2-butanone. The hydrochloride decomposes on heating above 90° C.

Example 69

2-[(2-chlorophenyl)dimethylaminomethyl]-1-[2-(4-fluorophenyl)ethyl]cyclohexanol, hydrochloride 0.22 g (9.0 mmole) of magnesium turnings was stirred in 5 ml of ether of analysis purity. 1.83 g (9.0 mmole) of 1-(2-bromomethyl)-4-fluorobenzene dissolved in 5 ml of ether were added dropwise so that the reaction mixture boiled gently. After completion of the addition the reaction mixture was stirred for a further hour at RT. 2.00 g (7.5 mmole) of the 2-[(2-chlorophenyl)dimethylaminomethyl] cyclohexanone prepared according to Example 38 were dissolved in 10 ml of ether, added dropwise to the Grignard reagent while cooling in an ice bath, and stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 2.85 g of crude base (97.2% of theory) were obtained, from which 1.74 g of 2-[(2-chlorophenyl)dimethylaminomethyl]-1-[2-(4-fluorophenyl)ethyl]cyclohexanol, hydrochloride (54.1% of theory) were obtained according to the procedure described in Example 1 ($3^{rd}$ Stage) with chlorotrimethylsilane/water in 2-butanone. The hydrochloride decomposes on heating above 170° C.

Example 70

2-[dimethylaminothiophen-2-ylmethyl]-1-(3-trifluoromethyl benzyl)cyclohexanol, hydrochloride $1^{st}$ Stage 2-[dimethylaminothiophen-2-ylmethyl]cyclohexanone 4.36 g (53.5 mmole) of freshly dried dimethylamine hydrochloride were added while stirring to 118 ml (118 mmole) of sodium iodide solution (1 M in acetonitrile) cooled to 0° C. in an ice bath, following which 15 ml (107 mmole) of triethylamine and 15 ml (118 mmole) of chlorotrimethylsilane were added dropwise and the whole was stirred for a further hour at RT. 6.0 g (53.5 mmole) of thiophene-2-carboxaldehyde were added while cooling with ice, and the reaction mixture was stirred for a further hour at RT. The reaction mixture was cooled again to 0° C. with an ice bath, 8.6 ml (53.5 mmole) of 1-(pyrrolidino)-1-cyclohexene were added, and the whole was stirred for a further two hours at RT. The reaction mixture was worked up by adding 80 ml of semi-concentrated hydrochloric acid while cooling with ice, stirred for 10 minutes, washed twice with 80 ml of ether each time, and adjusted to the alkaline range (pH ca. 9) with 200 ml of dilute ammonia solution. The reaction mixture was extracted three times with 80 ml of ether each time, and the combined organic extracts were dried over sodium sulfate, filtered, and concentrated by evaporation on a rotary evaporator (500 to 10 mbar) without heating. 8.09 g of crude base of 2-(dimethylaminothiophen-2-ylmethyl)cyclohexanone (63.7% of theory) were obtained.

$2^{nd}$ Stage 2-(dimethylaminothiophen)-2-ylmethyl]-1-(3-trifluoromethylbenzyl)cyclohexanol, hydrochloride 0.31 g (12.6 mmole) of magnesium turnings was stirred in 10 ml of ether of analysis purity. 2.46 g (12.6 mmole) of 3-chloromethylbenzotrifluoride dissolved in 10 ml of ether were added dropwise so that the reaction mixture boiled gently. After completion of the addition the reaction mixture was stirred for a further hour at RT. 2.50 g (10.5 mmole) of the 2-(dimethylaminothiophen-2-ylmethyl)cyclohexanone prepared according to stage 1 were dissolved in 10 ml of ether, added dropwise to the Grignard reagent while cooling in an ice bath, and stirred for 15 hours at RT. The reaction mixture was worked up by adding 15 ml of saturated ammonium chloride solution while cooling in an ice bath, and was extracted three times at RT with 20 ml of ether each time. The combined organic extracts were dried over sodium sulfate, filtered, and concentrated by evaporation on a rotary evaporator (500 to 10 mbar). 3.33 g of crude base (79.6% of theory) were obtained, from which a hydrochloride was precipitated according to Example 1 ($3^{rd}$ stage) with chlorotrimethylsilane/water in 2-butanone. The base was freed from the hydrochloride with 20 ml of water and 5 ml of ammonia solution (25 vol. %), extracted three times with 20 ml of ether each time, and the combined organic extracts were dried over sodium sulfate, filtered, and concentrated by evaporation on a rotary evaporator (500 to 10 mbar). 0.63 g of crude base (15.0% of theory) was obtained, from which 0.39 g of 2-[dimethylaminothiophen-2-ylmethyl]-1(3-trifluoromethylbenzyl)cyclohexanol, hydrochloride (8.5% of theory) was obtained according to the procedure described in Example 1 ($3^{rd}$ Stage) with chlorotrimethylsilane/water in 2-butanone. The hydrochloride decomposes on heating above 98° C.

Example 71

Methyl-4-[2-(dimethylaminophenylmethyl)-1-hydroxycyclohexyl]benzoate, hydrochloride 5.6 ml (10.4 mmole) of isopropylmagnesium chloride (2 M solution in ether) were added to 2.72 g (10.4 mmole) of methyl-4-iodobenzoate dissolved in 20 ml of ether and cooled to −40° C. with a dry ice/isopropanol bath, and the whole was stirred for a further hour. 2.0 g (8.65 mmole) of the 2-(dimethyl-aminophenylmethyl)cyclohexanone prepared according to Example 1 were dissolved in 10 ml of ether, added dropwise to the Grignard reagent at −40° C. and stirred for 15 hours at RT. The reaction mixture was worked up by adding 20 ml of saturated ammonium chloride solution while cooling in an ice bath, and extracted three times at RT with 20 ml of ether each time. The confined organic extracts were dried over sodium sulfate, filtered, and concentrated by evaporation on a rotary evaporator (500 to 10 mbar). 3.19 g of crude base (100% of theory) were obtained, from which 3.49 g of methyl-4-[2-(dimethylaminophenylmethyl)-1-hydroxycyclohexyl] benzoate, hydrochloride (57.3% of theory) were obtained according to the procedure described in Example 1 ($3^{rd}$ Stage) with chlorotrimethylsilane/water in 2-butanone. The hydrochloride decomposes on heating above 140° C.

Example 72

1-benzyl-2-(dimethylaminophenylmethyl)-4-phenylcyclohexanol, hydrochloride $1^{st}$ Stage 1-(4-phenylcyclohex-1-enyl)pyrrolidine 36.8 g (0.517 mole) of pyrrolidine dissolved in 170 ml of n-hexane were added dropwise to 30.0 g (0.172 mole) of 4-phenylcyclohexanone dissolved in 860 ml of n-hexane, and the solution was cooled to 0° C. in an ice bath. 18.0 g (0.095 mole) of titanium tetrachloride dissolved in 140 ml of n-hexane were added dropwise within one hour at 0° C.–10° C., stirred for a further two hours at RT, following which the suspension was filtered. The filtrate was concentrated by evaporation on a rotary evaporator (500 to 10 mbar), and the remaining oil was purified by distillation at a pressure of less than 1 mbar; the main fraction boiled at 135° C. 22.2 of crude product were obtained, which on account of incomplete conversion underwent, in the cold, the addition of 27.2 g (0.379 mole) of pyyrolidine dissolved in 125 ml of n-hexane and 13.1 g (0.069 mole) of titanium tetrachloride dissolved in 140 ml of n-hexane, and the mixture was then heated under reflux for two hours. 20.2 g of 1-(4-phenylcyclohex-1-enyl)pyrrolidine (51.7% of theory) were obtained in this way.

$2^{nd}$ Stage 2-(dimethylaminophenylmethyl)-4-phenylcyclohexanone 2.15 g (26.4 mmole) of freshly dried dimethylamine hydrochloride were added while stirring to 58 ml (58 mmole) of sodium iodide solution (1 M in acetonitrile) cooled to 0° C. in an ice bath, following which 7.4 ml (52.8 mmole) of triethylamine and 7.3 ml (58.0 mmole) of chlorotrimethylsilane were added dropwise and the whole was stirred for a further hour at RT. 2.80 g (26.4 mmole) of benzaldehyde were added while cooling with ice, and the reaction mixture was stirred for a further hour at RT. The reaction mixture was cooled again to 0° C. with an ice bath, 6.00 g (26.4 mmole) of 1-(4-phenyl-cyclohex-1-enyl) pyrrolidine from stage 1 were added, and the reaction mixture was stirred for a further two hours at RT. The reaction mixture was worked up by adding 40 ml of semi-concentrated hydrochloric acid while cooling with ice, stirred for 10 minutes, washed twice with 40 ml of ether each time, and adjusted to the alkaline range (pH ca. 9) with 100 ml of dilute ammonia solution (5 vol. %). The reaction mixture was extracted three times with 40 ml of ether each time, and the combined organic extracts were dried over sodium sulfate, filtered, and concentrated by evaporation on a rotary evaporator (500 to 10 mbar) without heating. 6.77 g of crude base (83.5% of theory) were obtained, from which 5.95 g of the hydrochloride of 2-(dimethylaminophenylmethyl)-4-phenylcyclohexanone (65.5% of theory) were obtained according to the procedure described in Example 1 ($2^{nd}$ Stage) with chlorotrimethylsilane/water in 2-butanone.

$3^{rd}$ Stage 1-benzyl-2-(dimethlylaminophenylmethyl)-4-phenylcyclohexanol, hydrochloride The base was freed from 2.5g (7.27 mmole) of the hydrochloride of 2-(dimetlhylaminophenylmethyl)-4-phenylcyclo-hexanone obtained according to stage 2 with 30 ml of water and 5 ml of ammonia solution (25 vol. %), extracted three times with 30 ml of ether each time, and the combined organic extracts were dried over sodium sulfate, filtered, and concentrated by evaporation on a rotary evaporator without heating (500 to 10 mbar). 2.00 g (6.51 mmole) of this base were dissolved in 10 ml of tetrahydrofuran, added dropwise while cooling in an ice bath to 3.9 ml (7.8 mmole) of benzylmagnesium chloride (2 M solution in tetrahydrofuran), and stirred for 15 hours at RT. The reaction mixture was worked tip by adding 10 ml of saturated amnonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 2.12 g of crude base (84.6% of theory) were obtained, from which 1.67 g of 1-benzyl-2-(dimethylaminophenylmethyl)-4-phenylcyclohexanol, hydrochloride (60.7% of theory) with a melting point above 240° C. was obtained according to the procedure described in Example 1 ($3^{rd}$ Stage) with chlorotrimethylsilane/water in 2-butanone.

Example 73

1-(4-bromophenyl)-2-dimethylaminophenylmethyl) cyclohexanol, hydrochloride 2.78 g (9.8 mmole) of 1-bromo-4-iodobenzene were dissolved in 10 ml of ether and cooled in an ice bath (methanol/ice) to −10° C. and 5.45 ml (10.1 mmole) of isopropylmagnesium chloride (2 M solution of tetrahydrofuran) were added dropwise. After stirring for one hour at 0° C., 2.5 g (10.8 mmole) of the 2-25 (dimethylaminophenylmethyl) cyclohexanone prepared according to Example 1 were dissolved in 30 ml of ether and added dropwise, and the whole stirred for 15 hours at RT. The reaction mixture was worked up by adding 40 ml of saturated ammonium chloride solution while cooling in an ice bath, and was extracted three times at RT with 40 ml of ether each time. The combined organic extracts were dried over sodium sulfate, filtered, and concentrated by evaporation on a rotary evaporator (500 to 10 mbar). 4.13 g of crude base (98.4% of theory) were obtained, from which a hydrochloride was precipitated according to Example 1 ($3^{rd}$ stage) with chlorotrimethylsilane/water in 2-butanone. The base was freed from the hydrochloride with 25 ml of water and 5 ml of ammonia solution (25 vol. %), extracted three times, with 25 ml of ether each time, and the combined organic extracts were dried over sodium sulfate, filtered, and concentrated by evaporation on a rotary evaporator (500 to 10 mbar). 2.07 g of crude base (54.4% of theory) was obtained, from which 2.01 g of 1-(4-bromophenyl)-2-dimethylaminophenylmethyl)cyclohexanol, hydrochloride (43.8% of theory) were obtained according to the procedure described in Example 1 ($3^{rd}$ Stage) with chlorotrimethylsilane/water in 2-butanione. The hydrochloride decomposes on heating above 165° C.

Example 74

2-(dimethylaminophenylmethyl)-1-naphthalene-1-ylcyclohexanol, hydrochloride 0.824 g (3.24 mmole) of 1-iodonaphthalene were dissolved in 2 ml of ether, cooled to −10° C., and 1.62 ml (3.24 mmole) of isopropylmagnesium chloride (2 M solution in tetrahydro-furan) were added dropwise. After stirring for one hour at 0° C., 0.50 g (2.16 mmole) of the 2-(dimethylaminophenylmethyl)cyclohexanone prepared according to Example 1 and dissolved in 2 ml of ether were added dropwise, and the whole was stirred for 15 hours at RT. The reaction mixture was worked up by adding 2 ml of saturated ammonium chloride solution while cooling in an ice bath, and was extracted three times at RT with 5 ml of ether each time. The combined organic extracts were dried over sodium sulfate, filtered, and concentrated by evaporation on a rotary evaporator (500 to 10 mbar). 1.00 g of crude base (129% of theory) was obtained, from which 0.23 g of 2-(dimethylaminophenylmethyl)-1-naphthalene-1-ylcyclohexanol, hydrochloride (17.9% of theory) having a melting point above 250° C. was obtained according to the procedure described in Example 1 ($3^{rd}$ Stage) with chlorotrimethylsilane/water in 2-butanone.

Example 75

2-(dimethylaminophenylmethyl)-1-(2-methylsulfanylphenyl)cyclohexanol, hydrochloride 0.811 g (3.24 mmole) of 2-methylmercaptoiodobenzene were dissolved in 2 ml of ether, cooled to –10° C., and 1.62 ml (3.24 mmole) of isopropylmagnesium chloride (2 M solution in tetrahydrofuran) were added dropwise. After stirring for one hour at ° C., 0.50 g (2.16 mmole) of the 2-(dimethylaminophenylmethyl)cyclohexanone prepared according to Example 1 and dissolved in 2 ml of ether was added dropwise, and the whole was stirred for 15 hours at RT. The reaction mixture was worked up by adding 2 ml of saturated ammonium chloride solution while cooling in an ice bath and was extracted three times at RT with 5 ml of ether each time. The combined organic extracts were dried over sodium sulfate, filtered, and concentrated by evaporation on a rotary evaporator (500 to 10 mbar). 0.84 g of crude base (109% of theory) was obtained, from which 0.483 g of 2-(dimethylaminophenyl-methyl)-1-(2-methylsulfanylphenyl)cyclohexanol, hydrochloride (38.0% of theory) was obtained according to the procedure described in Example 1 ($3^{rd}$ Stage) with chlorotrimethylsilane/water in 2-butanone. The hydrochloride decomposes on heating above 230° C.

Example 76

1-benzyl-2-(dimethylaminonaphthalene-2-ylmethyl) cyclohexanol, hydrochloride
$1^{st}$ Stage
2-(dimethylaminonaphthalene-2-ylmethyl)cyclohexanone 19.3 g (237 mmole) of freshly dried dimethylamine hydrochloride were added while stirring to 520 ml (520 mmole) of sodium iodide solution (1 M in acetonitrile) cooled to 0° C. with an ice bath, following which 66 ml (474 mmole) of triethylamine and 66 ml (521 mmole) of chlorotrimethylsilanie were added dropwise and the whole was stirred for a further hour at RT. 37.0 g (237 mmole) of 2-naphthaldehyde were added while cooling with ice, and the whole was stirred for a further hour at RT. The reaction mixture was cooled again to 0° C. with an ice bath, 38 ml (237 mmole) of 1-(pyrrolidino)-1-cyclohexene were added, and the whole was stirred for two hours at RT. The reaction mixture was worked up by adding 350 ml of semi-concentrated hydrochloric acid while cooling with ice, stirred for 10 minutes, washed twice with 350 ml of ether each time, and adjusted to the alkaline range (pH ca. 9) with 890 ml of dilute ammonia solution. The reaction mixture was extracted three times with 350 ml of ether each time, and the combined organic extracts were dried over sodium sulfate, filtered, and concentrated by evaporation on a rotary evaporator (500 to 10 mbar) without heating. 54.7 g of crude base (82.1% of theory) were obtained, from which 50.8 g of the hydrochloride of 2-(dimethylaminonaphthalene-2-ylmethyl)cyclohexanone (67.5% of theory) were obtained according to the procedure described in Example 1 ($2^{nd}$ Stage) with chlorotrimethylsilane/water in 2-butanone.
$2^{nd}$ Stage
1-benzyl-2-(dimethylaminonaphthalene-2-ylmethyl) cyclohexanol, hydrochloride The base was freed from 3.0 g (9.44 mmole) of the hydrochloride of 2-(dimethylaminonaphthalene-2-ylmethyl) cyclohexanone obtained according to stage 1 with 30 ml of water and 5 ml of ammonia solution (25 vol. %), extracted three times with 30 ml of ether each time, and the combined organic extracts were dried over sodium sulfate, filtered, and concentrated by evaporation one a rotary evaporator without heating (500 to 10 mbar). 2.5 g (8.9 mmole) of this base were dissolved in 15 ml of tetrahydrofuran, added dropwise while cooling in an ice bath to 5.3 ml (10.7 mmole) of benzylmagnesium chloride (2 M solution in tetrahydro-furan), and the whole was stirred for 15 hours at RT. The reaction mixture was worked up by adding 20 ml of saturated ammonium chloride solution while cooling in an ice bath, and was extracted three times at RT with 20 ml. of other each time. The combined organic extracts were dried over sodium sulfate, filtered, and concentrated by evaporation on a rotary evaporator (500 to 10 mbar). 3.17 g of crude base (99.2% of theory) were obtained, from which 2.4 g of 1-benzyl-2-(dimethylaminonaphthalene-2-yl-methyl) cyclohexanol, hydrochloride (68.1% of theory) were obtained according to the procedure described in Example 1 ($3^{rd}$ Stage) with chlorotrimethylsilane/water in 2-butanone. The hydrochloride decomposes on heating above 180° C.

Example 77

1-benzyl-2-(dimethylaminopentafluorophenylmethyl) cyclohexanol, hydrochloride
$1^{st}$ Stage
2-(dimethylaminopentafluorophenylmethyl)cyclohexanone 10.4 g (128 mmole) of freshly dried dimethylamine hydrochloride were added while stirring to 280 ml. (280 mmole) of sodium iodide solution (1 M in acetonitrile) cooled to 0° C. with an ice bath, following which 35.5 ml (255 mmole) of triethylamine and 35.5 ml (280 mmole) of chlorotrimethylsilane were added dropwise and the whole was stirred for a further hour at RT. 25.0 g (128 mmole) of pentafluorobenzaldehyde were added while cooling with ice, and the whole was stirred for a further hour at RT. The reaction mixture was cooled again to 0° C. with an ice bath, 20.5 ml (128 mmole) of 1-(pyrrolidino)-1-cyclohexene were added, and the whole was stirred for a further two hours at RT. The reaction mixture was worked up by adding 190 ml of senti-concentrated hydrochloric acid while cooling with ice, stirred for 10 minutes, washed twice with 190 ml of ether each time, and adjusted to the alkaline range (pH ca. 9) with 480 ml of dilute ammonia solution (5 vol. %). The reaction mixture was extracted three times with 190 ml of ether each time, and the combined organic extracts were dried over sodium sulfate, filtered, and concentrated by evaporation on a rotary evaporator (500 to 10 mbar) without heating. 30.2 g of crude base (73.7% of theory) were obtained, from which 14.7 g of the hydrochloride of 2-(dimethylaminopentafluorophenylmethyl) cyclohexanone (32.3% of theory) were obtained according to the procedure described in Example 1 ($2^{nd}$ Stage) with chlorotrimethylsilane/water in 2-butanone.

$2^{nd}$ Stage 1-benzyl-2-(dimethylaminopentafluorophlenylmethyl) cyclohexanol, hydrochloride The base was freed from 3.0 g (8.39 mmole) of the hydrochloride of 2-(dimethylaminopentafluorophenylmethyl) cyclohexanone obtained according to stage 1 with 30 ml of water and 5 ml of ammonia solution (25 vol. %), extracted three times with 30 ml of ether each time, and the combined organic extracts were dried over sodium sulfate, filtered, and concentrated by evaporation on a rotary evaporator without heating (500 to 10 mbar). 2.5 g (7.8 mmole) of this base were dissolved in 12 ml of tetrahydrofuran, added dropwise to 4.7 ml (9.3 mmole) of benzylmagnesium chloride (2 M solution in tetrahydrofuran) while cooling in an ice bath, and then stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 2.46 g of crude base (76.4% of theory) were obtained, from which 0.68 g of 1-benzyl-2-(dimethylaminopentafluorophenylmethyl)cyclohexanol, hydrochloride (19.4% of theory) was obtained according to the procedure described in Example 1 ($3^{rd}$ Stage). The hydrochloride decomposes on heating above 100° C.

Example 78

1-benzyl-2-(phenylpiperidin-1-ylmethyl) cyclohexanol, hydrochloride $1^{st}$ Stage 2-(phenylpiperidin-1-ylmethyl)cyclohexanone 10 g (47.7 mmole) of 1-benzylidenepiperidinium chloride were dissolved in 20 ml of dichlorometlhane and cooled to −70° C. in a cooling bath (isopropanol/dry ice). 7.21 g (47.7 mmole) of 1-(pyrrolidino)-1-cyclohexene were added and stirred for a further 15 hours at RT. The reaction mixture was worked up by adding 70 ml of semi-concentrated hydrochloric acid while cooling with ice, stirred for 10 minutes, washed twice with 70 ml of ether each time, and adjusted to the alkaline range (pH ca. 9) with 180 ml of dilute ammonia solution (5 vol. %). The reaction mixture was extracted three times with 70 ml of ether each time, and the combined organic extracts were dried over sodium sulfate, filtered, and concentrated by evaporation on a rotary evaporator (500 to 10 mbar) without heating. 8.73 g of crude base (67.5% of theory) were obtained, from which 6.3 g of the hydrochloride of 2-(phenylpiperidin-1-ylmethyl)cyclohexanone (42.9% of theory) were obtained according to the procedure described in Example 1 ($2^{nd}$ Stage) with chlorotrimethylsilane/water in 2-butanone.

$2^{nd}$ Stage 1-benzyl-2-(phenylpiperidin-1-ylmethyl)cyclohexanol, hydrochloride The base was freed from 2.5 g (8.12 mmole) of the hydrochloride of 2-(phenylpiperidin-1-ylmethyl) cyclohexanone obtained according to stage 1 with 25 ml of water and 5 ml of ammonia solution (25 vol. %), extracted three times with 30 ml of ether each time, and the combined organic extracts were dried over sodium sulfate, filtered, and concentrated by evaporation on a rotary evaporator without Heating (500 to 10 mbar). 2.00 g (7.4 mmole) of this base were dissolved in 10 ml of tetrahydrofuran, added dropwise to 4.4 ml (8.8 mmole) of benzylmagnesiun chloride (2 M solution in tetrahydrofuran) while cooling in an ice bath, and stirred for 15 hours at RT. The reaction mixture was worked up by adding 10 ml of saturated ammonium chloride solution while cooling in an ice bath, and was extracted three times at RT with 15 ml of ether each time. The combined organic extracts were dried over sodium sulfate, filtered, and concentrated on a rotary evaporator (500 to 10 mbar). 2.29 g of crude base (85.4% of theory) were obtained, from which 1.05 g of 1-benzyl-2-(phenylpiperidin-1-ylmethyl) cyclohexanol, hydrochloride (35.7% of theory) was obtained according to the procedure described in Example 1 ($3^{rd}$ Stage) with chlorotrimethylsilane/water in 2-butanone. The hydrochloride decomposes on heating above 218° C.

Example 79

4-dimethylaminophenylmethyl)-1-4-trifluoromethylphenyl)cyclohexanol, hydrochloride 0.76 g (31.0 mmole) of magnesium turnings was stirred in 15 ml. of ether of analysis purity. 4.46 ml (31.0 mmole) of 4-bromobenzotrifluoride dissolved in 15 ml of ether were arddecl dropwise so that the reaction mixture boiled gently. After completion of the addition the reaction mixture was stirred for a further hour at RT. 6.0 g (26.0 mmole) of the 2-{dimethylaminophenylmethyl)cyclohexanone prepared according to Example 1 were dissolved in 15 ml of ether, added dropwise to the Grignard reagent while cooling in an ice bath, and stirred for 15 hours at RT. The reaction mixture was worked up by adding 30 ml of saturated ammonium chloride solution while cooling in an ice bath, and was extracted three times at RT with 50 ml of ether each time. The combined organic extracts were dried over sodium sulfate, filtered, and concentrated by evaporation on a rotary evaporator (500 to 10 mbar). 8.49 g of crude base (86.7% of threory) were obtained, from which 6.62 g of 2-{dimethylaminophenylmethyl)-1-(4-trifluoromethylphenyl)cyclohexanol, hydrochloride (61.7% of theory) were obtained according to the procedure described in Example 1 ($3^{rd}$ Stage) with chlorotrimethylsilane/water in 2-butanone. The hydrochloride decomposes on heating above 170° C.

Example 80

3-(4-tert.-butylbenzyl)-1-[dimethylamino-2-methyl-1-phenylpentan-3-ol, hydrochloride 0.33 g (13.7 mmole) of magnesium turnings was stirred in 10 ml of ether of analysis purity. 2.50 g (13.7 mmole) of 4-tert.-butylbenzyl chloride dissolved in 10 ml of ether were added dropwise so that the reaction mixture boiled gently. After completion of the addition the reaction mixture was stirred for a further hour at BT. 2.60 g (11.2 mmole) of the 1-{dimethylamino-2-methyl-1-phenylpentan-3-one prepared according to Example 59 were dissolved in 10 ml of ether, added dropwise to the Grignard reagent while cooling in an ice bath, and stirred for 15 hours at RT. The reaction mixture was worked up by adding 20 ml of saturated amnmonium chloride solution while cooling in an ice bath, and was extracted three times at RT with 20 ml of ether each time. The combined organic extracts were dried over sodium sulfate, filtered, and concentrated by evaporation on a rotary evaporator (500 to 10 mbar). 3.93 g of crude base (93.8% of theory) were obtained, which were added to a 3.5×30 cm column filled with silica gel. Elution with ethyl acetate/hexane (1:4) yielded 0.59 g of base, from which 0.26 g of 3-(4-tert.-butylbenzyl)-1-dimethylamino-2-methyl-1-phenyl-pentan-3-ol, hydrochloride (5.6% of theory) were obtained according to the procedure described in Example 1 (3$^{rd}$ Stage) The hydrochloride decomposes on heating above 91° C.

Example 81

2-(dimethylamino-o-tolylmethyl)-1-phenylcyclohexanol, hydrochloride 2.50 g (9.3 mmole) of the 2-(dimethylamino-o-tolylmethyl)cyclohexanone prepared according to Example 66 were dissolved in 10 ml of tetrahydrofuran, added dropwise to 12.2 ml (12.2 mmole) of phenethylmagnesium chloride (1 M solution in tetrahydrofuran) while cooling in an ice bath, and stirred for 15 hours at RT. The reaction mixture was worked up by adding 15 ml of saturated ammonium chloride solution while cooling in an ice bath, and was extracted three times at RT with 15 ml of ether each time. The combined organic extracts were dried over sodium sulfate, filtered, and concentrated by evaporation on a rotary evaporator (500 to 10 mbar). 3.32 g of (true base (92.7% of theory) were obtained, from which 2-(diinethylamino-o-tolylmethyl)-1-phenylcyclohexanol, hydrochloride (52.9% of theory) with a melting point of 187° were obtained according to the procedure described in Example 1 (3$^{rd}$ Stage) with chlorotrimethylsilane/water in 2-butanone.

Example 82

1-(4-tert.-butylbenzyl)-2-[dimethylaminothiophen-2-ylmethyl]cyclohexanol, hydrochloride 0.31 g (12.6 mmole) of magnesium turnings was stirred in 10 ml of ether of analysis purity. 2.30 g (12.6 mmole) of 4-tert.-butylbenzyl bromide dissolved in 10 ml of ether were added dropwise so that the reaction mixture boiled gently. After completion of the addition the reaction mixture was stirred for a further hour at RT. 2.50 g (10.5 mmole) of the 2-(dimethylaminothiophen-2-ylmethyl)cyclohexanone prepared according to Example 70 were dissolved in 10 ml of ether, added dropwise to the Grigiard reagent while cooling in all ice bath, and stirred for 15 hours at RT. The reaction mixture was worked up by adding 15 ml of saturated ammonium chloride solution while cooling in an ice bath, and was extracted three times at RT with 20 ml of ether each time. The combined organic extracts were dried over sodium sulfate, filtered, and concentrated by evaporation on a rotary evaporator (500 to 10 mbar). 3.69 g of crude base (90.7% of theory) were obtained, from which 1.16 g of 1-(4-tert.-butylbenzyl)-2-[dimethylaminothiophen-2-ylmethyl]cyclohexanol, hydrochloride (26.2% of theory) were obtained according to the procedure described in Example 1 (3$^{rd}$ Stage) with chlorotrimethylsilane/water in 2-butanone. The hydrochloride decomposes on heating above 210° C.

What is claimed is:
1. A substituted 3-amino-3-arylpropan-1-ol compound corresponding to formula I:

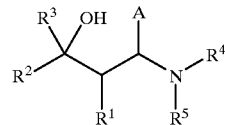

wherein
$R^1$ and $R^2$ each independently denote $C_{1-6}$ alkyl, or $R^1$ and $R^2$ together denote a $(CH_2)_{2-6}$ ring which may be substituted by phenyl,
$R^3$ denotes $C_{3-6}$ alkyl, $C_{3-6}$ cycloalkyl, aryl which may contain heteroatoms in the ring system and which may carry substituents $R^6$ to $R^8$ on the aryl ring, or a substituted $C_{1-3}$ alkylphenyl group corresponding to formula XII:

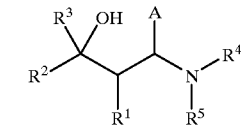

n = 1, 2 or 3

$R^4$ and $R^5$ each independently denote $C_{1-6}$ alkyl, $C_{3-6}$ cycloalkyl, phenyl, benzyl, or phenethyl, or $R^4$ and $R^5$ together form a $(CH_2)_{3-6}$ ring or $CH_2CH_2OCH_2CH_2$ ring,
$R^6$ to $R^8$ each independently denote H, F, Cl, Br, $CHF_2$, $CF_3$, OH, $OCF_3$, $OR^{14}$, $NR^{15}R^{16}$, $SR^{14}$, phenyl, $SO_2CH_3$, $SO_2CF_3$, $C_{1-6}$ alkyl, CN, $COOR^{14}$, or $CONR^{15}R^{16}$, or $R^6$ and $R^7$ together form a $OCH_2O$, $OCH_2CH_2O$, CH=CHO, CH=C(CH$_3$)O or $(CH_2)_4$ ring, wherein
$R^{14}$ denote $C_{1-6}$ alkyl, phenyl, benzylt or phenethyl, and
$R^{15}$ and $R^{16}$ each independently denote H, $C_{1-6}$ alkyl, phenyl, benzyl or phenethyl, and
A denotes an aryl radical which may contain heteroatoms in the ring system and which may be be substituted,
or a diastereomer or enantiomer thereof,
or a salt thereof with a physiologically acceptable acid, with the proviso that 1-benzyl-2-(dimethylaminophenylmethyl) cyclohexanol, diastereomers thereof, enantiomers thereof and reaction products thereof with methyliodide are excluded.

2. A compound according to claim 1, wherein $R^1$ and $R^2$ together form a $(CH_2)_{2-6}$ ring which may be substituted by phenyl.

3. A compound according to claim 2, wherein $R^1$ and $R^2$ together form a $(CH_2)_4$ ring which may be substituted by phenyl.

4. A compound according to claim 1, wherein $R^3$ denotes a substituted $C_{1-3}$-alkylphenyl group corresponding to formula XII.

5. A compound according to claim 1 wherein $R^3$ denotes an aryl radical which may contain heteroatoms in the ring system.

6. A compound according to claim 1, wherein A denotes a sbstituted phenyl group corresponding to formula XI:

XI

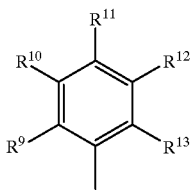

wherein
$R^9$ to $R^{13}$ each independently denote H, F, Cl, Br, I, $CF_3$, OH, $OR^{14}$, $OCF_3$ $SR^{14}$, $SO_2CH_3$, $SO_2CF_3$, $C_{1-6}$-alkyl, phenyl, CN, $COOR^{14}$, $NO_2$, or $R^9$ and $R^{10}$ or $R^{10}$ and $R^{11}$ together form a $OCH_2O$ or $OCH_2CH_2O$ ring, and
$R^{14}$ denotes $C_{1-6}$ alkyl, phenyl, benzyl, phenethyl, or
A denotes unsubstituted thiophene or thiophene substituted with at least one substituent selected from the group consisting of $C_{1-6}$ alkyl, halogen, OR, SR, aryl $SO_2R$, $NO_2$, CN and COOR, wherein R is $C_{1-6}$ alkyl, or unsubstituted furan or furan substituted with at least one substituent selected from the group consisting of $C_{1-6}$ alkyl, halogen, OR, SR, aryl $SO_2R$, $NO_2$, CN and COOR, wherein R is $C_{1-6}$ alkyl.

7. A compound according to claim 1, wherein $R^1$ and $R^2$ together form a $(CH_2)_{2-6}$ ring which may be substituted by phenyl, and $R^3$ denotes a substituted $C_{1-3}$ alkylphenyl group corresponding to formula XII.

8. A compound according to claim 1, wherein $R^1$ and $R^2$ together form a $(CH_2)_{2-6}$ ring which may be substituted by phenyl, and $R^3$ denotes an aryl radical which may contain heteroatoms in the ring system.

9. A compound according to claim 1, wherein $R^1$ and $R^2$ together form a $(CH_2)_4$ ring which may be substituted by phenyl; A denotes a radical selected from the group consisting of substituted phenyl corresponding to formula XI, unsubstituted thiophene, substituted thiophene, unsubstituted furan and substituted furan, and $R^3$ denotes a substituted $C_{1-3}$ alkylphenyl group corresponding to formula XII, and wherein the thiophene or furan substituents are selected from the group consisting of $C_{1-6}$ alkyl, Br, Cl, F, OR, SR, aryl $SO_2R$, $NO_2$, CN and COOR, wherein R is $C_{1-6}$ alkyl.

10. A compound according to claim 1, wherein $R^1$ and $R^2$ together form a $(CH_2)_4$ ring which may be substituted by phenyl, A denotes a radical selected from the group consisting of substituted phenyl corresponding to formula XI, unsubstituted thiophene, substituted thiophene, unsubstituted furan and substituted furan; and $R^3$ denotes an aryl radical which may contain heteroatoms in the ring system, and wherein the thiophene or furan substituents are selected from the group consisting of $C_{1-6}$ alkyl, Br, Cl, F, OR, SR, aryl $SO_2R$, $NO_2$, CN and COOR, wherein R is $C_{1-6}$ alkyl.

11. A compound according to claim 1, wherein $R^1$ and $R^2$ together form a $(CH_2)_4$ ring; A denotes a radical selected from the group consisting of substituted phenyl corresponding to formula XI, unsubstituted thiophene and substituted thiophene, and $R^3$ denotes a substituted $C_{1-3}$ alkylphenyl group corresponding to formula XII, and wherein the thiophene or furan substituents are selected from the group consisting of $C_{1-6}$ alkyl, Br, Cl, F, OR, SR, aryl $SO_2R$, $NO_2$, CN and COOR, wherein R is $C_{1-6}$ alkyl.

12. A compound according to claim 1, wherein $R^1$ and $R^2$ together form a $(CH_2)_4$ ring; A denotes a radical selected from the group consisting of substituted phenyl corresponding to formula XI, unsubstituted thiophene and substituted thiophene; and $R^3$ denotes an aryl radical which may contain heteroatoms in the ring system, and wherein the thiophene or furan substituents are selected from the group consisting of $C_{1-6}$ alkyl, Br, Cl, F, OR, SR, aryl $SO_2R$, $NO_2$, CN and COOR, wherein R is $C_{1-6}$ alkyl.

13. A compound according to claim 1, wherein $R^1$ and $R^2$ together form a $(CH_2)_4$ ring, A denotes unsubstituted or substituted thiophene, and $R^3$ denotes a substituted $C_{1-3}$ alkylphenyl group corresponding to formula XII, and wherein the thiophene or furan substituents are selected from the group consisting of $C_{1-6}$ alkyl, Br, Cl, F, OR, SR, aryl $SO_2R$, $NO_2$, CN and COOR, wherein R is $C_{1-6}$ alkyl.

14. A compound according to claim 1, wherein $R^1$ and $R^2$ together form a $(CH_2)_4$ ring, A denotes unsubstituted or substituted thiophene, and $R^3$ denotes an aryl radical which may contain heteroatoms in the ring system, and wherein the thiophene or furan substituents are selected from the group consisting of $C_{1-6}$ alkyl, Br, Cl, F, OR, SR, aryl $SO_2R$, $NO_2$, CN and COOR, wherein R is $C_{1-6}$ alkyl.

15. A compound according to claim 1, wherein $R^1$ and $R^2$ together form a $(CH_2)_4$ ring, A denotes unsubstituted or substituted furan, and $R^3$ denotes a substituted $C_{1-3}$ alkylphenyl group corresponding to formula XII.

16. A compound according to claim 1, wherein $R^1$ and $R^2$ together form a $(CH_2)_4$ ring, A denotes unsubstituted or substituted furan, and $R^3$ denotes an aryl radical which may contain heteroatoms in the ring system.

17. A compound according to claim 1, selected from the group consisting of:
- 2-(dimethylaminophenylmethyl)-1-(3-methoxyphenyl) cyclohexanol,
- 2-(dimethylaminophenylmethyl)-1-(3-fluorophenyl) cyclohexanol,
- 2-(dimethylaminophenylmethyl)-1-phenylcyclohexanol,
- 3-[2-(dimethylaminophenylmethyl)-1-hydroxycyclohexyl]phenol,
- 2-(dimethylaminophenylmethyl)-1-(4-methoxyphenyl) cyclohexanol,
- 1-(4-chlorophenyl)-2-(dimethylaminophenylmethyl) cyclohexanol,
- 2-(dimethylaminophenylmethyl)-1-(4-fluorophenyl) cyclohexanol,
- 2-(dimethylaminophenylmethyl)-1-p-tolylcyclohexanol,
- 1-(3-chlorophenyl)-2-[dimethylamino-(3-methoxyphenyl)methyl]cyclohexanol,
- 1-(4-dimethylaminophenyl)-2-(dimethylaminophenylmethyl]cyclohexanol,
- 1-benzo[1,3]dioxol-4-yl-2-(dimethylaminophenylmethyl)cyclohexanol,
- 1-(3,4-dimethoxyphenyl)-2-(dimethylaminophenylmethyl)cyclohexanol,
- 2-(dimethylaminophenylmethyl)-1-(3-methoxybenzyl) cyclohexanol,
- 2-(dimethylaminophenylmethyl)-1-(4-fluoro-3-trifluoromethylphenyl)cyclohexanol,
- 2-(dimethylaminophenylmethyl)-1-(4-trifluoromethoxybenzyl)cyclohexanol,
- 2-(dimethylaminophenylmethyl)-1-furan-3-yl cyclohexanol,
- 1-butyl-2-(dimethylaminophenylmethyl)cyclohexanol,
- 1-(3,4-dichlorophenyl)-2-(dimethylaminophenylmethyl) cyclohexanol,
- (+)-1-(3,4-dichlorophenyl)-2-(dimethylaminophenylmethyl)cyclohexanol,
- (−)-1-(3,4-dichlorophenyl)-2-(dimethylaminophenylmethyl)cyclohexanol 4-[2-(dimethylaminophenylmethyl)-1-hydroxycyclohexyl]phenol,
2-(dimethylaminophenylmethyl)-1-naphthalene-2-yl cyclohexanol,
2-[dimethylamino-(4-trifluoromethylphenyl)methyl]-1-(3-methoxybenzyl)cyclohexanol,
1-(4-chlorobenzyl)-2-(dimethylaminophenylmethyl)-1-cyclohexanol,
2-(dimethylaminophenylmethyl)-1-(2-fluorobenzyl) cyclohexanol,
2-(dimethylaminophenylmethyl)-1-(4-fluorobenzyl) cyclohexanol,
1-(2,5-dimethoxyphenyl)-2-(dimethylaminophenylmethyl)cyclohexanol,
1-(2-chloro-4-fluorobenzyl)-2-(dimethylaminophenyl-methyl)cyclohexanol,
1-(4-tert.-butylbenzyl)-2-(dimethylaminophenylmethyl)cyclohexanol,
2-(dimethylaminophenylmethyl)-1-(3-fluorobenzyl)cyclohexanol,
1-(2-chlorobenzyl)-2-(dimethylaminophenylmethyl)cyclohexanol,
1-benzo[1,3]dioxol-5-yl-2-[dimethylamino(3-methoxyphenyl)-methyl]cyclohexanol,
1-(3-chlorobenzyl)-2-(dimethylaminophenylmethyl)cyclohexanol,
1-(2,4-dichlorobenzyl)-2-(dimethylaminophenylmethyl)cyclohexanol,
1-benzyl-2-[dimethylaminophenyl-(3-phenoxyphenyl)methyl]cyclohexanol,
1-benzyl-2-(dimethylaminophenyl-(3-methoxyphenyl)methyl]cyclohexanol,
2-(dimethylaminophenylmethyl)-1-(3-trifluoromethyl benzyl)cyclohexanol,
2-(dimethylamino-(3-methoxyphenyl)methyl]-1-(3-methoxybenzyl)cyclohexanol,
2-[(2-chlorophenyl)dimethylaminomethyl]-1-naphthalene-2-yl cyclohexanol,
1-benzyl-2-[(3,4-dichlorophenyl)dimethylaminomethyl]cyclohexanol,
2-[(3,4-dichlorophenyl)(dimethylaminomethyl]-1-phenethyl cyclohexanol,
1-benzyl-2-[dimethylamino-(4-fluorophenyl)methyl]cyclohexanol,
2-[(3-chlorophenyl)(dimethylaminomethyl]-1-phenyl cyclohexanol,
1-(2,4-dichlorophenyl)-2-(3-dimethylaminomethyl)-1-cyclohexanol,
1-benzyl-2-[(3-chlorophenyl)dimethylaminomethyl]cyclohexanol,
1-benzyl-2-[(2-chlorophenyl)dimethylaminomethyl]cyclohexanol,
1-(4-tert.-butylbenzyl)-2-[(3,4-dichlorophenyl)dimethylaminomethyl]cyclohexanol,
2-[dimethylamino-(4-fluorophenyl)methyl]-1-(3-trifluoromethylbenzyl)cyclohexanol,
2-(dimethylaminophenylmethyl)bicyclohexyl-1-ol,
2-(dimethylaminophenylmethyl)-1-(4-methoxybenzyl)cyclohexanol,
1-(2,4-difluorobenzyl)-2-(dimethylaminophenylmethyl)cyclohexanol,
1-(4-tert.-butylbenzyl)-2-[(3-chlorophenyl)dimethylaminomethyl]cyclohexanol,
2-[dimethylamino-(3-phenoxyphenyl)methyl]-1-phenethyl cyclohexanol,
2-[dimethylamino-(3-phenoxyphenyl)methyl]-1-(3-trifluoromethylbenzyl)cyclohexanol,
1-(2,5-difluorobenzyl)-2-(dimethylaminophenylmethyl) cyclohexanol,
1-(3,4-difluorobenzyl)-2-(dimethylaminophenylmethyl) cyclohexanol,
1-(2-chloro-6-fluorobenzyl)-2-(dimethylaminophenylmethyl)cyclohexanol,
1-(2,3-difluorobenzyl)-2-(dimethylaminophenylmethyl) cyclohexanol,
1-benzyl-2-[(4-chlorophenyl)dimethylaminomethyl] cyclohexanol,
1-dimethylamino-3-ethyl-2-methyl-1,5-diphenylpentane-3-ol,
1-(2-chlorobenzyl)-2-[(2-chlorophenyl)-dimethylaminomethyl]cyclohexanol,
1-benzyl-2-[(4-bromophenyl)dimethylaminomethyl] cyclohexanol,
2-[(4-chlorophenyl)dimethylaminomethyl]-1-(4-trifluoromethylphenyl)cyclohexanol,
2-[(4-chlorophenyl)dimethylaminomethyl]-1-(3-trifluoromethylbenzyl)cyclohexanol,
1-(4-tert.-butylbenzyl)-2-[dimethylamino-(3-phenoxyphenyl)methyl]cyclohexanol,
4-{dimethylamino-[2-hydroxy-2-(4-trifluoromethylphenyl)cyclohexyl]methyl}benzonitryl,
2-(dimethylamino-o-tolylmethyl)-1-phenylcyclohexanol,
1-benzyl-2-(dimethylamino-o-tolylmethyl)cyclohexanol,
2-(dimethylaminophenylmethyl)-1-(3-phenylpropyl) cyclohexanol,
2-[(2-chlorophenyl)dimethylaminomethyl]-1-[2-(4-fluorophenyl)ethyl]cyclohexanol,
2-[dimethylaminothiophen-2-ylmethyl]-1-(3-trifluoromethylbenzyl)cyclohexanol,
Methyl-4-[2-(dimethylaminophenylmethyl)-1-hydroxycyclohexyl]benzoate,
1-benzyl-2-(dimethylaminophenylmethyl)-4-phenylcyclo-hexanol,
1-(4-bromophenyl)-2-(dimethylaminophenylmethyl) cyclo-hexanol,
2-(dimethylaminophenylmethyl)-1-naphthalene-1-ylcyclo-hexanol,
2-(dimethylaminophenylmethyl)-1-(2-methylsulfanylphenyl)cyclohexanol,
1-benzyl-2-(dimethylaminonaphthalene-2-ylmethyl) cyclohexanol,
1-benzyl-2-(dimethylaminonapentafluorophenylmethyl) cyclohexanol,
1-benzyl-2-(phenylpiperidin-1-ylmethyl)cyclohexanol,
2-(dimethylaminophenylmethyl)-1-(4-trifluoromethylphenyl)cyclohexanol,
3-(4-tert.-butylbenzyl)-1-dimethylamino-2-methyl-1-phenylpentan-3-ol,
2-(dimethylamino-o-tolylmethyl)-1-phenethylcyclohexanol,
1-(4-tert.-butylbenzyl)-2-[dimethylaminothiophen-2-ylmethyl]cyclohexanol; and the hydrochloride salts of each of the foregoing compounds, and 1-benzyl-2-(dimethylaminophenylmethyl)cyclohexanol hydrochloride.

18. A pharmaceutical composition comprising at least one substituted 3-amino-3-arylpropan-1-ol compound corresponding to formula I:

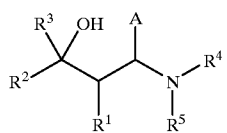

wherein $R^1$ and $R^2$ each independently denote $C_{1-6}$ alkyl, or $R^1$ and $R^2$ together denote a $(CH_2)_{2-6}$ ring which may be substituted by phenyl, $R^3$ denotes $C_{3-6}$ alkyl, $C_{3-6}$ cycloalkyl, aryl which may contain heteroatoms in the ring system and which may carry substituents $R^6$ to $R^8$ on the aryl ring, or a substituted $C_{1-3}$ alkylphenyl group corresponding to formula XII:

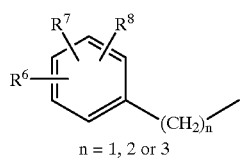

n = 1, 2 or 3

$R^4$ and $R^5$ each independently denote $C_{1-6}$ alkyl, $C_{3-6}$ cycloalkyl, phenyl, benzyl, or phenethyl, or $R^4$ and $R^5$ together form a $(CH_2)_{3-6}$ ring or $CH_2CH_2OCH_2CH_2$ ring, $R^6$ to $R^8$ each independently denote H, F, Cl, Br, $CHF_2$, $CF_3$, OH, $OCF_3$, $OR^{14}$, $NR^{15}R^{16}$, $SR^{14}$, phenyl, $SO_2CH_3$, $SO_2CF_3$, $C_{1-6}$ alkyl, CN, $COOR^{14}$, or $CONR^{15}R_{16}$, or $R^6$ and $R^7$ together form a $OCH_2O$, $OCH_2CH_2O$, CH=CHO, CH=C(CH_3)O or $(CH_2)_4$ ring, wherein $R^{14}$ denotes $C_{1-6}$ alkyl, phenyl, benzyl, or phenethyl, and $R^{15}$ and $R^{16}$ each independently denote H, $C_{1-6}$ alkyl, phenyl, benzyl or phenethyl, and A denotes an aryl radical which may contain heteroatoms in the ring system and which may be substituted, or a diastereomer or enantiomer thereof, or a salt thereof with a physiologically acceptable acid, and at least one pharmaceutical carrier or adjuvant.

19. A pharmaceutical composition according to claim 18, wherein said at least one compound comprises a mixture of two enantiomers in which the two enantiomers are present in unequal molar amounts.

20. A pharmaceutical composition according to claim 19, wherein said mixture of enantiomers comprises between 5 and 45 wt. % of one of said two enantiomers.

21. A process for preparing a compound according to claim 1, said process comprising:

reacting a Mannich base corresponding to formula II:

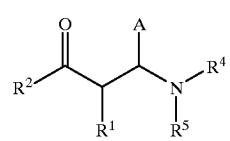

wherein $R^1$, $R^2$, $R^4$ and $R^5$ and A have the meanings given in claim 1, with an organometallic compound $R^3Y$, wherein Y denotes MgCl, MgBr, MgI or Li, and $R^3$ has the meaning given in claim 1, to form an alcohol corresponding to formula I:

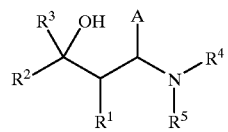

wherein $R^1$ to $R^5$ and A have the meanings given above.

22. A method of relieving pain comprising the step of administering to a patient in need thereof an effective pain relieving amount of a pharmaceutical composition according to claim 18.

23. A method according to claim 22, wherein said pain is neuropathic pain.

24. A method according to claim 22, wherein said pain is chronic pain.

25. A method of local anaesthesia comprising administering to a patient an effective anaesthesia inducing amount of a pharmaceutical composition according to claim 18.

26. A method of inhibiting arrhythmia in a mammal comprising administering to said mammal an effective anti-arrhythmic amount of a pharmaceutical composition according to claim 18.

27. A method of inhibiting emetic activity comprising administering to a patient an effective anti-emetic amount of a pharmaceutical composition according to claim 18.

28. A method of promoting nootropic (neurotropic) activity in a patient comprising administering to said patient an effective nootropic (neurotropic) activity promoting amount of a pharmaceutical composition according to claim 18.

29. A method of treating cardiovascular conditions in a mammal, said method comprising administering to said mammal an effective cardiovascular condition treating amount of a pharmaceutical composition according to claim 18.

30. A method of treating urinary incontinence comprising administering to a patient an effective continence promoting amount of a pharmaceutical composition according to claim 18.

31. A method of treating diarrhea comprising administering to a patient an effective diarrhea inhibiting amount of a pharmaceutical composition according to claim 18.

32. A method of treating pruritis comprising administering to a patient an effective pruritis inhibiting amount of a pharmaceutical composition according to claim 18.

33. A method of treating alcohol dependence comprising administering to a patient an effective alcohol dependence alleviating amount of a pharmaceutical composition according to claim 18.

34. A method of treating narcotics dependence comprising administering to a patient an effective narcotics dependence alleviating amount of a pharmaceutical composition according to claim 18.

35. A method of treating drug dependence comprising administering to a patient an effective drug dependence alleviating amount of a pharmaceutical composition according to claim 18.

36. A method for treating inflammation in a patient comprising administering to said patient an effective inflammation alleviating amount of a pharmaceutical composition according to claim 18.

37. A method of alleviating depression comprising administering to a patient an effective depression inhibiting amount of a pharmaceutical composition according to claim 18.

38. A method of enhancing libido comprising administering to a patient an effective libido enhancing amount of a pharmaceutical composition according to claim 18.

39. A method of improving alertness and attentiveness comprising administering to a patient an effective alertness and attentiveness improving amount of a pharmaceutical composition according to claim 18.

* * * * *